(12) United States Patent
Bitinaite

(10) Patent No.: US 8,440,401 B2
(45) Date of Patent: May 14, 2013

(54) METHODS AND COMPOSITIONS FOR DNA MANIPULATION

(75) Inventor: Jurate Bitinaite, Rowley, MA (US)

(73) Assignee: New England Biolabs, Inc., Ipswich, MA (US)

(*) Notice: Subject to any disclaimer, the term of this patent is extended or adjusted under 35 U.S.C. 154(b) by 0 days.

(21) Appl. No.: 13/052,536

(22) Filed: Mar. 21, 2011

(65) Prior Publication Data

US 2011/0262973 A1 Oct. 27, 2011

Related U.S. Application Data

(60) Continuation of application No. 12/192,503, filed on Aug. 15, 2008, now abandoned, which is a division of application No. 10/407,637, filed on Apr. 4, 2003, now Pat. No. 7,435,572.

(60) Provisional application No. 60/372,352, filed on Apr. 12, 2002, provisional application No. 60/372,675, filed on Apr. 15, 2002, provisional application No. 60/421,010, filed on Oct. 24, 2002.

(51) Int. Cl.
*C12Q 1/68* (2006.01)
*C07H 21/02* (2006.01)
*C07H 21/04* (2006.01)

(52) U.S. Cl.
USPC ..................... 435/6.1; 536/23.1; 536/24.3

(58) Field of Classification Search .................. None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 5,137,814 A | 8/1992 | Rashtchian et al. |
| 5,229,283 A | 7/1993 | Berninger |
| 5,333,675 A | 8/1994 | Mullis et al. |
| 5,334,515 A | 8/1994 | Rashtchian et al. |
| 6,358,712 B1 | 3/2002 | Jarrell et al. |
| 6,395,523 B1 | 5/2002 | Kong et al. |
| 6,660,475 B2 | 12/2003 | Jack et al. |
| 6,867,028 B2 | 3/2005 | Janulaitis et al. |
| 2003/0113737 A1 | 6/2003 | Pedersen |

FOREIGN PATENT DOCUMENTS

| | | |
|---|---|---|
| EP | 1176204 A1 | 1/2002 |
| WO | 97/35026 A1 | 9/1997 |
| WO | 99/47536 A2 | 9/1999 |
| WO | 00/50632 A2 | 8/2000 |
| WO | 01/94544 A2 | 12/2001 |
| WO | 02/059357 A2 | 8/2002 |
| WO | 03055975 A2 | 7/2003 |

OTHER PUBLICATIONS

Nisson et al PCR Methods Apps 1 120-123 1991.
Piccirilli et al Nature 343 33-37 1990.
Pourquier et al Journal of Biological Chemistry 274 13 8516-8523 1999.
Promega Catalog 1993-94 p. 158.
Purmal et al Journal of Biological Chemistry 278 16 10026-10035 1998.
Purmal et al Nucleic Acids Research 22 1 72-78 1994.
Radicella et al Proceedings Natioanl Academy Science 94 8010-8015 1997.
Rashtchian Current Opinion Biotechnology 6 30-36 1995.
Rashtchian et al PCR Methods Applications 2 124-130 1992.
Robson and Hickson Nucleic Acids Research 19 20 5519-5523 1991.
Sakumi et al Journal Biological Chemistry 261 33 15761-15766 1986.
Saporito and Cunningham Journal of Bacteriology 5141-5145 1988.
Sarkar and Sommer BioTechniques 8 4 404-407 1990.
Sarkar and Sommer Nucleic Acids Research 20 18 4937-4938 1992.
Scharf et al Science 233 1076-1078 1986.
Seawall Journal of Virology 35 3 790-797 1980.
Senturker et al Nucleic Acids Research 26 23 5270-5276 1998.
Smith and Klugman BioTechniques 22 438-442 1997.
Smith et al PCR Methods and Applications 2 328-332 1993.
Stoker Nucleic Acids Research 18 14 4290 1990.
Takao, Protein, Nucleic Acid, Enzyme, 46, 8, 924-932, 2001.
Tchou and Grollman Journal of Biological Chemistry 270 19 11671-11677 1995.
Vaisvila et al Molecular Microbiology 42 3 587-601 2001.
Varshney and van de Sande Biochemistry 30 16 1991.
Varshney et al Journal Biological Chemistry 263 16 7776-7784 1988.
Vidal et al Nucleic Acids Research 29 6 1285-1292 2001.
Watson and Bennet Biotechniques 23 858-864 1997.
Yanisch-Perron et al Gene 33 103-119 1985.
Yao and Kow Journal of Biological Chemistry 272 49 30774-30779 1997.
Zhang et al Nucleic Acids Research 25 20 3969-3973 1997.
Sambrook Molecular Cloning: A Laboratory Manual 8.4-8.29 2001.
Evans and Linn Journal of Biological Chemistry 259 16 10252-10259 1984.
Andersson et al Analytical Biochem 218 300-308 1994.
Aslanidis and Jong Nucleic Acids Research 18 20 6069-6074 1990.
Barrett et al Cell 92 117-129 1988.
Barzilay et al Nucleic Acid Research 23 9 1544-1550 1995.
Berdal et al EMBO Journal 17 2 363-367 1998.
International search report PCT/US03/10296.
Boiteux et al EMBO Journal 6 10 3177-3183 1987.

(Continued)

*Primary Examiner* — Teresa E Strzelecka
(74) *Attorney, Agent, or Firm* — New England Biolabs, Inc; Harriet M. Strimpel

(57) ABSTRACT single-stranded extension having a desired length and sequence composition. Methods for forming single-stranded extensions include: the use of a cassette containing at least one nicking site and at least one restriction site at a predetermined distance from each other and in a predetermined orientation; or primer-dependent amplification which introduces into a polynucleotide molecule, a modified nucleotide which is excised to create a nick using a nicking agent. The methods and compositions provided can be used to manipulate a DNA sequence including introducing site specific mutations into a polynucleotide molecule and for cloning any polynucleotide molecule or set of joined polynucleotide molecules in a recipient molecule such as a vector of choice.

10 Claims, 40 Drawing Sheets

OTHER PUBLICATIONS

Boiteux et al Journal Biological Chemistry 265 7 3916-3922 1990.
Booth et al Gene 146 303-308 1994.
Chen et al BioTechniques 32 516-520 2002.
Clark Nucleic Acids Research 16 20 9677-9686 1988.
Colosimo et al BioTechniques 26 870-873 1999.
Cooney BioTechniques 24 30-34 1998.
Demple et al Proceedings National Academy Sciences 88 11450-11454 1991.
Dianov Current Biology 4 1069-1076 1994.
Duarte et al Nucleic Acids Research 27 2 496-502 1999.
Duarte et al Nucleic Acids Research 28 7 1555-1563 2000.
Gordon and Haseltine Journal of Biological Chemistry 255 24 12047-12050 1980.
Harrison et al Nucleic Acids Research 26 4 932-941 1998.
Haun et al BioTechniques 13 4 516-518 1992.
He et al Mutation Research 459 109-114 2000.
Hemsley et al NAR 17 16 6545-6551 1989.
Higuchi et al Nucleic Acids Research 16 15 7351-7367 1988.
Hill et al Nucleic Acids Research 26 5 1144-1149 1998.
Ho et al Gene 77 51-59 1989.
Horlacher et al Proceeding National Academy Sciences 92 6329-6333 1995.
Ikeda, et al, Protein, Nucleic Acid, Enzyme, 46, 8, 916-923, 2001.
Jiang et al Journal Biological Chemistry 272 51 32230-32239 1997.
Kaluz and Flint Nucleic Acids Research 22 22 4845 1994.
Kamiya et al Nucleic Acids Research 23 15 2893-2899 1995.
Kamiya_etal_NAR_28_7_1640-1646_2000.
Kammann et al Nucleic Acids Research 17 13 5404 1989.
Kaufman and Evans BioTechniques 9 3 304-306 1990.
Kuijper et al Gene 112 147-155 1992.
Landt et al Gene 96 125-128 1990.
Levin et al Journal of Biological Chemistry 263 17 8066-8071 1988.
Ling et al Analytical Biochemistry 254 157-178 1997.
Liu and Doetsch Nucleic Acids Research 26 7 1707-1712 1998.
Liu and Schwartz Biotechniques 12 28-30 1992.
Ljungquist Journal of Biological Chemistry 252 9 2806-2814 1977.
Lutz et al Nucleic Acids Research 27 13 2782-2798 1999.
Lutz Nucleic Acids Research 24 7 1308-1313 1996.
Marchuk et al Nucleic Acids Research 19 5 1154 1991.
Matsumoto et al Nucleic Acids Research 29 9 1975-1981 2001.
Mazumder et al Biochemistry 30 1119-1126 1990.
Nakabeppu et al Journal of Biological Chemistry 259 22 13730-13736 1984.
NEB Catalog 1993-94 p. 65.
NEB Catalog 1993-94 p. 66.
NEB Catalog 1998-99 p. 90.
NEB Catalog 2002-03 p. 318.

U - INDICATES DEOXYURIDINE
* - INDICATES FLOURESCEIN LABEL

*FIG. 26A*

|  |  | NdeI (OPTIONAL) |
|---|---|---|
| (a) | LEFT PRIMER: | 5'-GGAGACA U (ATG) NNNNNNN... |
|  |  | 5'-TERMINAL SEQUENCE |

(b) RIGHT PRIMER:  5'-GGGAAAG U NNNNNNNNNNN...
                   3'-TERMINAL SEQUENCE

FIG. 27B

```
                                              BssHII
                           EcoRI    SacI      AscI
          ------ag tgA ATT CGA GCT CAG GCG CGC C
pNEB205A
          ------tc acT TAA GCT CGA GTC CGC GCG G
                        •                •
                       400              410

... S   N   S   S   L   R   A

PacI         N.BbvCIB         XbaI         N.BbvCIB      PmeI
                                    ▼                         
  TT AAT TAA GCT GAG GGA AAG TCT AGA TGT CTC CTC AGC GTT TAA AC
  AA TTA ATT CGA CTC CCT TTC AGA TCT ACA GAG GAG TCG CAA ATT TG
        •             ▲             ▲                       •
       420                                                  460
   K   I   L   S   L   S   S   R   S   T   E   E   A   N   L   G

SbfI
  PstI         HindIII
  C CTG CAG GAA GCT TGG cgt aat cat ggt cat ------
                                                   pNEB205A
  G GAC GTC CTT CGA ACC gca tta gta cca gta ------
          •                         •
         470                       490

Q   L   F   S   P   T   I   M   T   M
                        lacZα TRANSLATIONAL START
```

FIG. 27C

```
                              BssHII
           EcoRI    SacI      AscI
------- ag tgA ATT CGA GCT CAG GCG CGC C
pNEB205A
------- tc acT TAA GCT CGA GTC CGC GCG G
              •                 •
             400               410

PacI        N.BbvCIB              N.BbvCIB        PmeI

TT AAT TAA GCT GAG GGA AAG T      TC AGC GTT TAA AC
AA TTA ATT CGA CT         T ACA GAG GAG TCG CAA ATT TG
   •                                                •
  420                                              460
                           T   E   E   A   N   L   G

SbfI
PstI        HindIII

C CTG CAG GAA GCT TGG cgt aat cat ggt cat -------
G GAC GTC CTT CGA ACC gca tta gta cca gta  pNEB205A
         •                      •         -------
        470                    490  |
    Q  L  F  S  P  T  I  M  T  M
              lacZα TRANSLATIONAL START  |
```

| AMOUNT OF PCR PRODUCT IN 10 μl OF PCR REACTION | | # OF COLONIES IN 25 μl OF TRANSFORMATION REACTION | | FRACTION OF RECOMBINANT COLONIES (%) |
|---|---|---|---|---|
| (ng) | (pmol) | WHITE | BLUE | |
| 0 | 0 | 0 | 23 (±3)* | - |
| 5 | 0.008 | 48 (±10) | 21 (±4) | 70 (±8) |
| 10 | 0.016 | 78 (±12) | 22 (±4) | 78 (±1) |
| 17 | 0.03 | 166 (±19) | 24 (±5) | 87 (±3) |
| 45 | 0.07 | 348 (±23) | 21 (±5) | 94 (±2) |
| 82 | 0.13 | 321 (±23) | 17 (±6) | 95 (±2) |
| 164 | 0.26 | 412 (±29) | 27 (±8) | 94 (±1) |
| 215 | 0.34 | 486 (±57) | 25 (±3) | 95 (±1) |
| 346 | 0.55 | 405 (±25) | 26 (±1) | 94 (±1) |
| 390 | 0.62 | 416 (±27) | 25 (±6) | 94 (±1) |

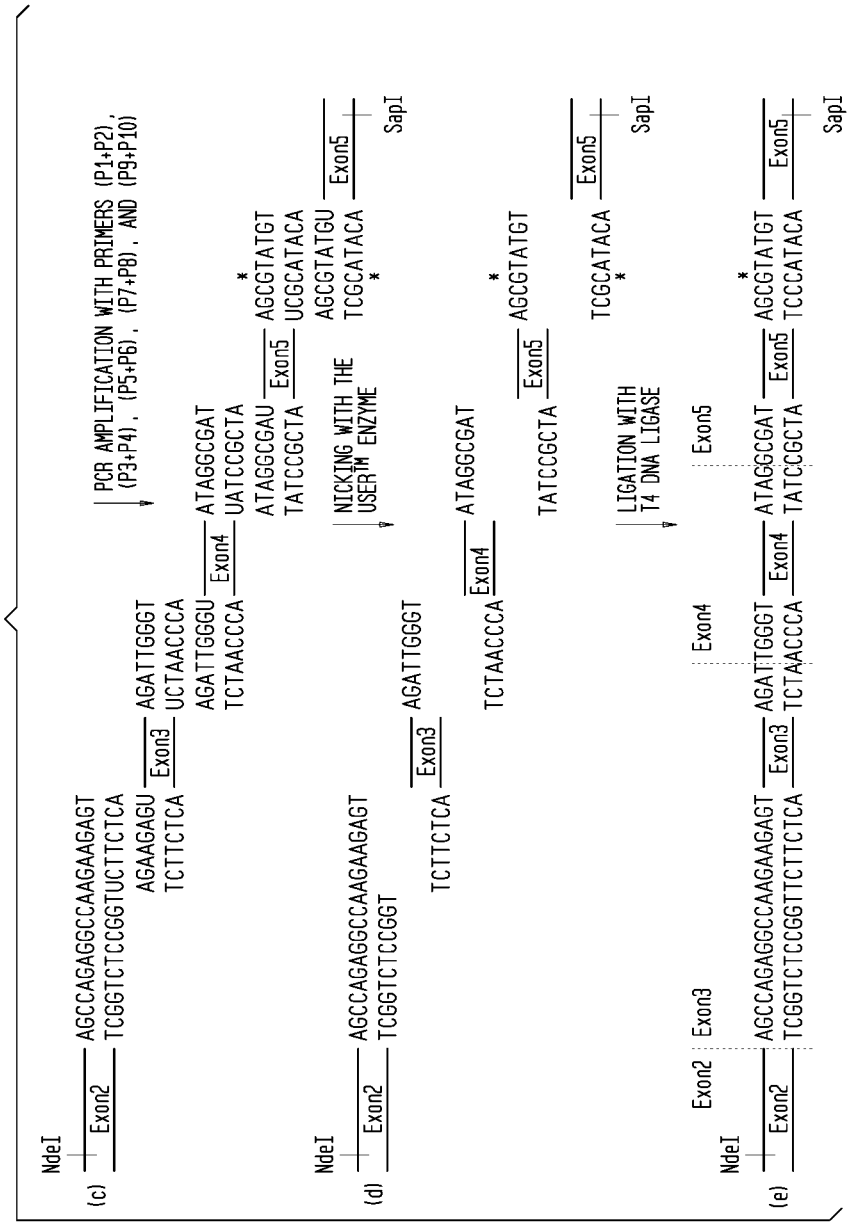

SEQUENCE LISTING

<160> NUMBER OF SEQ ID NOS: 34

<210> SEQ ID NO 1
<211> LENGTH: 30
<212> TYPE: DNA
<213> ORGANISM: Unknown
<220> FEATURE:
<223> OTHER INFORMATION: New England Biolabs plasmid pNEB205A

<400> SEQUENCE: 1
gctgagggaa agtctagatg tctcctcagc        30

<210> SEQ ID NO 2
<211> LENGTH: 13
<212> TYPE: DNA
<213> ORGANISM: unknown
<220> FEATURE:
<223> OTHER INFORMATION: New England Biolabs plasmid pNEB205A cleaved
      with XbaI and nicked with N.BbvCIB -continued

<400> SEQUENCE: 2
gctgagggaa agt                                                    13

<210> SEQ ID NO 3
<211> LENGTH: 32
<212> TYPE: DNA
<213> ORGANISM: unknown
<220> FEATURE:
<223> OTHER INFORMATION: New England Biolabs plasmid pNEB200A

<400> SEQUENCE: 3
acgagactct agaggatcct ctagagtctg gt                               32

<210> SEQ ID NO 4
<211> LENGTH: 41
<212> TYPE: DNA
<213> ORGANISM: unknown
<220> FEATURE:
<223> OTHER INFORMATION: New England Biolabs plasmid pNEB210A

<400> SEQUENCE: 4
gctgaggggg ggatcctttt cattctagat gtctcctcag c                     41

<210> SEQ ID NO 5
<211> LENGTH: 11
<212> TYPE: DNA
<213> ORGANISM: unknown
<220> FEATURE:
<223> OTHER INFORMATION: New England Biolabs plasmid pNEB210A cleaved
      with BamHI and XbaI and nicked with N.BbvCIB

<400> SEQUENCE: 5 gctgagggg g                                                       11

<210> SEQ ID NO 6
<211> LENGTH: 39
<212> TYPE: DNA
<213> ORGANISM: unknown
<220> FEATURE:
<223> OTHER INFORMATION: New England Biolabs plasmid pUC-TT

<400> SEQUENCE: 6
gctgaggggg ggatcctttt catggatccc ccctcagc                         39

<210> SEQ ID NO 7
<211> LENGTH: 11
<212> TYPE: DNA
<213> ORGANISM: unknown
<220> FEATURE:
<223> OTHER INFORMATION: New England Biolabs plasmid pUC-TT cleaved with
      BamHI and nicked with N.BbvCIB

<400> SEQUENCE: 7 gctgagggg g                                                       11

<210> SEQ ID NO 8
<211> LENGTH: 34
<212> TYPE: DNA
<213> ORGANISM: unknown
<220> FEATURE:
<223> OTHER INFORMATION: synthesized chemically
<220> FEATURE:
<221> NAME/KEY: misc_feature
<222> LOCATION: (16)..(16)
<223> OTHER INFORMATION: N = deoxyuridine

```
<400> SEQUENCE: 8
gatttcattt ttattnataa ctttacttat attg                              34

<210> SEQ ID NO 9
<211> LENGTH: 18
<212> TYPE: DNA
<213> ORGANISM: unknown
<220> FEATURE:
<223> OTHER INFORMATION: synthetic left primer
<220> FEATURE:
<221> NAME/KEY: misc_feature
<222> LOCATION: (8)..(8)
<223> OTHER INFORMATION: N = deoxyuridine
<220> FEATURE:
<221> NAME/KEY: misc_feature
<222> LOCATION: (12)..(18)
<223> OTHER INFORMATION: N = any nucleotide

<400> SEQUENCE: 9
ggagacanat gnnnnnnn                                                18

<210> SEQ ID NO 10
<211> LENGTH: 19
<212> TYPE: DNA
<213> ORGANISM: unknown
<220> FEATURE:
<223> OTHER INFORMATION: synthetic right primer
<220> FEATURE:
<221> NAME/KEY: misc_feature
<222> LOCATION: (8)..(8)
<223> OTHER INFORMATION: N = deoxyuridine
<220> FEATURE:
<221> NAME/KEY: misc_feature
<222> LOCATION: (9)..(19)
<223> OTHER INFORMATION: N = any nucleotide

<400> SEQUENCE: 10
gggaaagnnn nnnnnnnn                                                19

<210> SEQ ID NO 11
<211> LENGTH: 11
<212> TYPE: DNA
<213> ORGANISM: unknown
<220> FEATURE:
<223> OTHER INFORMATION: synthetic left primer
<220> FEATURE:
<221> NAME/KEY: misc_feature
<222> LOCATION: (8)..(8)
<223> OTHER INFORMATION: N = deoxyuridine
<220> FEATURE:
<221> NAME/KEY: misc_feature
<222> LOCATION: (9)..(11)
<223> OTHER INFORMATION: N = any nucleotide

<400> SEQUENCE: 11
ggagacannn n                                                       11

<210> SEQ ID NO 12
<211> LENGTH: 101
<212> TYPE: DNA
<213> ORGANISM: unknown
<220> FEATURE:
<223> OTHER INFORMATION: New England Biolabs plasmid pNEB205A

<400> SEQUENCE: 12
agtgaattcg agctcaggcg cgccttaatt aagctgaggg aaagtctaga tgtctcctca   60
gcgtttaaac cctgcaggaa gcttggcgta atcatggtca t                     101
```

```
<210> SEQ ID NO 13
<211> LENGTH: 45
<212> TYPE: DNA
<213> ORGANISM: unknown
<220> FEATURE:
<223> OTHER INFORMATION: New England Biolabs plasmid pNEB205A cleaved
      with XbaI and nicked with N.BbvCIB

<400> SEQUENCE: 13
agtgaattcg agctcaggcg cgccttaatt aagctgaggg aaagt              45

<210> SEQ ID NO 14
<211> LENGTH: 44
<212> TYPE: DNA
<213> ORGANISM: unknown
<220> FEATURE:
<223> OTHER INFORMATION: New England Biolabs plasmid pNEB205A cleaved
      with XbaI and nicked with N.BbvCIB

<400> SEQUENCE: 14
tcagcgttta aaccctgcag gaagcttggc gtaatcatgg tcat               44

<210> SEQ ID NO 15
<211> LENGTH: 12
<212> TYPE: DNA
<213> ORGANISM: unknown
<220> FEATURE:
<223> OTHER INFORMATION: Synthetic Primer P1
<220> FEATURE:
<221> NAME/KEY: misc_feature
<222> LOCATION: (9)..(9)
<223> OTHER INFORMATION: n = deoxyuridine

<400> SEQUENCE: 15
aaatcagcnt tt                                                  12

<210> SEQ ID NO 16
<211> LENGTH: 12
<212> TYPE: DNA
<213> ORGANISM: unknown
<220> FEATURE:
<223> OTHER INFORMATION: wild-type hincIIR gene

<400> SEQUENCE: 16
aaatcagctc aa                                                  12

<210> SEQ ID NO 17
<211> LENGTH: 12
<212> TYPE: DNA
<213> ORGANISM: unknown
<220> FEATURE:
<223> OTHER INFORMATION: mutated hincIIR gene
<220> FEATURE:
<221> NAME/KEY: misc_feature
<222> LOCATION: (9)..(9)
<223> OTHER INFORMATION: N = deoxyuridine

<400> SEQUENCE: 17
aaatcagcnt tt                                                  12

<210> SEQ ID NO 18
<211> LENGTH: 12
<212> TYPE: DNA
<213> ORGANISM: unknown
<220> FEATURE:
<223> OTHER INFORMATION: mutated hincIIR gene

<400> SEQUENCE: 18
aaatcagctt tt                                                  12
```

```
<210> SEQ ID NO 19
<211> LENGTH: 26
<212> TYPE: DNA
<213> ORGANISM: unknown
<220> FEATURE:
<223> OTHER INFORMATION: plasmid pUC19

<400> SEQUENCE: 19
tgtatttaga aaaataaaca aatagg                                              26

<210> SEQ ID NO 20
<211> LENGTH: 12
<212> TYPE: DNA
<213> ORGANISM: unknown
<220> FEATURE:
<223> OTHER INFORMATION: mutated pUC19

<400> SEQUENCE: 20
tgtacaccta gg                                                             12

<210> SEQ ID NO 21
<211> LENGTH: 11
<212> TYPE: DNA
<213> ORGANISM: unknown
<220> FEATURE:
<223> OTHER INFORMATION: New England Biolabs plasmid pTXB1 joined with
      hincIIR gene

<400> SEQUENCE: 21
acatatgagt t                                                              11

<210> SEQ ID NO 22
<211> LENGTH: 11
<212> TYPE: DNA
<213> ORGANISM: unknown
<220> FEATURE:
<223> OTHER INFORMATION: Synthetic Primer P3
<220> FEATURE:
<221> NAME/KEY: misc_feature
<222> LOCATION: (11)..(11)
<223> OTHER INFORMATION: N = deoxyuridine

<400> SEQUENCE: 22
acatatgagt n                                                              11

<210> SEQ ID NO 23
<211> LENGTH: 20
<212> TYPE: DNA
<213> ORGANISM: unknown
<220> FEATURE:
<223> OTHER INFORMATION: Exon2 joined with 5' terminal sequence of
      Exon3. Exons are from human AP1 endonuclease gene

<400> SEQUENCE: 23
agccagaggc caagaagagt                                                     20

<210> SEQ ID NO 24
<211> LENGTH: 10
<212> TYPE: DNA
<213> ORGANISM: unknown
<220> FEATURE:
<223> OTHER INFORMATION: Synthetic Primer P1
<220> FEATURE:
<221> NAME/KEY: misc_feature
<222> LOCATION: (10)..(10)
<223> OTHER INFORMATION: n = deoxyuridine

<400> SEQUENCE: 24 aaccggcgan                                                                10
```

```
<210> SEQ ID NO 25
<211> LENGTH: 11
<212> TYPE: DNA
<213> ORGANISM: unknown
<220> FEATURE:
<223> OTHER INFORMATION: wild-type 9oNm polymerase gene

<400> SEQUENCE: 25
gtcccggcga t                                                                11

<210> SEQ ID NO 26
<211> LENGTH: 11
<212> TYPE: DNA
<213> ORGANISM: unknown
<220> FEATURE:
<223> OTHER INFORMATION: mutated 9oNm polymerase gene

<400> SEQUENCE: 26
caaccggcga t                                                                11

<210> SEQ ID NO 27
<211> LENGTH: 13
<212> TYPE: DNA
<213> ORGANISM: unknown
<220> FEATURE:
<223> OTHER INFORMATION: Synthetic Primer Pal3-3
<220> FEATURE:
<221> NAME/KEY: misc_feature
<222> LOCATION: (6)..(6)
<223> OTHER INFORMATION: n = 8-oxo-guanine

<400> SEQUENCE: 27
gggggnctaa agc                                                              13

<210> SEQ ID NO 28
<211> LENGTH: 26
<212> TYPE: DNA
<213> ORGANISM: unknown
<220> FEATURE:
<223> OTHER INFORMATION: Synthetic Primer Pal3-1

<400> SEQUENCE: 28
ggaacggcaa ttggccttgc cgtgta                                                26

<210> SEQ ID NO 29
<211> LENGTH: 34
<212> TYPE: DNA
<213> ORGANISM: unknown
<220> FEATURE:
<223> OTHER INFORMATION: Synthetic Primer Pal3-3
<220> FEATURE:
<221> NAME/KEY: misc_feature
<222> LOCATION: (6)..(6)
<223> OTHER INFORMATION: n = 8-oxo-guanine

<400> SEQUENCE: 29
gggggnctaa agcctgcccc ttaaccaaac gtta                                       34

<210> SEQ ID NO 30
<211> LENGTH: 20
<212> TYPE: DNA
<213> ORGANISM: unknown
<220> FEATURE:
<223> OTHER INFORMATION: Synthetic Primer GG-2
<220> FEATURE:
<221> NAME/KEY: misc_feature
<222> LOCATION: (6)..(6)
<223> OTHER INFORMATION: n = 8-oxo-guanine
```

```
<220> FEATURE:
<221> NAME/KEY: misc_feature
<222> LOCATION: (19)..(19)
<223> OTHER INFORMATION: h = A, T or C
<220> FEATURE:
<221> NAME/KEY: misc_feature
<222> LOCATION: (20)..(20)
<223> OTHER INFORMATION: n = a, t, c or g

<400> SEQUENCE: 30
gggggngggg ggggggghn                                           20

<210> SEQ ID NO 31
<211> LENGTH: 24
<212> TYPE: DNA
<213> ORGANISM: unknown
<220> FEATURE:
<223> OTHER INFORMATION: Synthetic Sequencing Primer

<400> SEQUENCE: 31
cgccagggtt ttcccagtca cgac                                     24

<210> SEQ ID NO 32
<211> LENGTH: 24
<212> TYPE: DNA
<213> ORGANISM: unknown
<220> FEATURE:
<223> OTHER INFORMATION: Synthetic Sequencing Primer

<400> SEQUENCE: 32
agcggataac aatttcacac agga                                     24

<210> SEQ ID NO 33
<211> LENGTH: 31
<212> TYPE: DNA
<213> ORGANISM: unknown
<220> FEATURE:
<223> OTHER INFORMATION: Synthetic Left Primer
<220> FEATURE:
<221> NAME/KEY: misc_feature
<222> LOCATION: (8)..(8)
<223> OTHER INFORMATION: n = deoxyuridine

<400> SEQUENCE: 33
ggagacancg gatccatacc tgtgacggaa g                             31

<210> SEQ ID NO 34
<211> LENGTH: 31
<212> TYPE: DNA
<213> ORGANISM: unknown
<220> FEATURE:
<223> OTHER INFORMATION: Synthetic Right Primer
<220> FEATURE:
<221> NAME/KEY: misc_feature
<222> LOCATION: (8)..(8)
<223> OTHER INFORMATION: n = deoxyuridine

<400> SEQUENCE: 34
gggaaagngg atccaggcgt ttaagggcac c                             31
```

METHODS AND COMPOSITIONS FOR DNA MANIPULATION

CROSS REFERENCE

This Application is a continuation of U.S. application Ser. No. 12/192,503 filed Aug. 15, 2008 (now abandoned), which is a divisional application of U.S. application Ser. No. 10/407,637 filed Apr. 4, 2003, now U.S. Pat. No. 7,435,572 issued Oct. 14, 2008, which claims priority from U.S. Provisional Application Ser. No. 60/372,352 filed Apr. 12, 2002, U.S. Provisional Application Ser. No. 60/372,675 filed Apr. 15, 2002 and U.S. Provisional Application Ser. No. 60/421,010 filed Oct. 24, 2002, all of which are herein incorporated by reference.

TECHNICAL FIELD AND BACKGROUND OF THE INVENTION

The present invention relates to compositions and methods for cloning and/or manipulating target DNA molecules at a desired sequence in a single experimental format.

In the prior art, methods for manipulation and cloning of DNA include: amplification of DNA by Polymerase Chain Reaction (PCR); cleavage of DNA with restriction endonucleases; and ligation to create recombinant molecules. Limitations of these techniques include: lack of suitable restriction sites in DNA which creates experimental difficulties in accessing a desired location of the DNA sequence for a particular manipulation; poor yield of vector compatible molecules which arises from the template-independent terminal transferase activity of polymerase which introduces a non-template nucleotide at the 3'-termini of amplified products (Clark, *Nucl. Acid. Res.*, 16:9677-9686 (1988)); and incompatibility of the termini of the amplified fragments with termini of recipient molecules thereby preventing efficient insertion of the fragments into vectors or fusion of two or more PCR products to one another. Addition of the 3' nucleotide as a result of terminal transferase activity of the polymerase may be overcome by end polishing of PCR products using a polymerase with 3' to 5' exonuclease activity (Hemsley, et al., *Nucl. Acid. Res.*, 17:6545-6551 (1989)). Alternatively, specially prepared vectors that carry 3'-T overhangs may be used to clone PCR products carrying non-template adenine at the 3' ends (Marchuk, et al. *Nucl. Acid. Res.*, 19:1154 (1990)). However, both the blunt-end insertion and the T/A overhang insertion are inefficient and the above methods do not permit control over the orientation of the inserted fragment in the vector.

Efforts to improve the efficiency of blunt-end insertion of a DNA of interest by eliminating the background of self-ligated vector, include performing an insertion into a SmaI-linearized vector in the presence of SmaI restriction endonuclease which will cleave the self-ligated vector molecules at the re-generated SmaI sites (Liu, et al., *BioTechniques*, 12:28-30 (1992)). The PCR-Script Cloning Systems of Stratagene, Ltd. (La Jolla, Calif.) uses the rare-cleavage restriction enzyme SrfI for a similar purpose. The above methods are ineffective if the PCR product includes any internal SmaI or SrfI sites respectively, or if the site is re-generated after the insertion into the vector DNA.

Another cloning methodology involves preparing amplified segments of DNA for which different restriction sites are added to the 5'-ends of the amplification primers so as to incorporate these sites into the PCR products during amplification (Scharf, et al. *Science*, 233:1076-1078 (1986)). The cleavage of PCR product and vector DNA by the same restriction endonuclease produces compatible single-stranded termini that can be joined by DNA ligase. This method has several disadvantages 1) if the restriction site that is introduced into the primer is present somewhere within the PCR product, the internal site will also be cleaved during endonuclease digestion, thus, preventing cloning of full-length PCR products; 2) many restriction endonucleases inefficiently cleave sites close to the end of DNA fragment (Kaufman, et al. *BioTechniques*, 9:304-306 (1992)), therefore it is necessary to add 3-6 additional nucleotides to the 5'-ends of primers to ensure efficient cleavage by a particular restriction endonuclease; 3) many restriction endonucleases are inhibited by particular components in the amplification reaction, for example, some restriction endonucleases are inhibited by single-stranded PCR primers, so an additional PCR product purification step is necessary before restriction endonuclease digestion; and 4) often restriction endonuclease generated termini are self-complementary resulting in side-products during the ligation reaction thus greatly reducing the yield of target product.

To overcome these limitations, several restriction endonuclease-free techniques have been described that allow creation of single-stranded termini on the PCR products. U.S. application Ser. No. 09/738,444 describes the use of nicking endonucleases to create single-stranded extensions that may be used specifically to join fragments with complementary ends.

Single-stranded termini complementary to the AccI and XmaI restriction endonuclease termini were generated by using the 3' to 5' exonuclease activity of T4 DNA Polymerase (Stoker, *Nucl. Acid. Res.*, 18:4290 (1990)). In the presence of only dATP and dTTP, the exonuclease activity is limited to removal of only G and C nucleotides, thus creating the requisite single-stranded termini for sub-cloning into a AccI- and XmaI-cleaved plasmid vector. In technology referred to as Ligation-Independent Cloning of PCR products (LIC-PCR) (Aslanidis, et al., Nucl. Acid. Res., 18:6069-6074 (1990)) target DNA is amplified with primers containing 12 additional nucleotides at their 5' ends that lack cytosine. As a result, the PCR product on the 3' ends is flanked by a 12-nucleotide sequence lacking guanine. Treatment of the PCR product with the 3' to 5' exonuclease associated with T4 DNA Polymerase in the presence of dGTP removes the 3' terminal sequences until the first dGMP residue is reached, thus leaving a 12 nucleotide 5' single-stranded extension. However disadvantages of this technology include the need for a special vector having compatible 12 nucleotide 5' single-stranded extensions for cloning. The preparation of such vectors include amplification of the entire vector with primers containing 12 nucleotide tails complementary to the tails used for amplification of target fragment and subsequently treating the amplified vector with T4 DNA Polymerase to create complementary 12 nucleotide long single-stranded extensions. A modified technique of LIC-PCR has been described, where the specific sequences devoid of particular bases are engineered into plasmid vectors to replace the vector amplification step by a restriction digestion step (Haun, et al. *BioTechniques*, 13:515-518 (1992); Kuijper, et al. *Gene*, 112:147-155 (1992); Cooney, *BioTechniques*, 24:30-33 (1998)).

A disadvantage of the above-described methods is the need to remove leftover dNTP, before subjecting the PCR product to exonuclease treatment. The use of this technology is limited to sequences devoid of at least one nucleotide, and in addition the use of non-specific exonucleases to manipulate DNA may give rise to sequence rearrangements at the position of vector-product junction of recovered recombinant molecules.

Single-stranded overhangs or extensions have been produced during PCR by incorporating the non-base residue, 1,3-propanediol, into primer sequences. This has the effect of terminating DNA synthesis (Kaluz, S. et al. (1994) Nucl. Acid. Res., 22, 4845). During PCR, Taq DNA Polymerase stops at the non-replicable element, leaving a portion of the primer as a single strand. Since 1,3-propanediol also inhibits DNA replication processes in vivo, the repair machinery of the bacterial host has to remove the non-replicable element potentially causing unwanted sequence rearrangements in the recovered recombinant molecules.

Cloning and manipulating genes with the use of a DNA repair enzyme, Uracil DNA Glycosylase (UDG), has been described. (Rashtchian et al. U.S. Pat. No. 5,137,814; Berninger, U.S. Pat. No. 5,229,283; Nisson, et al., *PCR Methods & Applications*, 1:120-123 (1991); Rashtchian, et al., *PCR Methods & Applications*, 2:124-130 (1992); Booth, et al., *Gene*, 146:303-308 (1994); Rashtchian, *Current Biology*, 6:30-36 (1995)) UDG recognizes uracil lesions in single- or double-stranded DNA and cleaves the N-glycosylic bond between the deoxyribose moiety and the base leaving an abasic site. During PCR, Taq DNA Polymerase inserts deoxyadenisine opposite a deoxyuridine (U) lesion. Target DNA and cloning vectors can be amplified with primers at the 5' ends carrying dUMP-containing tails. Subsequent treatment with the UDG glycosylase results in formation of multiple abasic sites on the ends of the amplified product. Strand separation across the modified portion of the amplified product and the vector that contains complementary ends (generated by the same approach) provides a re-annealed recombinant product having protruding single-stranded flaps which should be removed in vivo by the repair machinery of the bacterial host. Cloning of cDNAs by single-primer amplification (SPA) that employs a dU-containing primer has been described in U.S. Pat. No. 5,334,515.

Since UDG does not cleave the phosphodiester backbone, the efficiency of strand separation to a great extent depends on the number of dUMP residues within the 5' ends of PCR products. Hence, at least one third of the 5' tails of the PCR primer should consist of dUMP to achieve efficient strand separation between two strands of DNA duplex (U.S. Pat. No. 5,137,814 and U.S. Pat. No. 5,229,283). Another disadvantage of this method is that the entire plasmid vector must be amplified by PCR to produce the linear vector flanked by the complementary extensions suitable for sub-cloning of the UDG-treated PCR fragments.

UDG glycosylase has also been used to create SacI restriction endonuclease-like cohesive ends on PCR fragments which are suitable for cloning into SacI-linearized vectors (Smith, et al. *PCR Methods & Applications*, 2:328-332 (1992); Watson, et al. *BioTechniques*, 23:858-862 (1997)). However, this technology is very limited, as it allows cloning of PCR amplified product only into a SacI site. Another disadvantage of this method is that SacI-like cohesive termini are self-complementary. Therefore a variety of unwanted side-products are generated upon ligation thus reducing the use of this technology in DNA manipulations other than cloning of PCR products.

A chemical method for creating single-stranded overhangs on PCR products employs PCR primers containing ribonucleotides, such as rUMP or rCMP (Chen, et al. *BioTechniques*, 32:517-520 (2002); Jarell, et al. U.S. Pat. No. 6,358, 712). After amplification, the PCR products are treated with rare-earth metal ions, such as $La^{3+}$ or $Lu^{3+}$ (Chen, et al. *BioTechniques*, 32:517-520 (2002)) or sodium hydroxide (Jarell, et al. U.S. Pat. No. 6,358,712) to hydrolyze the phosphodiester bond between the deoxyribonucleotide and the ribonucleotide. Disadvantages include the high cost of PCR primers and in addition the vector DNA must be prepared by PCR with the use of primers containing ribonucleotides to generate compatible termini suitable for sub-cloning.

Some of the PCR-based sub-cloning techniques described above can also be used for site-specific DNA mutagenesis. However their application is limited to cases in which, it is possible to introduce a specific change without disrupting the rest of the coding sequence. For example, when suitable restriction sites are located in close proximity to the nucleotide sequence targeted for mutation, the PCR-based oligonucleotide-directed site-specific mutagenesis is routinely used to introduce desired mutations into target DNA sequences and the mutated PCR fragment is then introduced in place of the wild-type sequence using restriction endonuclease digestion (Higuchi, et al. *Nucl. Acid. Res.*, 16:7351-7367 (1988)). However, when the appropriate naturally occurring restriction sites are not available, additional experimental procedures must be performed to introduce internal changes.

Another PCR-dependent mutagenesis method uses a "megaprimer". Megaprimers are long, double-stranded DNAs which are often difficult to denature, to anneal and to extend to a full-length product. Consequently, the method has been found to be problematic when the megaprimer is longer than several hundred base pairs (Kammann, et al. *Nucl. Acid. Res.*, 17:5404 (1989); Sarkar, et al. *BioTechniques*, 8:404-407 (1990); Sarkar, et al. *Nucl. Acid. Res.*, 20:4937-4938 (1992); Landt, et al. *Gene*, 96:125-128 (1990); Ling, et al. *Analytical Biochemistry*, 254:157-178 (1997); Smith, et al. *BioTechniques*, 22:438-442 (1997); Colosimo, et al. *BioTechniques*, 26:870-873 (1999)).

Another PCR-dependent site-directed mutagenesis technique referred to as "overlap-extension" PCR has been described (Higuchi, et al. *Nucl. Acid. Res.*, 16:7351-7367 (1988); Ho, et al. *Gene*, 77:51-59 (1989)). Two primary PCR reactions produce two overlapping DNA fragments, both bearing the same mutation introduced via mutagenic primers in the region of the overlap sequence. These fragments are then combined, denatured and re-annealed to generate a hetero-duplex product via the overlapping sequence. In the re-annealed hetero-duplex product, the 3' overlap of each strand serves as a primer for the extension of the complementary strand. The extended full-size fusion is then amplified in a second round of PCR using the outside primers. The overlap-extension method is laborious and inefficient in many practical applications for several reasons: it requires the purification of intermediate PCR product to remove mutagenic primers; it requires two full rounds of PCR, which increases the possibility of introducing the undesired mutations; and the efficiency of annealing heterologous molecules across the overlap region is greatly reduced by the presence of a full-length complementary strand of either fragment.

No existing single PCR-based method for site-directed mutagenesis and cloning appears to solve all of the problems associated with in vitro DNA manipulations. A single strategy for achieving a variety of DNA manipulations, such as linking, adding, deleting or changing nucleotide segments at any desired location of target DNA molecule would be desirable.

SUMMARY OF THE INVENTION

In an embodiment of the invention, a method is provided for generating a single-stranded extension on a polynucleotide molecule where the single-stranded extension has a desired length and sequence composition. The method includes the steps of: inserting a cassette into a polynucleotide molecule at a predetermined location; cleaving the polynucleotide molecule with a nicking endonuclease specific for a nicking site in the cassette and with a restriction endonuclease specific for a restriction site in the cassette; and dissociating the cleaved polynucleotide molecule between the nicking site and the restriction site to generate the single-stranded extension with the desired length and sequence composition.

In addition to the above described method, an additional embodiment of the invention is a cassette wherein the cassette includes a double-stranded DNA having a nicking site located less than about 50 nucleotides from a restriction site, the DNA being capable of insertion into a polynucleotide molecule, wherein the restriction site in the cassette does not occur in the polynucleotide molecule.

In particular examples of the above embodiments, the method includes the use of a cassette, where the cassette contains a nicking site and a restriction site for generating a 3' or 5', left side or right side single-stranded extension; or one restriction site flanked on each side by a nicking site for generating a left side and a right side 3' or 5' single-stranded extension; or two restriction sites positioned between two nicking sites for generating two single-stranded extensions. The sequence between the nicking site and the restriction site determine the length and composition of the single-stranded extension product. The single-stranded extension produced is preferably no longer than about 20 nucleotides. In those examples where two restriction sites are present in a cassette, a spacer sequence may be located between the two restriction sites. The spacer region may be selected according to its coding sequence where it is desirable under certain circumstances that the spacer encode a marker and the polynucleotide molecule into which the cassette is inserted is a recipient molecule which is capable of replicating in a host cell. The spacer sequence provides a means to determine in host cells transformed with a recipient molecule containing an inserted cassette, which recipient molecule contains a cassette and which recipient molecules lack a cassette or contain a defective cassette.

In additional examples of the above embodiment, the cassette may contain a nicking site positioned upstream (left side) or downstream (right side) from the restriction site in the cassette in an orientation suitable for nicking a first of two strands (top strand) or the second of the two strands (bottom strand) with the nicking endonuclease. In cassettes where two nicking sites occur, these are each inversely oriented with respect to each other.

In additional examples of the above embodiment, the recipient molecule may be a vector and the vector may be selected from: pNEB205A, pNEB200A, pNEB210A, and pUC-TT.

In an additional embodiment of the invention, a nicking agent is provided which includes a mixture of two or more enzymes wherein at least one of the enzymes is a DNA glycosylase and at least one of the enzymes is a single-strand cleaving enzyme, wherein the nicking agent is capable of excising a modified nucleotide from a polynucleotide molecule.

In particular examples of the above embodiment, at least one single-stranded cleaving enzyme in the nicking agent generates a 5' phosphate in the polynucleotide molecule after excision of the modified nucleotide. This activity is further exemplified by use of single stranded cleaving enzymes: FPG glycosylase/AP lyase and Endo VIII glycosylase/AP lyase. Alternatively or additionally, the nicking agent may contain at least one single-stranded cleaving enzyme that generates a 3'OH in the polynucleotide molecule after excision of the modified nucleotide using, for example, EndoIV endonuclease.

The modified nucleotide described above may include deoxyuridine (U), 8-oxo-guanine or deoxyinosine. Examples of nicking agents described herein that are capable of excising these modified nucleotides include: for excising deoxyuridine(U)—UDG glycosylase in a mixture with EndoIV endonuclease; UDG glycosylase in a mixture with FPG glycosylase/AP lyase; UDG glycosylase in a mixture with EndoVIII glycosylase/AP lyase; a mixture containing UDG glycosylase, EndoIV endonuclease and EndoVIII glycosylase/AP lysase; for excising 8-oxo-guanine and deoxyuridine (U)—a mixture containing UDG glycosylase, FPG glycosylase/AP lyase and EndoIV endonuclease; or UDG glycosylase in a mixture with FPG glycosylase/AP lyase; and for excising deoxyinosine—AlkA glycosylase in a mixture with EndoVIII glycosylase/Ap lyase or AlkA glycosylase in a mixture with FPG glycosylase/AP lyase. In particular examples, the glycosylase and the single-strand cleaving enzyme are present in the nicking agent in an activity ratio of at least about 2:1.

In an additional embodiment of the invention, a method is provided for generating a single-stranded extension on a polynucleotide molecule, the single-stranded extension having a desired length and composition. The method includes the steps of introducing into the polynucleotide molecule at a specific location, a modified nucleotide; cleaving the polynucleotide molecule at the modified nucleotide with a nicking agent to create a terminal sequence flanked by a nick; and dissociating the terminal sequence to generate the single-stranded extension with the desired length and sequence composition.

In particular examples of the embodiment, the polynucleotide molecule is a product of primer pair dependent DNA amplification of a target molecule. Moreover, each primer in the primer pair may contain the modified nucleotide or alternatively one of the primers in the primer pair may contain the modified nucleotide. The composition of the single-stranded extension on the polynucleotide molecule may be such that it is complementary to a single-stranded extension on a second polynucleotide molecule.

In an additional embodiment of the invention, a method is provided for creating a site-specific mutation in a target molecule. This embodiment includes selecting two pairs of primers for amplifying the target molecule wherein one pair of primers produces one amplification product and the second pair of primers produces a second amplification product. One primer from each primer pair may contain a modified nucleotide and the sequence of such primers complements each other at the 5' end. Optionally one or both of these primers contain a mutation in the complementary or in a non-complementary 5' sequence where complementation is determined with respect to the target molecule. The target molecule is then amplified using the two primer pairs to form two polynucleotide molecules. These polynucleotide molecules are nicked at the modified nucleotide with a nicking agent. The polynucleotide molecules are then dissociated between the nick and the 5' end to produce 3' single-stranded extensions on the two polynucleotide molecules that are complementary to each other. The two polynucleotide molecules are permitted to reassociate through the complementary single-stranded extensions to form a target molecule having a site specific mutation.

In an example of the above embodiment, the sequence at the 5' end of the primers adjacent to the modified nucleotide may be characterized as non-complementary to the target molecule. In another example, one primer from each of the two primer pairs has a modified nucleotide positioned between a priming sequence and a 5' terminal region, wherein the priming sequence is complementary to the target molecule and wherein the 5' terminal regions of the primers adjacent to the modified nucleotide are complementary to each other.

Additionally, the modified nucleotide on at least one primer may be positioned at a junction between the priming sequence and the 5' terminal region. Alternatively, the modified nucleotide on at least one primer may be positioned between the 5' sequence and an insertion sequence wherein the insertion sequence is adjacent to the priming sequence. In an additional configuration, the priming sequence on each of the primers may complement sequences on the target molecule which are separated by an intervening sequence.

The site-specific mutation referred to above may be an alteration in one or more nucleotides or an inserted nucleotide sequence.

In an additional embodiment of the invention, an oligonucleotide suitable for priming a DNA template is provided having a 5' sequence selected from GGAGACAU, GGGAAAGU, ACGAGACU, ACCAGACU and GGGGG(8-oxo-G) adjacent to a sequence identical to the 5' end of the DNA template.

In an additional embodiment of the invention, a method is provided for joining a plurality of linear polynucleotide molecules to form a single molecule. The method includes forming a single-stranded extension on one or both ends of each of the plurality of polynucleotide molecule using a cassette as described above. The product includes at least one single-stranded extension on one polynucleotide molecule that is complementary to a single-stranded extension on another polynucleotide molecule. The plurality of polynucleotide molecules can then be associated to form the single molecule.

In an additional embodiment, a method is provided for joining a plurality of linear polynucleotide molecules to form a single molecule. The method includes forming a single-stranded extension on one or both ends of a plurality of polynucleotide molecules using primer-dependent amplification described above. The product includes at least one single-stranded extension on one polynucleotide molecule that is complementary to a single-stranded extension on another polynucleotide molecule. The plurality of polynucleotide molecules can then associate to form the single molecule.

In an additional embodiment of the invention, a method for inserting a target molecule into a recipient molecule is provided. The method includes forming a first and a second-single-stranded extension on the ends of the recipient molecule after cleavage of sites in a cassette. Single-stranded extensions are formed on a target molecule by primer-dependent amplification. The single-stranded extension on one end of the target molecule is complementary to the first single-stranded extension on the recipient molecule; and on the other end of the target molecule is complementary to the second single-strand extension on the recipient molecule, so that the target molecule and the recipient molecule associate to form a single target molecule.

In particular examples of the above embodiments, the target molecule may be a product of joining a plurality of polynucleotide molecules, or may represent individual conserved DNA domains such as Exons. In addition, the first- and the second single-stranded extensions on the recipient molecule may have the same or different sequence.

In an embodiment of the present invention, a kit is provided that includes a nicking agent and a linearized vector. the kit may further include a DNA polymerase, a T4 DNA ligase or ast least one sequencing primer.

In an embodiment of the present invention, a host cell is provided which contains a recipient molecule into which a target molecule has been inserted via single-stranded extensions created according to the above embodiments.

(a) inserted into a polynucleotide molecule is a cassette, having boundaries (13), and containing site A recognized by nicking endonuclease A which nicks within site A on one strand as indicated by the arrow and site B located downstream of site A recognized by restriction endonuclease B, which cleaves both strands as indicated by the arrows;

(b) the polynucleotide molecule containing the cassette showing breaks in the phosphodiester bond backbone from cleavage with nicking endonuclease A and restriction endonuclease B;

(c) the products of dissociation (1), (2) and (3) where (1) is the left-side of the cleaved polynucleotide molecule flanked by a 3' single-stranded extension of the desired length and composition.

Figure 2:
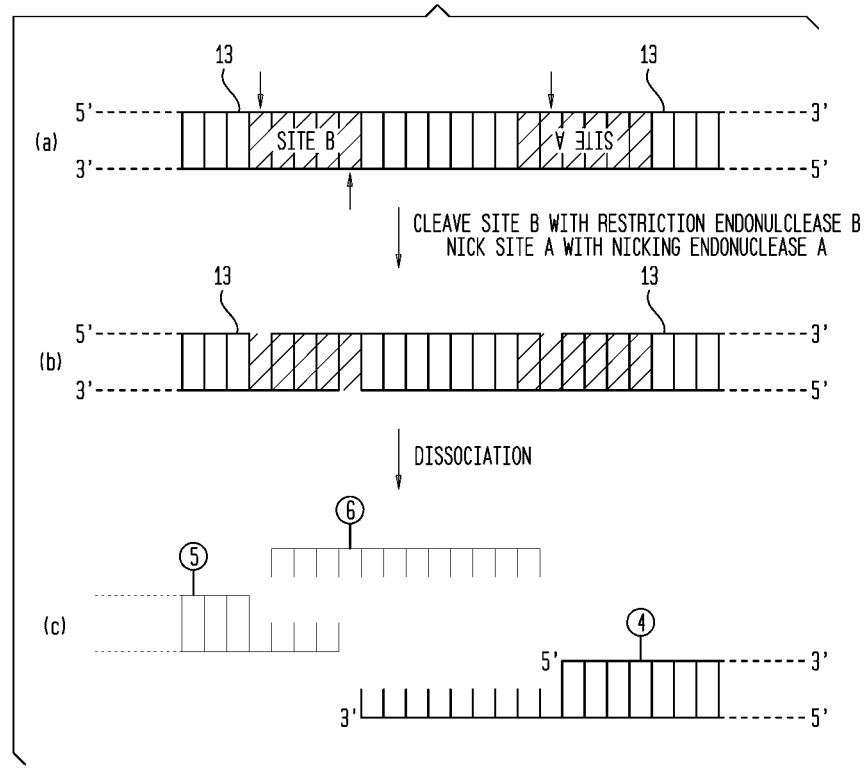

FIG. 2 shows how a 3' single-stranded extension of desired length and composition can be generated on the right-side of a cleaved polynucleotide molecule;

(a) inserted into a polynucleotide molecule is a cassette, having boundaries (13), containing a site A which is inversely oriented to and located downstream of site B;

(b) the polynucleotide molecule containing the cassette showing breaks in the phosphodiester backbone from cleavage with nicking endonuclease A and restriction endonuclease B;

(c) the products of dissociation (4), (5) and (6) where (4) is the right-side of the cleaved polynucleotide molecule flanked with a 3' single-stranded extension of a desired length and composition.

Figure 3:
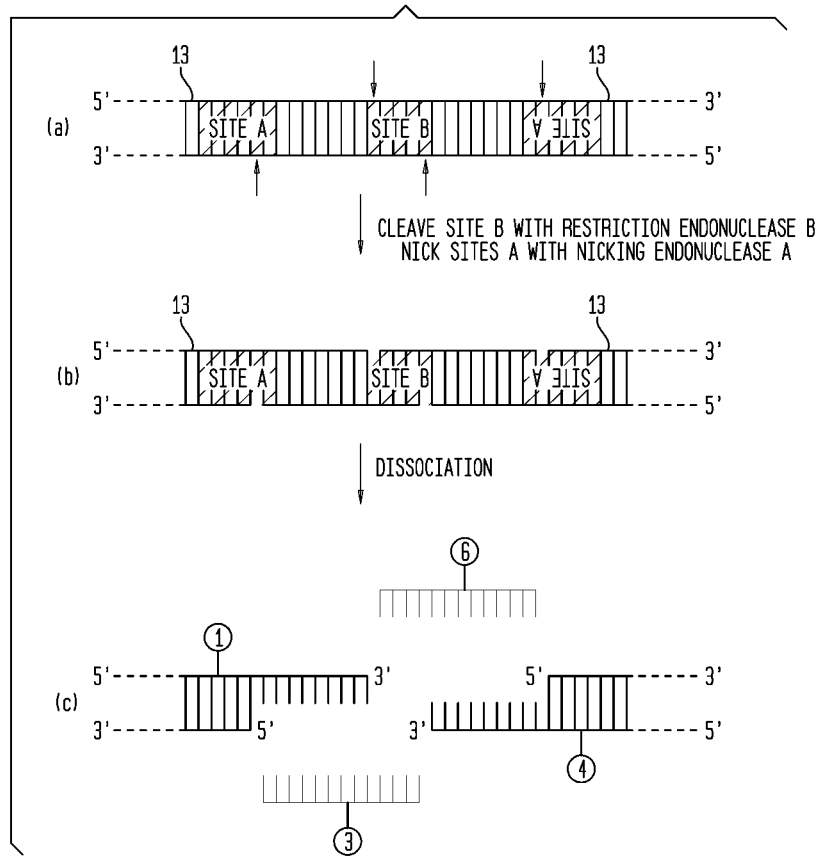

FIG. 3 shows how 3' single-stranded extensions of desired length and composition can be obtained on both the left-side and the right-side of a cleaved polynucleotide molecule:

(a) inserted into a polynucleotide molecule is a cassette, having boundaries (13), containing two nicking sites A inversely oriented with respect to each other and located on either side of a single restriction endonuclease site B;

(b) the polynucleotide molecule containing the cassette showing breaks in the phosphodiester backbone from cleavage with nicking endonuclease A and restriction endonuclease B;

(c) the products of dissociation (1), (3), (4) and (6) where (1) and (4) have 3' single-stranded extensions of the desired length and nucleotide composition.

Figure 4:
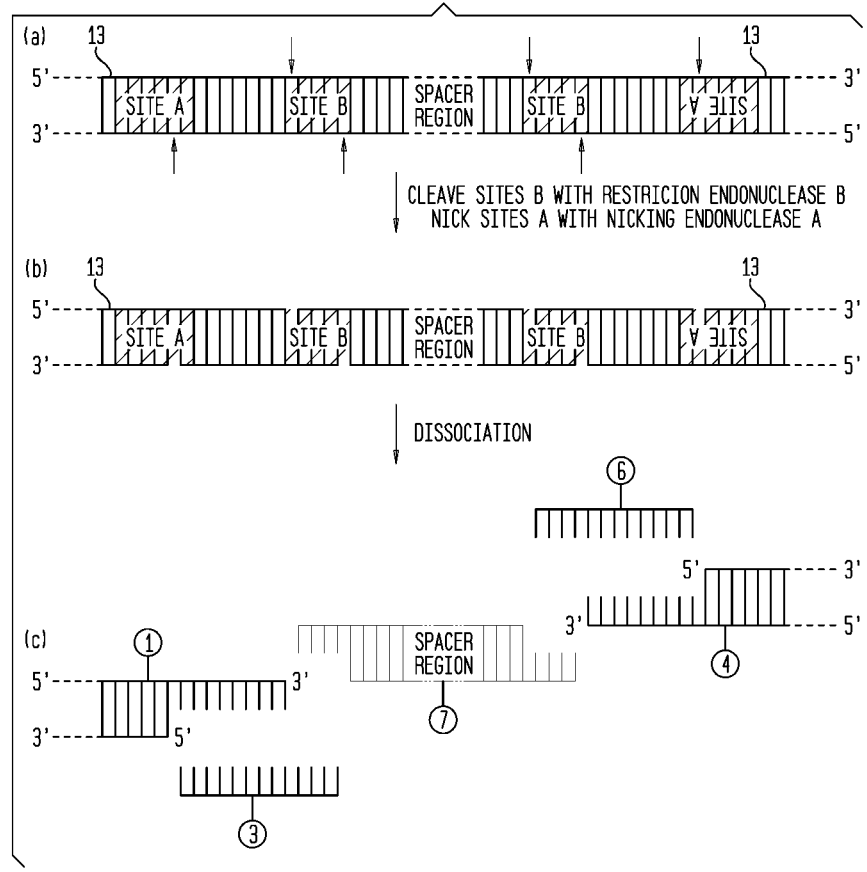

FIG. 4 shows how a 3' single-stranded extension can be obtained on both left-side and right-side of a cleaved polynucleotide molecule:

(a) inserted into the polynucleotide molecule is a cassette, having boundaries (13), and containing two inversely oriented nicking sites A flanking two restriction sites B. Between the two restriction sites, is a spacer region of any desired length (shown by the dotted line);

(b) the polynucleotide molecule containing the cassette showing breaks in the phosphodiester backbone from cleavage with nicking endonuclease A and restriction endonuclease B;

(c) the products of dissociation (1), (3), (4), (6) and (7) where (1) and (4) have 3' single-stranded extensions of the desired length and nucleotide composition and (7) is the spacer region.

Figure 5:
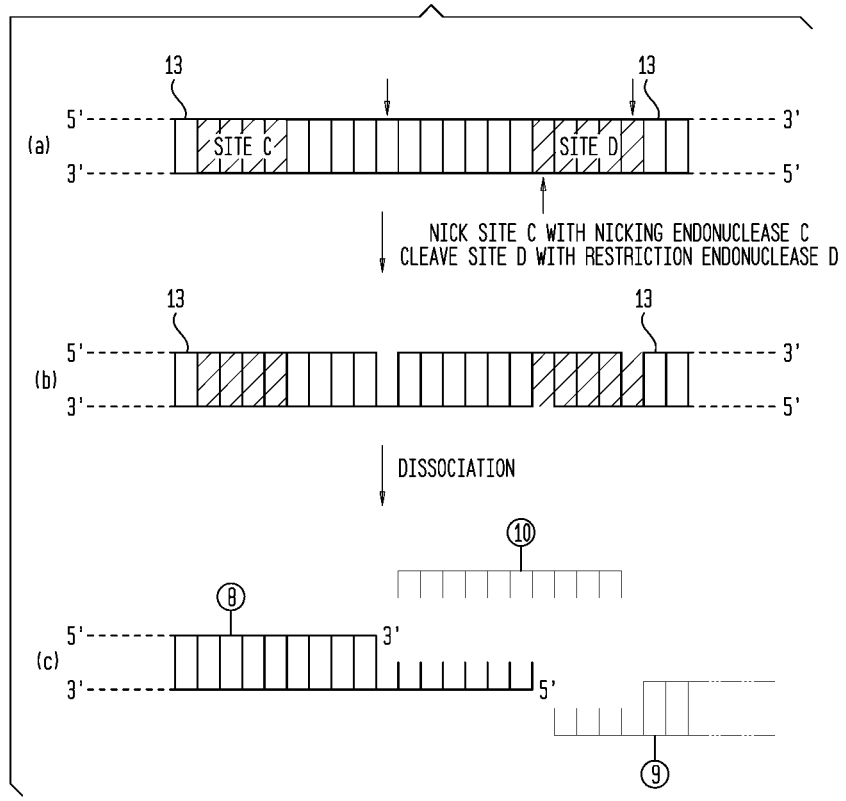

FIG. 5 shows how a 5' single-stranded extension of desired length and composition can be generated on the left-side of a cleaved polynucleotide molecule:

(a) inserted into the double-stranded polynucleotide molecule is a cassette, having boundaries (13), containing a site C and a site D, where site C is recognized by a nicking endonuclease C which nicks outside site C as indicated by an arrow. The site D located downstream of site C is recognized by restriction endonuclease D, which cleaves both strands as indicated by the arrows;

(b) the polynucleotide molecule containing the cassette showing breaks in the phosphodiester backbone from cleavage with nicking endonuclease C and restriction endonuclease D;

(c) the products of dissociation (8), (9) and (10) where (8) is a left-side of the cleaved polynucleotide molecule flanked by a 5' single-stranded extension of the desired length and composition.

Figure 6:
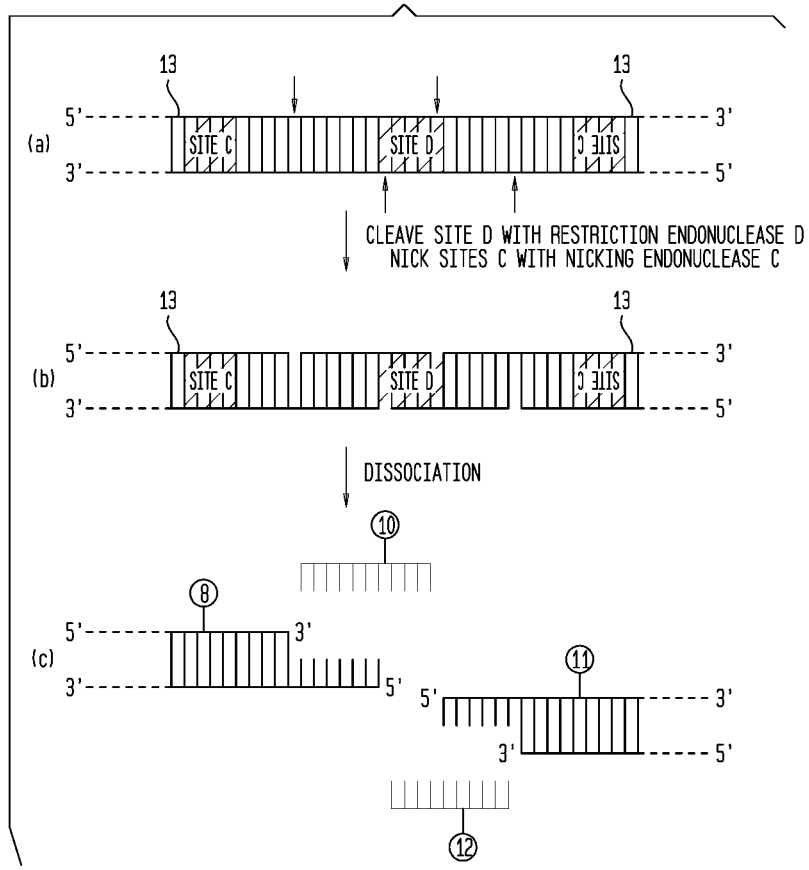

FIG. 6 shows how 5' single-stranded extensions can be obtained on both left-side and right-side of a cleaved polynucleotide molecule:

(a) inserted into the double-stranded polynucleotide molecule is a cassette, having boundaries (13), and containing two nicking sites C inversely oriented with respect to each other and located on either side of a single restriction site D.

(b) the polynucleotide molecule containing the cassette showing breaks in the phosphodiester backbone from cleavage with nicking endonuclease C and restriction endonuclease D;

(c) the products of dissociation (8), (10), (11) and (12) where (8) and (11) have 5' single-stranded extensions of the desired length and nucleotide composition.

Figure 7:
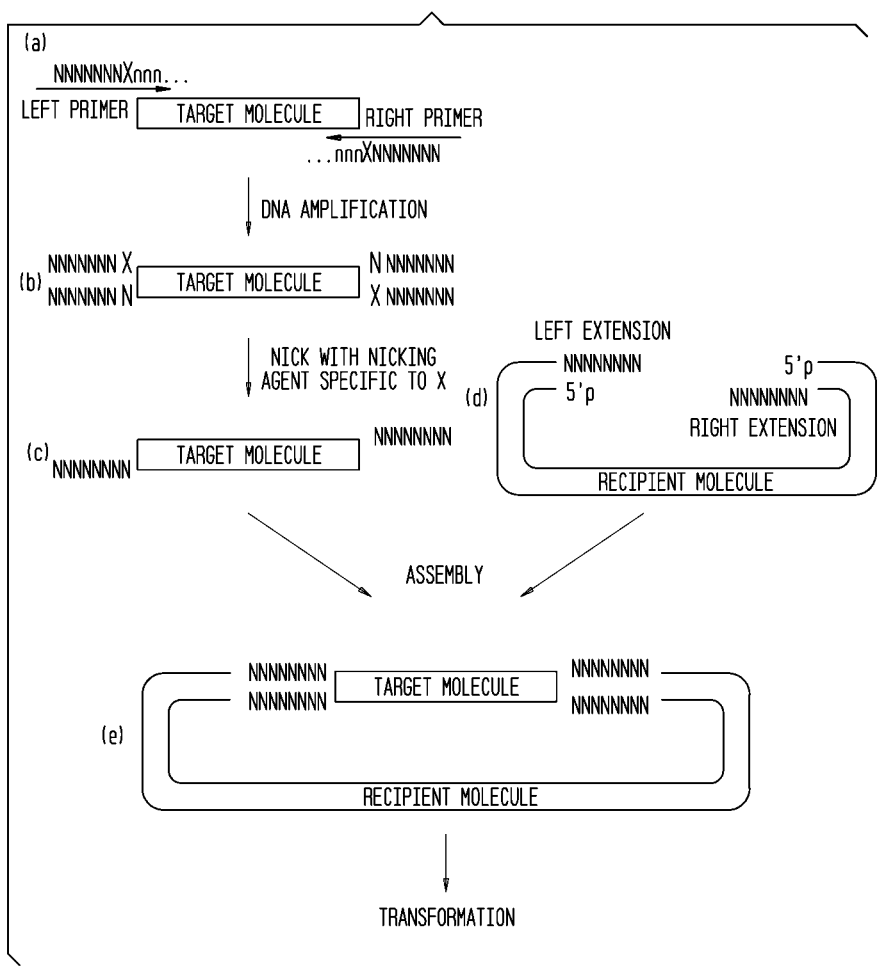

FIG. 7 shows how a target molecule can be inserted into a recipient molecule in a predetermined orientation:

(a) a left and a right primer is shown where each primer at the 5' end is characterized by: a plurality of nucleotides (N) in which N corresponds to any of A, T, G or C of a nucleotide sequence that is not complementary to a target molecule sequence, but is identical to the corresponding left or right 3' single-stranded extension on the linearized recipient molecule except for the nucleotide "X", which in a primer sequence replaces the terminal 3' nucleotide on the left and right end of the recipient molecule, and is the target for a nicking agent; and a plurality of nucleotides (n) that hybridize to the nucleotides on the complementary strand of the target molecule;

(b) the product of DNA amplification corresponding to the entire sequence of the left and right primers and the target molecule;

(c) the target molecule flanked by 3' single-stranded extensions produced after treatment of amplified DNA with a nicking agent specific to X.

(d) the recipient molecule having 3' single-stranded extensions which are complementary to the 3' single-stranded extensions on the target molecule of (c);

(e) the recombinant product resulting from combining the target and recipient molecules of (c) and (d).

Figure 8:
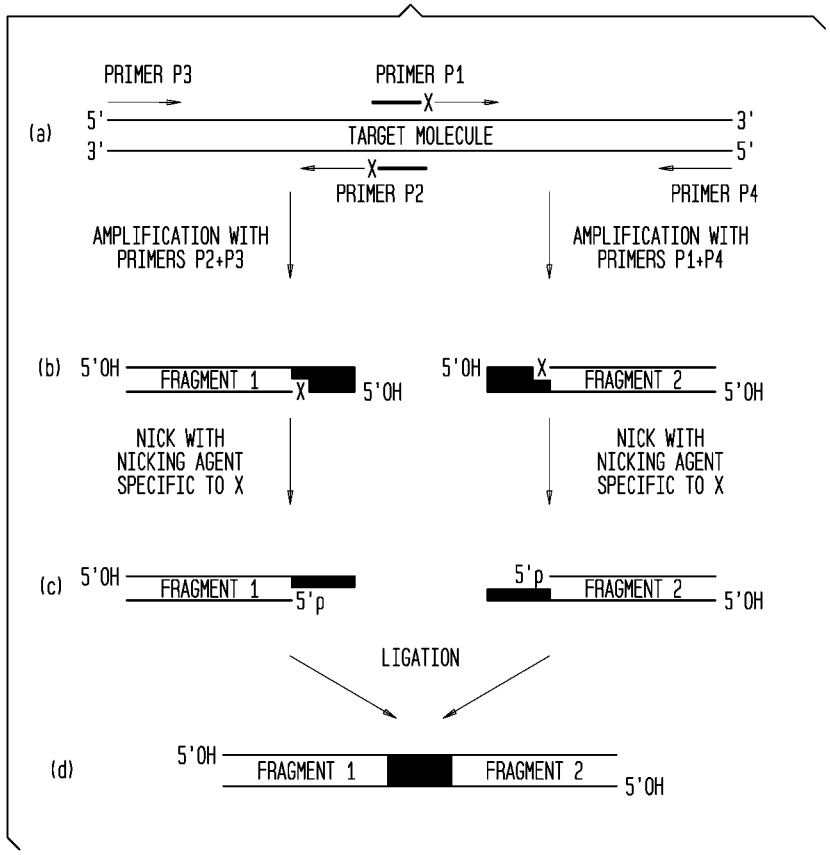

FIG. 8 shows how complementary 3' single-stranded extensions can be generated at the desired locations in a target molecule:

(a) design of primer pairs P2/P3 and P1/P4 showing their location in the target molecule, where Primers P1 and P2 overlap each other by a pre-selected nucleotide sequence shown as a bold line, the pre-selected nucleotide sequence including a modified nucleotide X at the 3' end of the overlap;

(b) the amplification products referred to as Fragments 1 and 2 amplified using primer pairs P2/P3 and P1/P4 respectively and showing the common overlap region (in black) with the presence of modified nucleotide on the opposite strands in Fragments 1 and 2;

(c) the products of dissociation of Fragments 1 and 2 after cleavage with a nicking agent specific to X having 3' single-stranded extensions that are complementary to each other;

(d) Fragments 1 and 2 are re-associated through their complementary 3' single-stranded extensions.

Figure 9A:
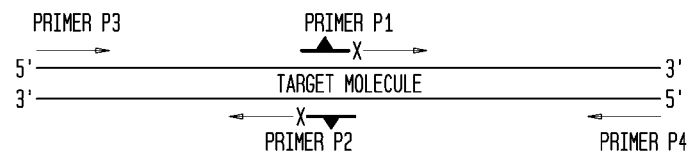
Figure 9B:
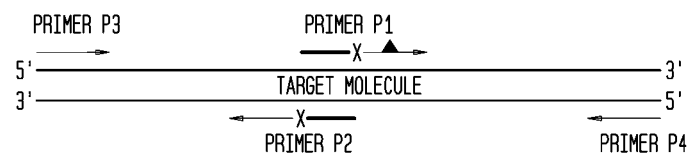

FIGS. 9A and 9B shows how primer pairs (P2/P3 and P1/P4) can be modified to achieve a site-specific mutation in a target molecule. Only the primer design step is shown. These primers can be used according to FIG. 8 (b) to (d). X is the modified nucleotide:

FIG. 9A Primer design includes introducing a mutation (black triangle) in overlapping sequences of both P1 and P2 primers (shown in bold) such that when these primers are used in the generation of Fragments 1 and 2 (FIG. 8, (b)) both amplified fragments will carry the mutation at the same position of the common overlap region;

FIG. 9B Primer design includes introducing a mutation downstream of X in P1 only (black triangle). If P1 and P2 are used in the generation of Fragments 1 and 2 (FIG. 8, (b)) the mutation will be located within Fragment 2 downstream from the overlap region.

Figure 10:
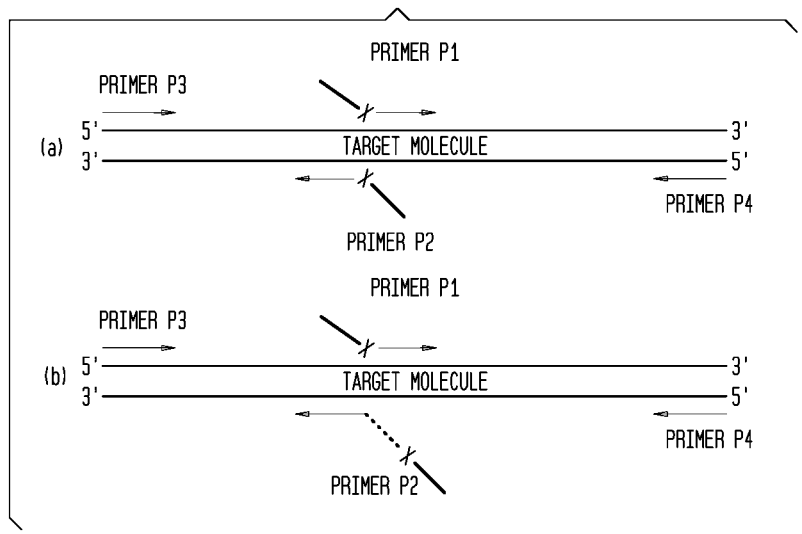

FIG. 10 shows how primer pairs (P2/P3 and P1/P4) can be modified to achieve a nucleotide sequence insertion in a target molecule. Only the primer design step is shown. These primers can be used according to FIG. 8 (b) to (d). The priming sequence (shown as arrows) in both overlapping Primers P1 and P2 starts precisely at the position of the expected insertion. X is a modified nucleotide:

FIG. 10A Primer design includes Primers P1 and P2 having 5' overlapping regions which correspond to an insertion sequence (shown in bold). X is located at the junction between the priming sequence (shown as an arrow) and the insertion sequence.

FIG. 10B Primer design includes a Primer P2 having an entire insertion sequence at its 5' end adjacent to the priming sequence (shown as a dotted line plus a bold line). To create a common overlap, Primer P1 contains the 5' end of the insertion sequence (shown in bold). In P1, X is located at the junction between the priming sequence (shown as an arrow) and the overlap region. In P2, X is located at the junction of the overlap region and the remainder of the insertion sequence.

Figure 11:
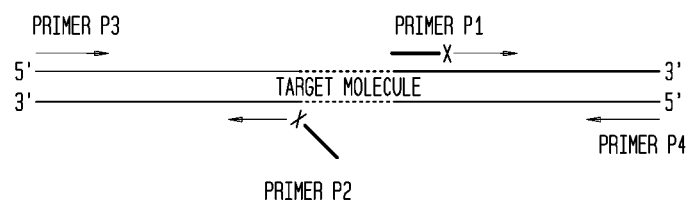

FIG. 11 shows how primer pairs (P2/P3 and P1/P4) can be modified to achieve a nucleotide sequence deletion in a target molecule. Only the primer design step is shown. These primers can be used according to FIG. 8 (b) to (d).

Overlapping Primers P1 and P2 are designed so that priming sequence of each primer starts precisely beyond the targeted deletion region of the target molecule (dotted lines in the target molecule). To generate the common overlap region, an additional nucleotide sequence is included at the 5' end of Primer P2 which is the reverse-complement to the 5' end of P1. The overlapping regions are shown as a bold line. Each primer carries a single modified nucleotide X at the junction between the overlapping region and the priming sequence.

Figure 12:
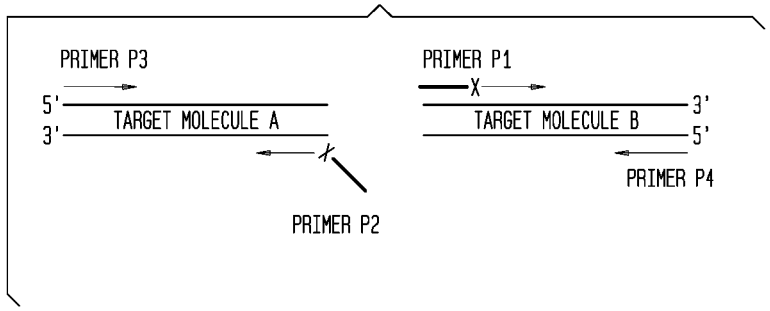

FIG. 12 shows how primer pairs (P2/P3 and P1/P4) can be designed to generate a fusion product from a target molecule A and a target molecule B. Only the primer design step is shown. These primers can be used according to FIG. 8 (b) to (d).

Overlapping Primers P1 and P2 are designed so that each primer anneals to a respective target molecule. To generate the common overlap region, an additional nucleotide sequence is included at the 5' end of Primer P2 which is the reverse-complement to the 5' end of Primer P1. The overlapping regions are shown as a bold line. Each primer carries a single modified nucleotide X at the junction between the overlapping region and the priming sequence.

Figure 13:
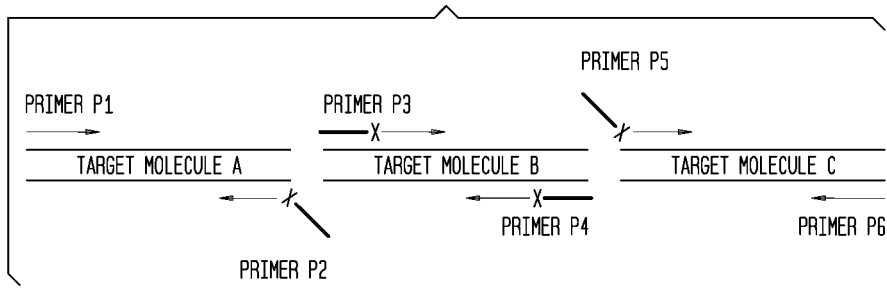

FIG. 13 shows how multiple primer pairs can be designed to achieve assembly of target molecule from the multiple intermediate target molecules following the approach in FIG. 12. For primer pairs P1/P2, P3/P4 and P5/P6 used to amplify intermediate target molecules A, B and C respectively, two overlapping primer pairs, P2/P3, P4/P5 are designed as described in FIG. 12.

Figure 14:
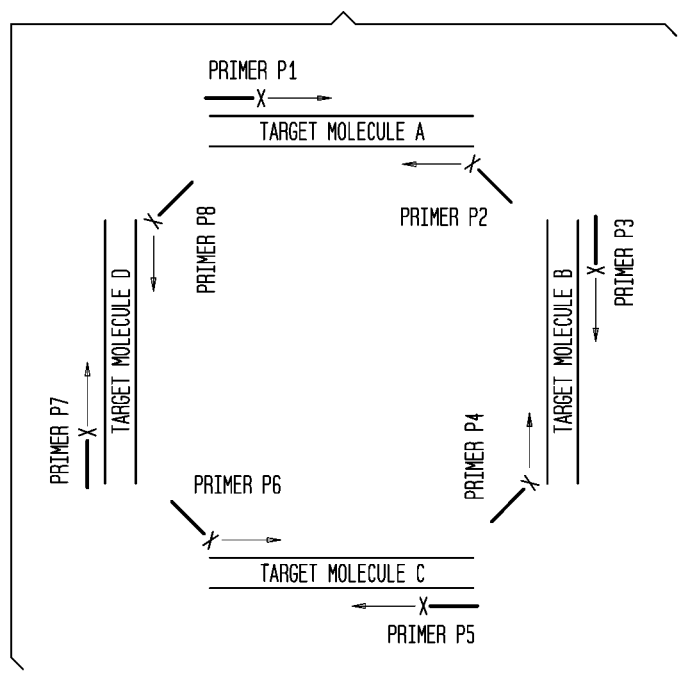

FIG. 14 shows how multiple primer pairs can be designed to achieve assembly of a circular target molecule from multiple intermediate target molecules following the approach in FIG. 12. For primer pairs P1/P2, P3/P4, P5/P6, P7/P8 used to amplify target molecules A, B, C and D respectively, four overlapping primer pairs, P2/P3, P4/P5, P6/P7 and P8/P1, are designed as described in FIG. 12.

Figure 15:
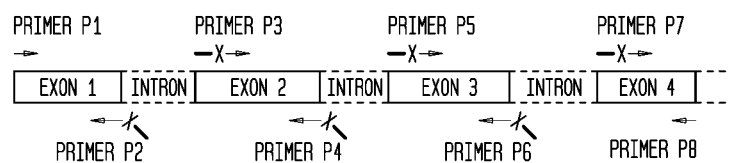

FIG. 15 shows how to generate an eukaryotic gene directly from the genomic DNA instead of making a cDNA by assembling individual Exons using multiple pairs of primers designed as shown in FIGS. 12 and 13. The 5' common overlap region in the primer is shown in bold. The priming sequence is indicated by an arrow.

Figure 16:
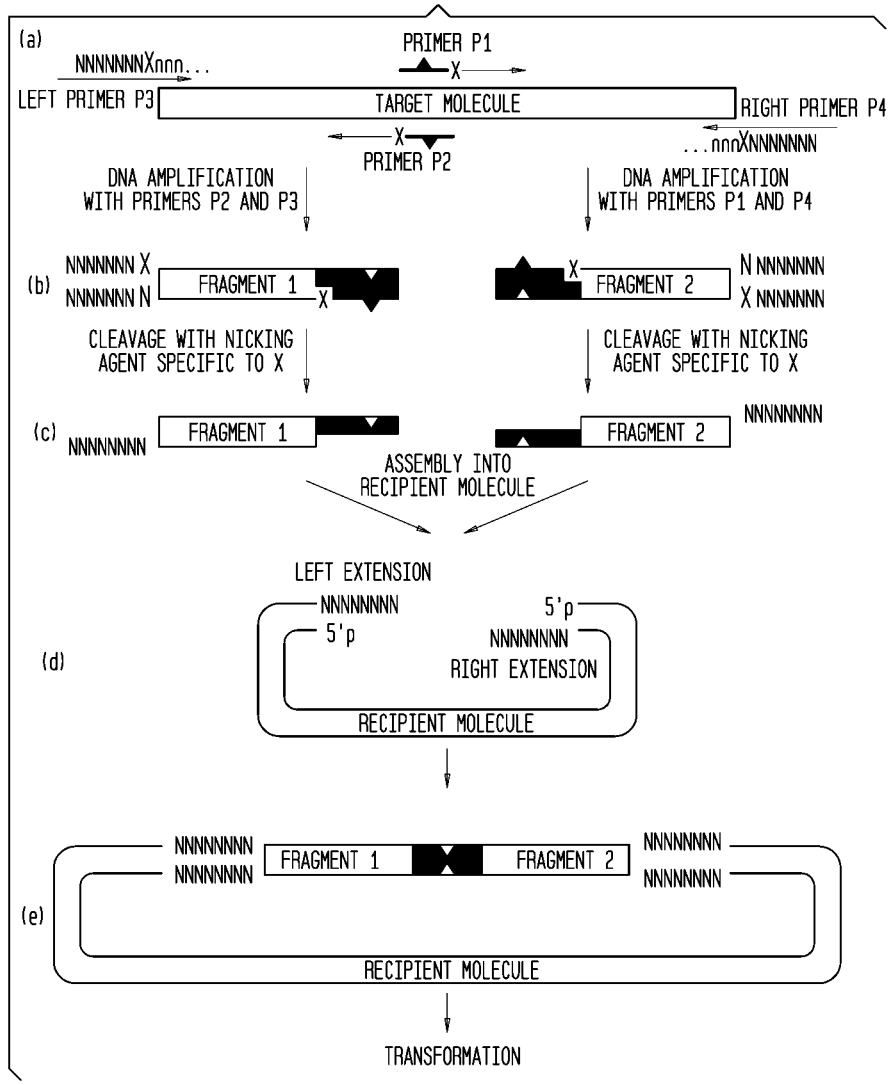

FIG. 16 shows how concurrent manipulation and cloning of target molecule can be achieved:

(a) design of the outside Primers P3 and P4 permits insertion into a recipient molecule, while design of overlapping Primers P1 and P2 permits manipulation of the target molecule. Outside Primers P3 and P4 are designed as described in FIG. 7 (*a*). Overlapping Primers P1 and P2 are designed as described in FIG. 9A. Target DNA is amplified as two overlapping fragments with primer pairs P2/P3 and P1/P4;

(b) the amplification products identified as Fragment 1 and Fragment 2 contain a newly introduced mutation within the common overlap region (black and white triangles);

(c) the dissociation products of Fragments 1 and 2 after cleavage with a nicking agent specific for X, where Fragments 1 and 2 are flanked by 3' single-stranded extensions on both ends. The outside extensions are complementary to the 3' single-stranded extensions on the recipient molecule, while the inside extensions carrying a newly introduced mutation (white triangle) are complementary to each other;

(d) the recipient molecule is flanked by 3' single-stranded extensions complementary to the outside 3' single-stranded extensions of Fragments 1 and 2;

(e) directional assembly of Fragment 1 and 2 into the recipient molecule by means of annealing of complementary single-stranded extensions.

Figure 17:
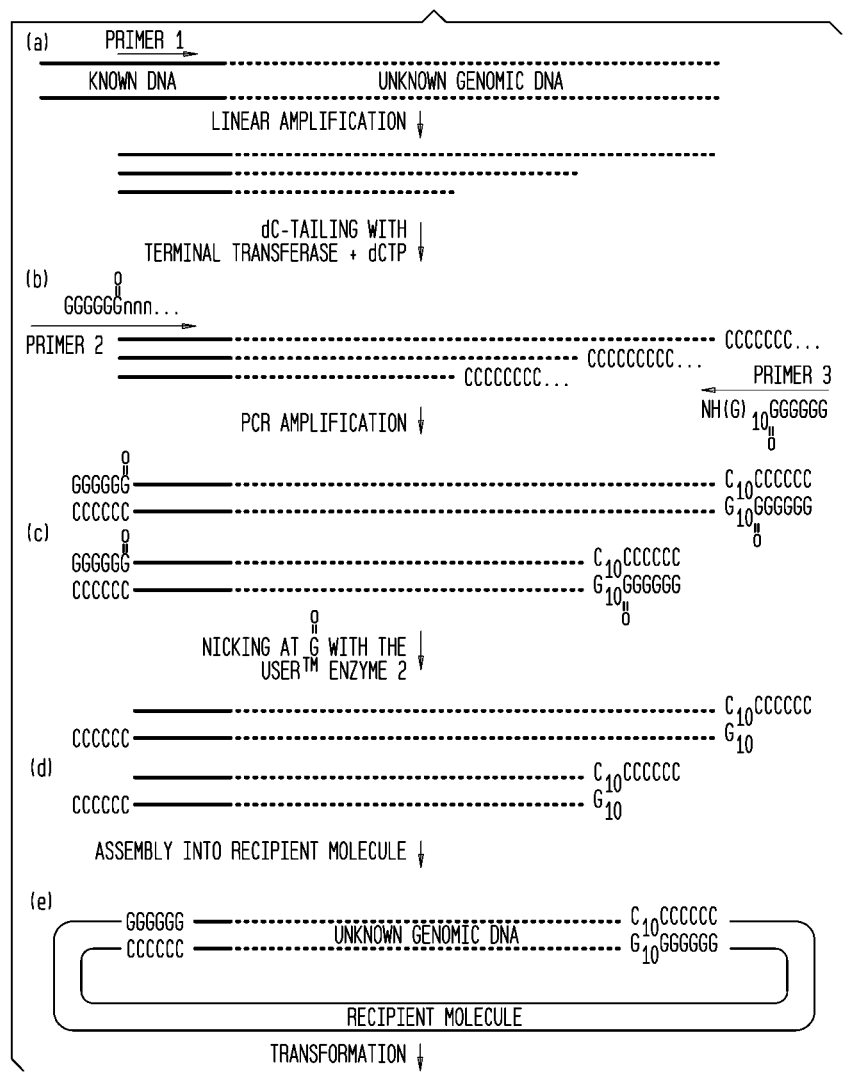

FIG. 17 shows how genomic DNA fragments outside the boundaries of known sequences can be cloned into a recipient molecule:

(a) Primer 1 is specific for the target DNA close to the end of the known sequence permitting linear amplification to produce single-stranded polynucleotide molecules of different lengths;

(b) polyC tails are added to the 3' ends of the amplified single-stranded polynucleotide molecules using terminal transferase and dCTP. PolyC tailed single-stranded fragments are amplified with Primer 2 and Primer 3. Primer 2 has an 8-oxo-guanine at the junction between the priming sequence and a 5' polyG tail. Primer 3 is poly dG which is complementary to the polyC tail and contains an 8-oxo-guanine close to the 5' end at a position corresponding to the position of 8-oxo-guanine in Primer 2. "N"—A, G, C or T, whereas "H"—indicates A, T or C;

(c) the product of amplification with 8-oxo-guanine at the sixth position from the 5' end of the fragments;

(d) the amplified DNA is nicked by USER™ Enzyme 2 at 8-oxo-guanine thus generating 3' single-stranded extensions of six cytosines on both ends of the amplified products;

(e) the amplified products representing the unknown genomic DNA flanked by 3' single-stranded extensions of six cytosines are inserted into the recipient molecule which has 3' single-stranded extensions consisting of six guanines.

Figure 18:
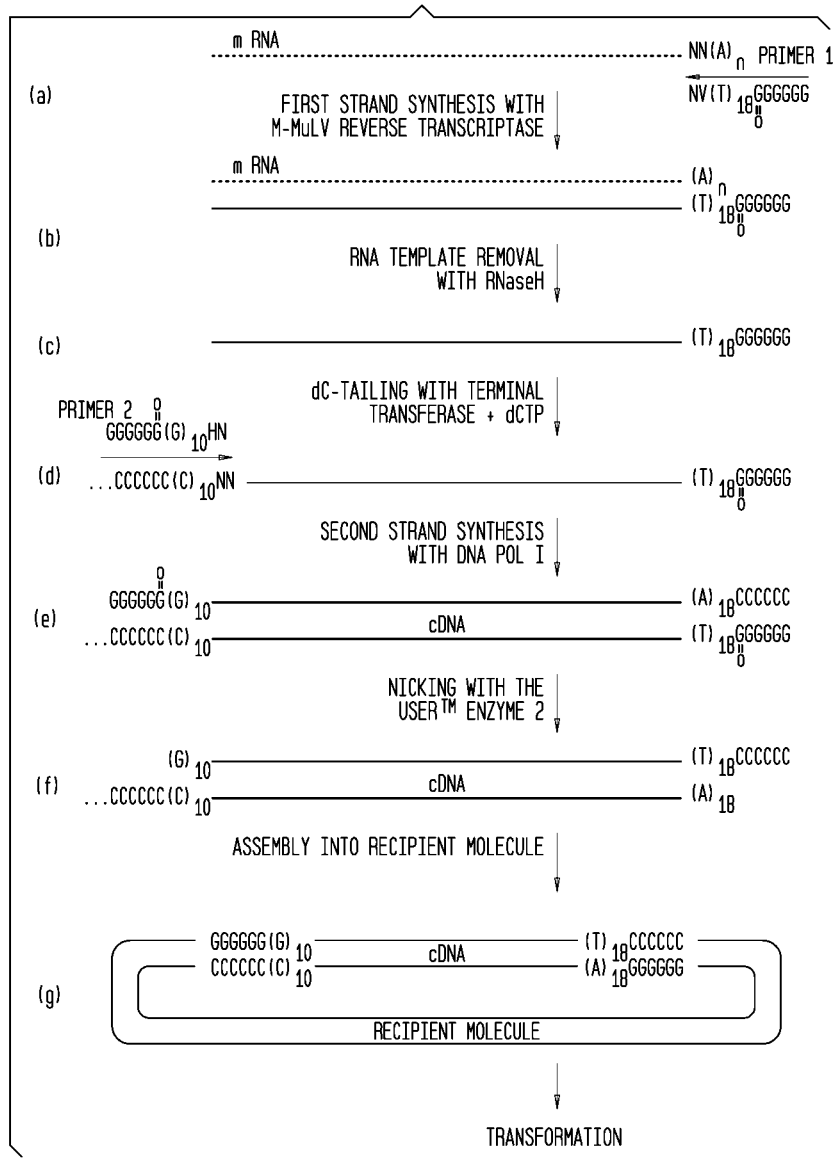

FIG. 18 shows how a cDNA library can be created from mRNA by generating a library of double-stranded cDNA molecules flanked by 3' single-stranded extensions that are complementary to the 3' single-stranded extensions on the recipient molecule:

(a) the mRNA for generating a cDNA and Primer 1 for first strand synthesis. Primer 1 includes a priming sequence of polyT and an additional hexaguanine sequence at its 5' end, where guanine at the 6th position from the 5' end is replaced by an 8-oxo-guanine: "V"=A, C or G; "N"=A, T, C or G; and "G=O" indicates an 8-oxo-guanine;

(b) a cDNA/mRNA hybrid is generated in the presence of a reverse transcriptase (M-MuLV) and Primer 1;

(c) the mRNA is removed from the hybrid by RNase H digestion leaving single-stranded cDNA molecule;

(d) a poly dC tail is added at the 3' end of the single-stranded cDNA using a terminal transferase and dCTP. Primer 2 which includes poly dG sequence that hybridizes to the poly dC tail of cDNA is designed to have an 8-oxo-guanine at the 6th position from the 5' end. "H"=A, T or C;

(e) the double-stranded cDNA is generated using DNA Polymerase I and Primer 2;

(f) the double-stranded cDNA is treated with USER™ Enzyme 2 to nick the 8-oxo-guanine yielding 3' single-stranded extensions of 6 cytosines;

(g) the recipient molecules having 3' single-stranded extensions of 6 guanines are annealed to the cDNA molecules produced in (f) to form recombinant molecules thus generating a cDNA library.

Figure 19:
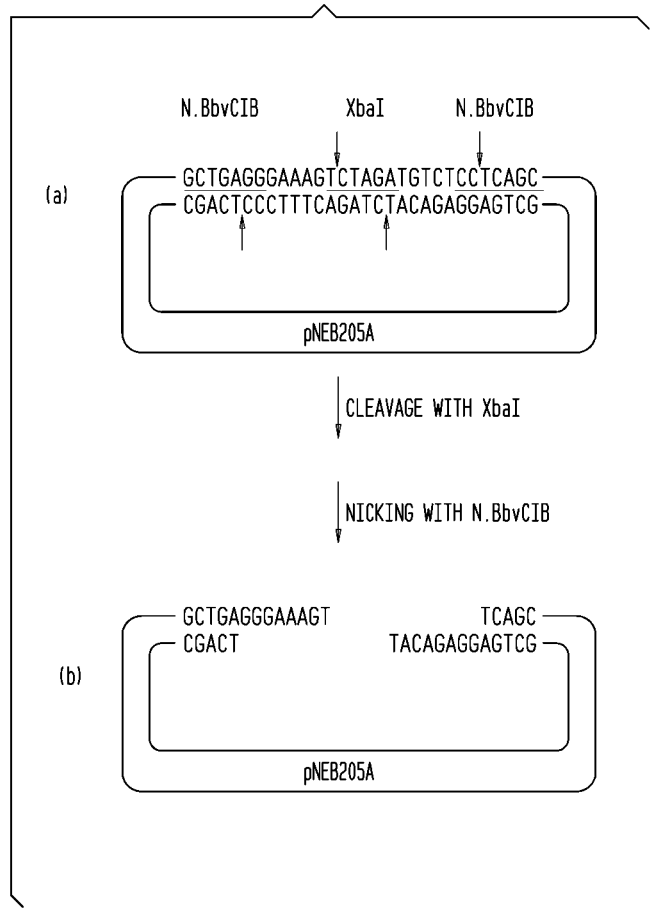

FIG. 19 shows the design of a recipient molecule pNEB205A (New England Biolabs, Inc., Beverly, Mass.) and generation of a linearized vector for cloning of target molecules:

(a) the recipient molecule is here shown to be a circular vector referred to as pNEB205A which is constructed by inserting a cassette (SEQ ID NO:1) which contains two inversely-oriented nicking N.BbvCIB sites flanking the XbaI restriction site into the multiple cloning site of pNEB193 vector (New England Biolabs, Catalog, 2002-2003, p. 318). The enzyme recognition sites within the cassette are underlined and the cleavage positions within the sites are indicated by the arrows.

(b) the product (SEQ ID NO:2) of digestion of pNEB205A with N.BbvCIB and XbaI is a linear vector pNEB205A flanked with 8-nucleotide long 3' single-stranded extensions, GGGAAAGT-3' and GGAGACAT-3', respectively.

Figure 20:
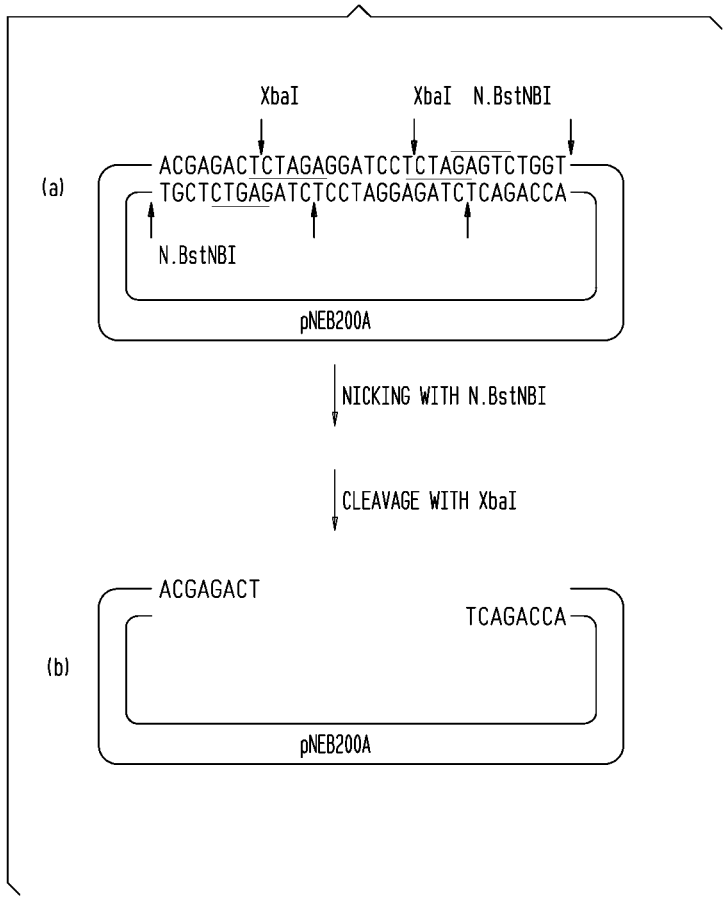

FIG. 20 shows the design of a recipient molecule pNEB200A (New England Biolabs, Inc., Beverly, Mass.) and production of linearized vector for cloning of target molecules:

(a) the recipient molecule is here shown to be a circular vector referred to as pNEB200A which is constructed by inserting a cassette (SEQ ID NO:3) which contains two inversely-oriented nicking N.BstNBI sites flanking two XbaI restriction sites into the multiple cloning site of pNEB193 vector. The enzyme recognition sites within the cassette are underlined and the cleavage positions are indicated by the arrows. N.BstNBI cleaves outside the recognition sequences.

(b) the product of digestion of pNEB200A with N.BstNBI and XbaI is a linear vector pNEB200A flanked with 8-nucleotide long 3' single-stranded extensions, ACGAGACT-3' and ACCAGACT-3', respectively.

Figure 21:
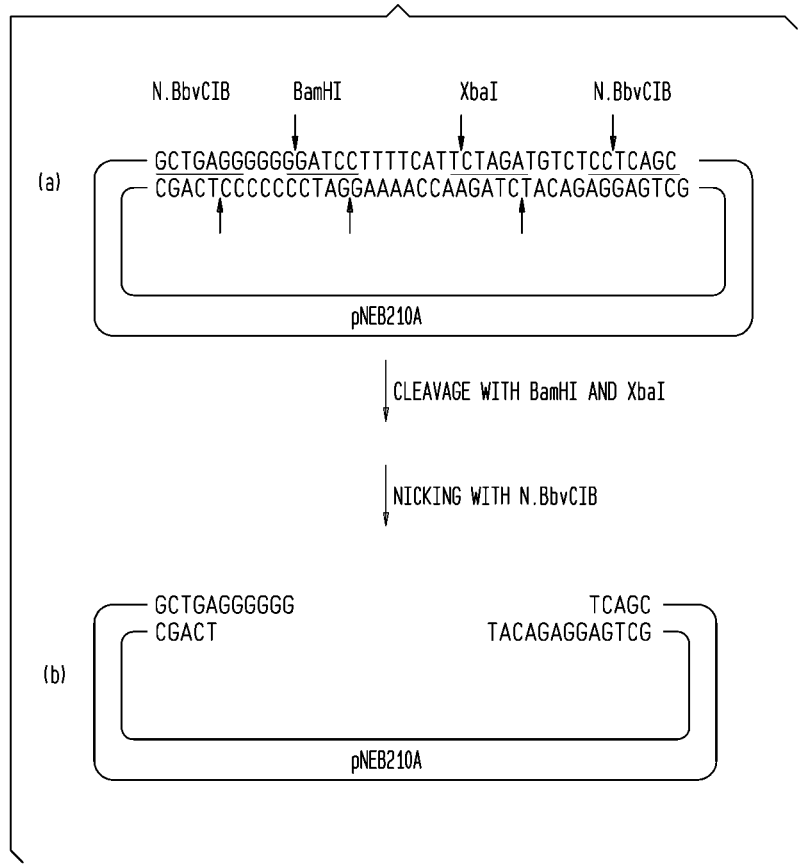

FIG. 21 shows the design of a recipient molecule pNEB210A (New England Biolabs, Inc., Beverly, Mass.) and production of linearized vector for cloning of target molecules:

(a) the recipient molecule is here shown to be a circular vector referred to as pNEB210A which is constructed by inserting a cassette (SEQ ID NO:4) which contains two inversely-oriented nicking N.BbvCIB sites flanking BamHI and XbaI restriction sites into the multiple cloning site of pNEB193 vector. The enzyme recognition sites within the cassette are underlined and the cleavage positions within the sites are indicated by the arrows.

(b) the product (SEQ ID NO: 5) of digestion of pNEB210A with N.BbvCIB, BamHI and XbaI is a linear vector pNEB210A flanked with 6-nucleotide long 3' single-stranded extension of GGGGGG-3' on one end and 8-nucleotide long 3' single-stranded extension of GGAGACAT-3' on the other end.

Figure 22:
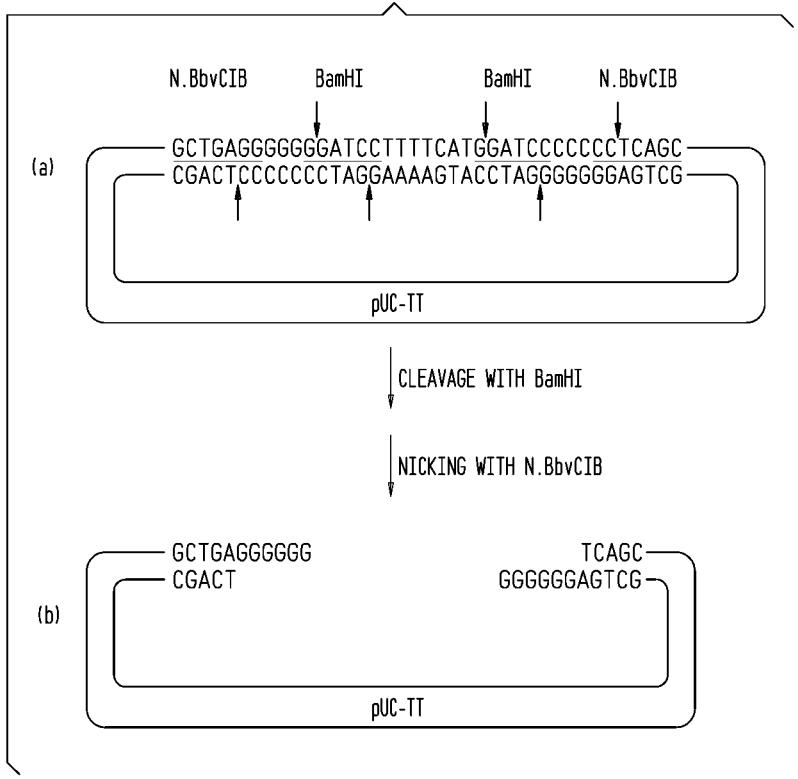

FIG. 22 shows the design of a recipient molecule pUC-TT (New England Biolabs, Inc., Beverly, Mass.) and production of linearized vector for cloning of target molecules:

(a) the recipient molecule is here shown to be a circular vector referred to as pUC-TT which is constructed by inserting a cassette (SEQ ID NO:6) which contains two inversely-oriented nicking N.BbvCIB sites flanking two BamHI restriction sites into the multiple cloning site of pNEB193 vector The enzyme recognition sites within the cassette are underlined and the cleavage positions within the sites are indicated by the arrows.

(b) the product (SEQ ID NO:7) of digestion of pUC-TT with N.BbvCIB and BamHI is a linear vector pUC-TT flanked with 6-nucleotide long 3' single-stranded extensions of GGGGGG-3' on both ends.

Figure 23:
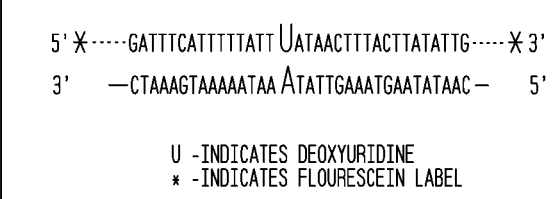

FIG. 23 shows the sequence (SEQ ID NO:8) of a 34-bp oligonucleotide duplex used to assay the activity of artificial nicking agents. The top strand of duplex is fluorescently labeled on both 5' and 3' ends (*) and contains a single deoxyuridine (U) at the $16^{th}$ position. The bottom strand of hetero-duplex contains a deoxyadenine across from the position corresponding to dU.

Figure 24:
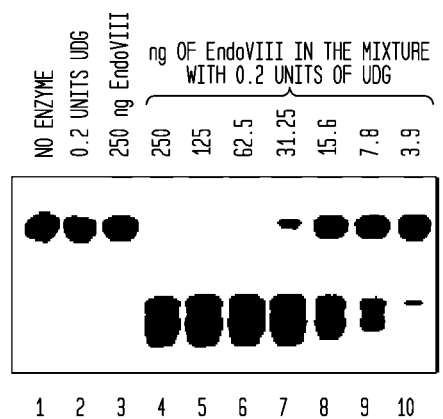

FIG. 24 shows how the optimal amount of EndoVIII glycosylase/AP lyase can be determined in a mixture with UDG glycosylase in order to produce the artificial nicking agent referred to as the USER™ Enzyme. The assay utilizes a substrate having a sequence shown in FIG. 23. 2-fold serially diluted amounts of EndoVIII varying in the range from 250 ng to 3.9 ng were pre-mixed with 0.2 unit of UDG glycosylase and assayed for complete nicking of 10 pmol of substrate. Lanes 1 is a control showing the substrate without enzyme treatment. Neither UDG alone (shown in lane 2) nor EndoVIII alone (shown in lane 3) is capable of nicking substrate containing deoxyuridine, but the mixtures containing 0.2 units of UDG and at least 31.25 ng of EndoVIII yield complete nicking of 10 pmol of substrate (lanes 4-7). Mixtures containing less than 31.25 ng of EndoVIII are only partially digested (lanes 8-10).

Figure 25:
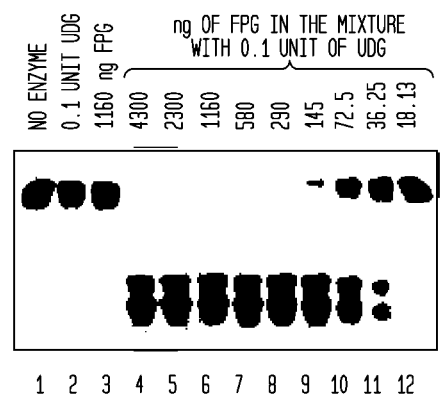

FIG. 25 shows how the optimal amount of FPG glycosylase/AP lyase can be determined in a mixture with UDG glycosylase in order to produce the artificial nicking agent referred to as the USER™ Enzyme 2. The assay utilizes a substrate having a sequence shown in FIG. 23. 2-fold serially diluted amounts of FPG varying in the range from 4300 ng to 19 ng were pre-mixed with 0.1 unit of UDG glycosylase and assayed for complete nicking of 10 pmol of substrate. Lane 1 is a control showing the substrate without enzyme treatment. Neither UDG alone (shown in lane 2) nor FPG alone (shown in lane 3) is capable of nicking substrate containing deoxyuridine (U), but the mixtures containing 0.1 unit of UDG and at least 290 ng of FPG yield complete nicking of 10 pmol of substrate (lanes 4-8). Mixtures containing less than 290 ng of FPG glycosylase/AP lyase are only partially digested (lanes 9-12).

FIG. 26A shows a design strategy for primers suitable for use in amplifying target molecule in order to generate 3' single-stranded extensions complementary with the 3' extensions on the linearized vector pNEB205A prepared as shown in FIG. 19. The left primer at the 5' end include sequence GGAGACAU (SEQ ID NO:9) which is identical to the right extension on the pNEB205A in FIG. 19, except for 3'-terminal thymine which is replaced by deoxyuridine (U) in the primer sequence followed by the target molecule-specific sequence from the 5' end. The right primer at 5' end include sequence GGGAAAGU (SEQ ID NO:10) which is identical to the left extension on the pNEB205A in FIG. 19, except for 3'-terminal thymine which is replaced by deoxyuridine (U) in the primer sequence followed by the 3' terminal target molecule-specific sequence from the reverse strand.

Figure 26B:
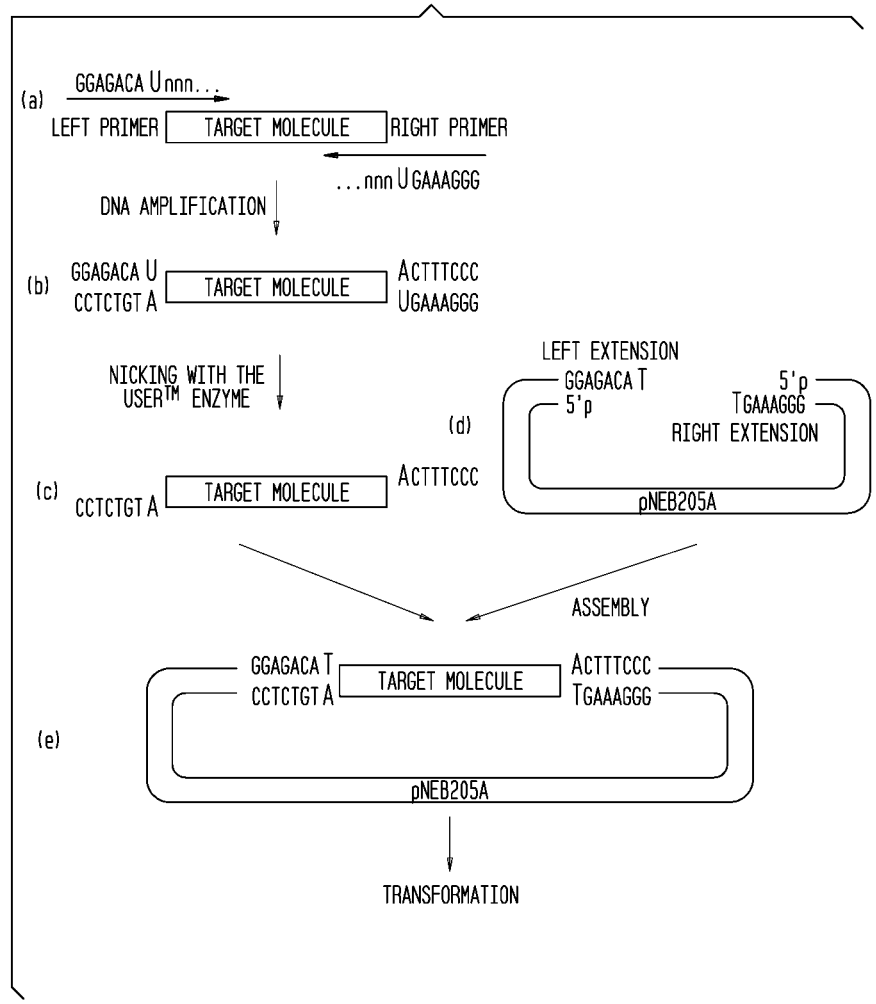

FIG. 26B shows an overview of target molecule cloning method:

(a) a left primer (SEQ ID NO:11) and a right primer for amplifying target DNA were designed according to FIG. 26A;

(b) the amplified DNA includes a target molecule sequence which is extended at both ends by vector compatible sequences. A single U occurs at each junction and on the opposite strands with respect to each other;

(c) the amplified target molecule having 3' single-stranded extensions generated after nicking at deoxyuridine (U) with the USER™ Enzyme and dissociation of the nicked 5'-terminal strand;

(d) linear vector pNE205A is shown in an inverted orientation relative to FIG. 19, having 3' single-stranded extensions complementary to single-stranded extensions on the target molecule in step (c);

(e) the recombinant molecule resulting from combining the target molecule and the linearized vector pNEB205A of steps (c) and (d).

Figure 27A:
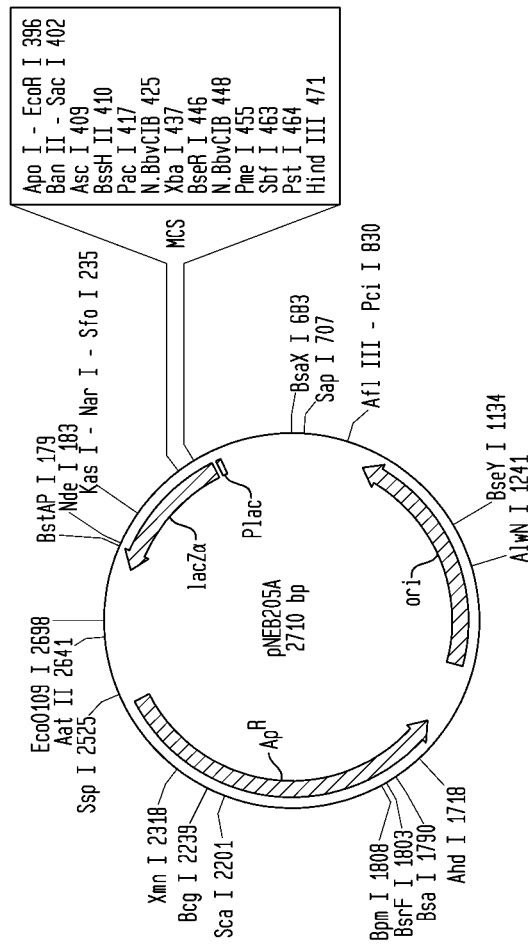

FIG. 27A shows a restriction map of the pNEB205A plasmid. pNEB205A is identical to either pNEB193 (New England Biolabs Catalog 2002-2003, p. 318) or pUC19 (Yanisch-Perron, et al. *Gene* 33:103-119 (1985)) except for the multiple cloning site (MCS). The new MCS is in frame with the lacZα gene, allowing screening for insertions using α-complementation.

FIG. 27B shows the nucleotide sequence (SEQ ID NO:12) of the multiple cloning site (MCS) of pNEB205A. The nucleotide sequence is numbered to show the location of the MCS within pNEB205A. The N-terminal amino acid sequence of the LacZα fragment is shown under the respective codons. Restriction sites are underlined. Cleavage sites of XbaI restriction endonuclease and N.BbvCIB nicking endonuclease are shown as black triangles. The shaded area shows the nucleotide sequence which is removed from pNEB205A after digestion with XbaI and N.BbvCIB.

FIG. 27C shows the sequence (SEQ ID NO:13 and SEQ ID NO:14) of 3' single-stranded extensions on the linearized pNEB205A vector, which were created by digestion with N.BbvCIB and XbaI within the MCS shown in FIG. 27B.

Figure 28:
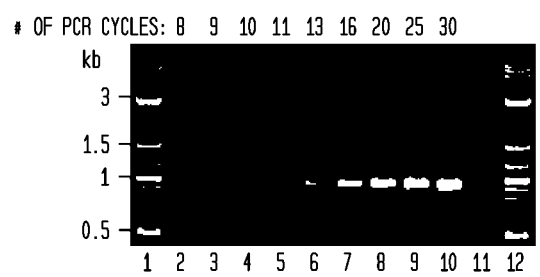

FIG. 28 shows the PCR-amplified Chloramphenicol Resistance gene (cat) DNA (0.95 kb) in a 10 μl of amplification sample (out of 50 μl of the total PCR volume). Lanes 1 and 12 contain a 2-Log DNA Ladder (New England Biolabs, Inc., Beverly, Mass.). Lanes from 2 to 10 show PCR sample after 8, 9, 10, 11, 13, 16, 20, 25 and 30 cycles containing 5, 10, 17, 45, 82, 164, 215, 346 and 390 ng of DNA, respectively. Lane 11 shows 1 μl (20 ng) of the linearized vector pNEB205A.

Figures 29, 30:
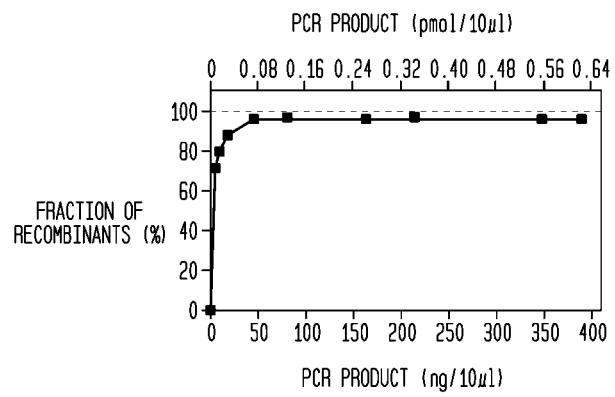

FIG. 29 shows the number of colonies produced by 25 μl of transformation reaction. White colonies represent transformants carrying recombinant molecules. Blue colonies represent transformants carrying unmodified vector. Different amounts of PCR product varying in the range from 5 ng (0.0008 pmol) to 390 ng (0.62 pmol) were assembled into 20 ng (0.011 pmol) of linear pNEB205A following the reaction protocol described in Example III. The transformation results represent the average of three independent experiments. (±) indicates the standard deviation value (s) which was calculated using the formula: $s^2=S(X-M)^2/(N-1)$, where X is the measurement value, M is the mean and N is the number of measurements. Cloning efficiency was determined by calculating the fraction of white colonies in the total number of transformants.

FIG. 30 shows the graphical illustration of the results presented in FIG. 29 showing that fraction of recombinants is 94%-95% if the concentration of PCR product is 50 ng (0.08 pmol) or higher.

Figure 31:
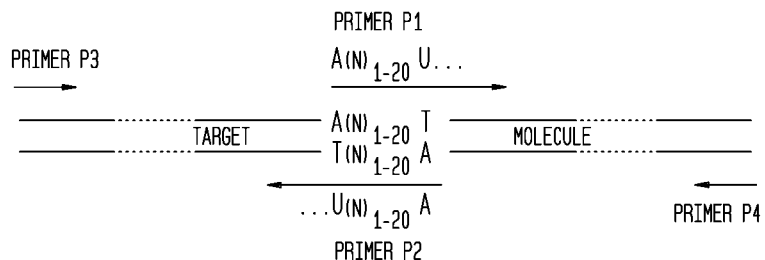

FIG. 31 shows the design strategy of primer pairs P2/P3 and P1/P4 for generating intermediate PCR fragments of a target molecule flanked with complementary 3' single-stranded extensions. The overlapping Primers P1 and P2 start with a 5' adenine; $(N)_{1-20}$ indicate the overlap region shared by overlapping primers where each primer contains the reverse complement sequence of the other. The overlap sequence at the 3' end is flanked by a deoxyuridine (U), which is across from the 5' adenine on the opposite primer. Downstream of deoxyuridine (U), the primers prime the respective sequences on the target molecule.

Figure 32:
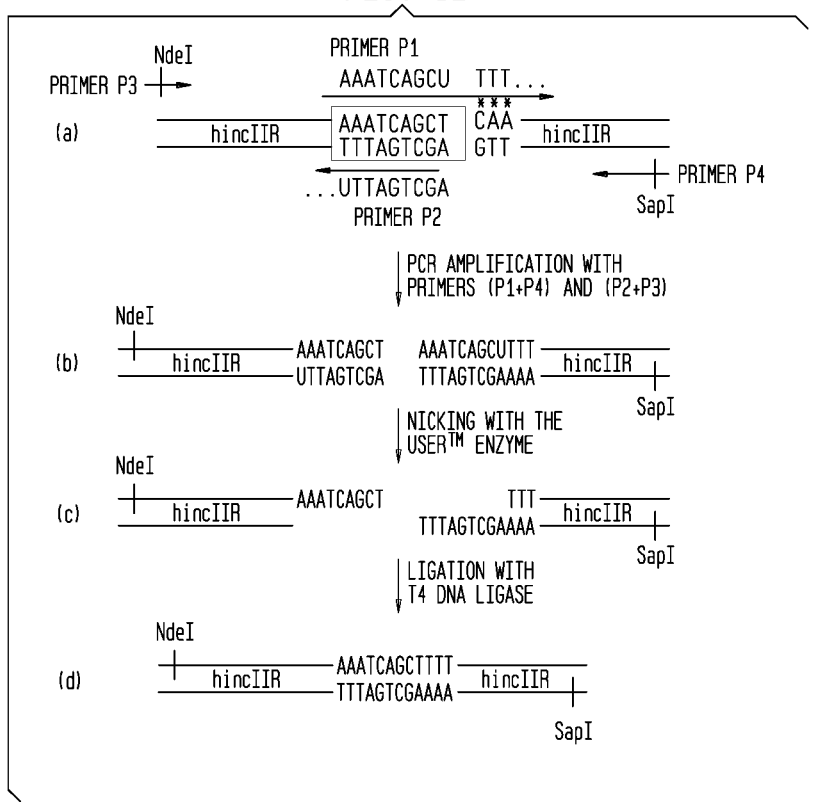
Figure 32:
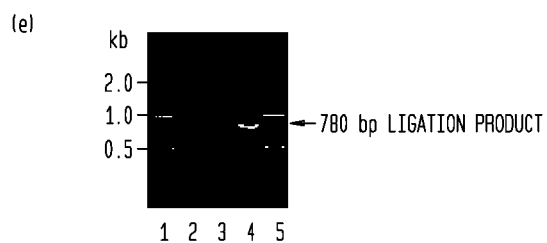

FIG. 32 shows site-specific mutagenesis in which a codon substitution (3 nucleotide substitution) is introduced into a gene encoding HincII restriction endonuclease (SEQ ID NO:16):

(a) design of primer pairs P2/P3 and P1/P4 for amplification of hincIIR gene as two overlapping fragments. To create overlap region, a 9-nucleotide sequence which starts with adenine and ends with thymine (marked as boxed area) is selected on the sequence of hincIIR gene in the vicinity of nucleotides targeted for mutagenesis (marked by asterisks). This sequence is included at the 5' ends of the overlapping Primers P1 and P2, except that deoxyuridine (U) is introduced at the last position of the overlap sequence. In Primer P1 downstream of U, codon CAA is replaced by codon TTT followed by the hincIIR-specific sequence for priming. The Primer P2 sequence downstream of U is complementary to hincIIR-specific sequence. NdeI site is engineered at 5' end of Primer P3 and SapI site is engineered at 5' end of Primer P4;

(b) two PCR amplification fragments are shown. Both fragments overlap by a 9-bp sequence and contain a single uracil residue on the opposite strands. Left-side fragment contains codon TTT instead of a wild type codon CAA.

(c) the fragments flanked by single-stranded extensions that are complementary to each other produced after nicking at the uracils with the USER™ Enzyme;

(d) the fragments are annealed and ligated with T4 DNA Ligase through their complementary extensions to form the modified nucleotide sequence (SEQ ID NO:18) of hincIIR gene.

(e) agarose gel electrophoresis showing the results of the pilot ligation. Lanes 1 and 5 show 2-Log DNA Ladder. Lane 2 shows 1 μl of PCR sample containing a 420-bp hincIIR gene fragment. Lane 3 shows 1 μl of PCR sample containing a 380-bp hincIIR gene fragment. Lane 4 shows 10 μl of the pilot ligation reaction containing the 780-bp hincIIR gene with the codon CAA substitution to codon TTT.

Figure 33:
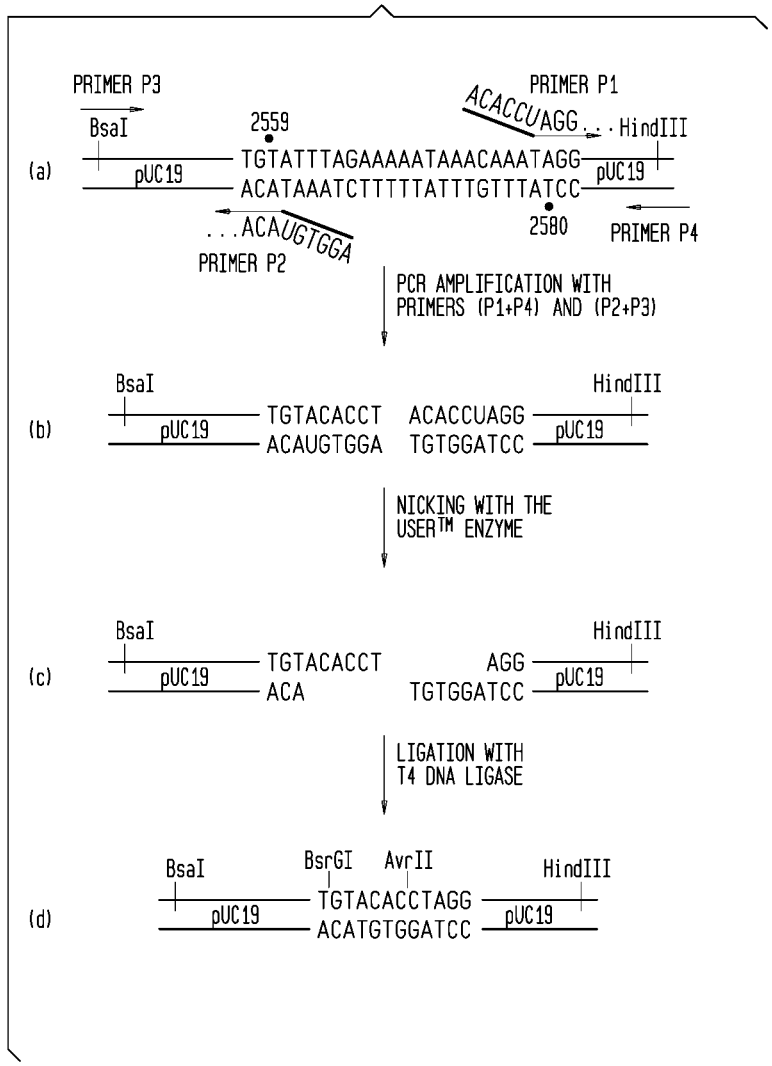
Figure 33:
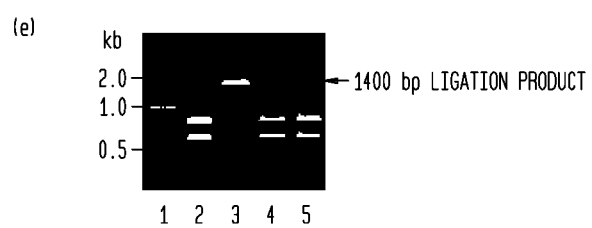

FIG. 33 shows the insertion of two unique restriction sites and deletion of 18-bp sequence from pUC19 plasmid:

(a) the primer pairs P1/P4 and P2/P3 are designed according to FIGS. 10A and 11 as follows. The overlapping Primers P1 and P2 at their 5' ends contain an additional 6-nucleotide insertion sequences required for creation of BsrGI and AvrII restriction sites. The insertion sequences in both primers are complementary to each other and contain deoxyuridine (U) at the 6th position. Downstream of U, Primers P1 and P2 prime the respective pUC19 sequences, which start precisely beyond the targeted 18 bp deletion region (SEQ ID NO:19). Primer P3 primes pUC19 sequence across the BsaI site and Primer P4 primes pUC19 sequence across the HindIII site;

(b) two PCR amplification fragments with a 6-bp overlapping sequence where each fragment has a single uracil residue positioned on the opposite strand with respect to each other;

(c) the PCR fragments flanked by single-stranded extensions that are complementary to each other formed after nicking at the uracils with the USER™ Enzyme;

(d) the product (SEQ ID NO:20) of annealing and ligation of fragments with T4 DNA Ligase through complementary single-stranded extensions. The product contains the recognition sites of restriction endonucleases BsrG1 and AvrII;

(e) agarose gel electrophoresis showing the results of ligation. Lane 1 shows 2-Log DNA Ladder. Lane 2 shows 610-bp and 810-bp PCR fragements. 1 μl of each PCR sample was combined and loaded on gel. Lane 3 shows 10 μl of the ligation reaction containing the 1420-bp ligated pUC19 fragment. Lane 4 shows the ligated 1420-bp fragment is cleaved with BsrGI restriction endonuclease. Lane 5 shows the ligated 1420-bp fragment is cleaved with AvrII restriction endonuclease.

Figure 34:
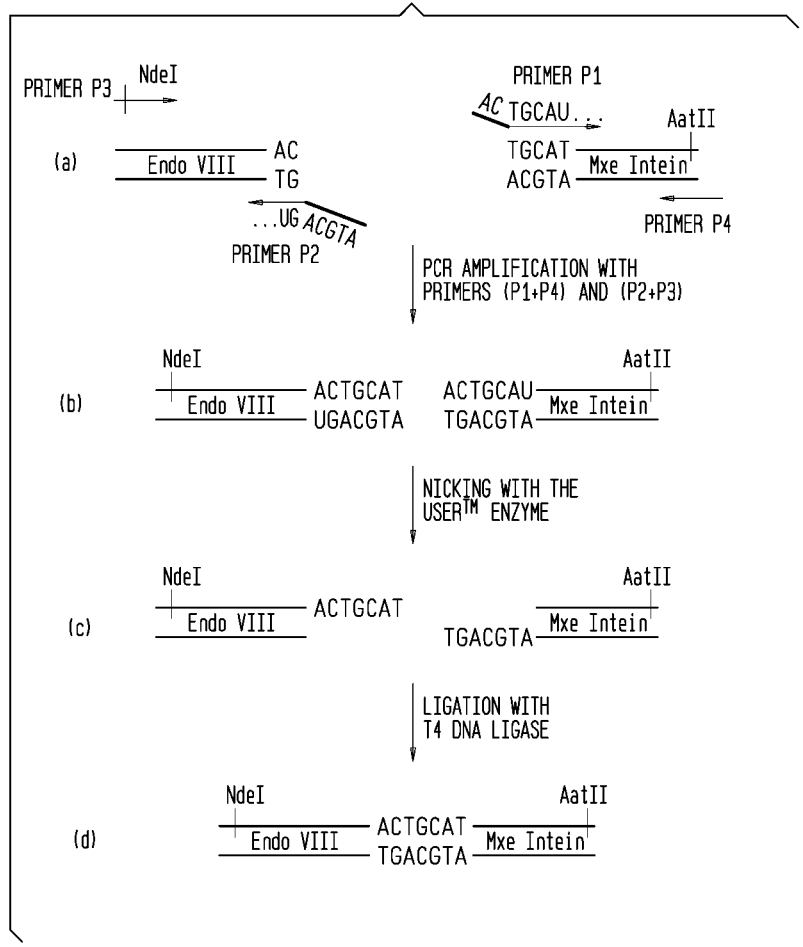
Figure 34:
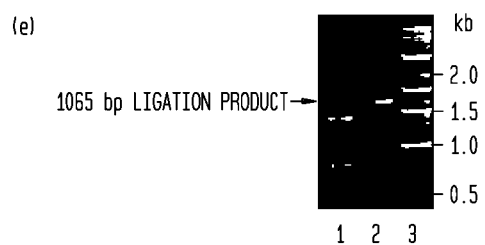

FIG. 34 shows fusion of genes coding for E. coli Endonuclease VIII and Mxe Intein:

(a) the primer pairs P1/P4 and P2/P3 are designed according to FIG. 12 as follows. Overlapping Primers P1 and P2 prime the respective gene-specific sequences and at their 5' ends have a 7-bp overlapping sequence flanked by deoxyuridine (U). To create the 7-bp overlap, Primer P2 at its 5' end is extended by five 5'-terminal nucleotides of the Mxe Intein gene, and Primer P1 at its 5' end is extended by two 3'-terminal nucleotides of EndoVIII gene. An NdeI site is engineered at 5' end of Primer P3 and Primer P4 primes across the AatII site in Mxe Intein gene;

(b) two PCR amplification fragments having the common overlap region of seven nucleotides as described in (a). Both amplification products contain a single uracil residue positioned on the opposite strands with respect to each other;

(c) the fragments flanked by single-stranded extensions that are complementary to each other produced after nicking at the uracils with the USER™ enzyme;

(d) the product of annealing and ligation of fragments with T4 DNA Ligase through complementary single-stranded extensions. The product is a precise fusion of two genes.

(e) agarose gel electrophoresis showing the results of the ligation. 1 µl PCR samples containing 265-bp fragment of the Mxe Intein gene and an 800-bp EndoVIII gene were combined and loaded on gel (Lane 1). Lane 2 shows 2 µl of the ligation reaction showing the 1065-bp ligation product, which represents a Mxe Intein gene fragment fused to the 3' end of the EndoVIII gene. Lane 3 shows 2-Log DNA Ladder.

Figure 35:
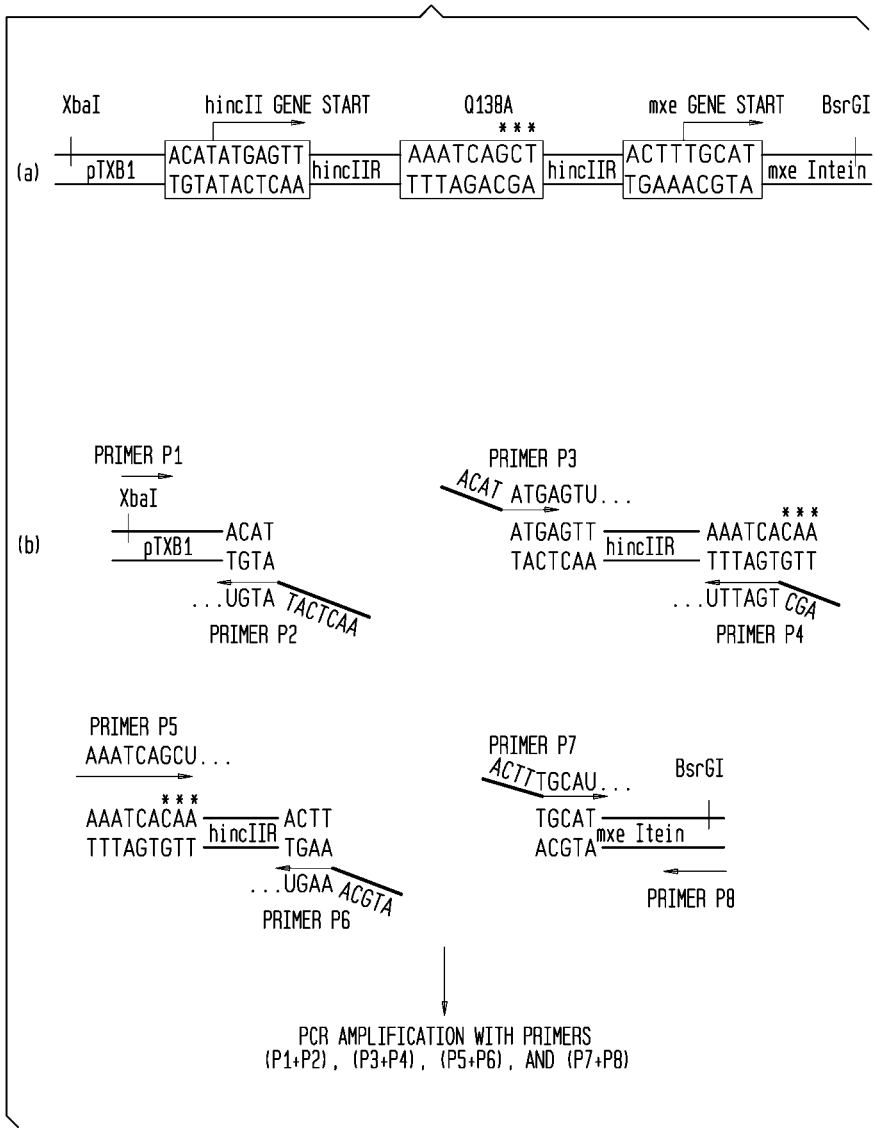
Figure 35:
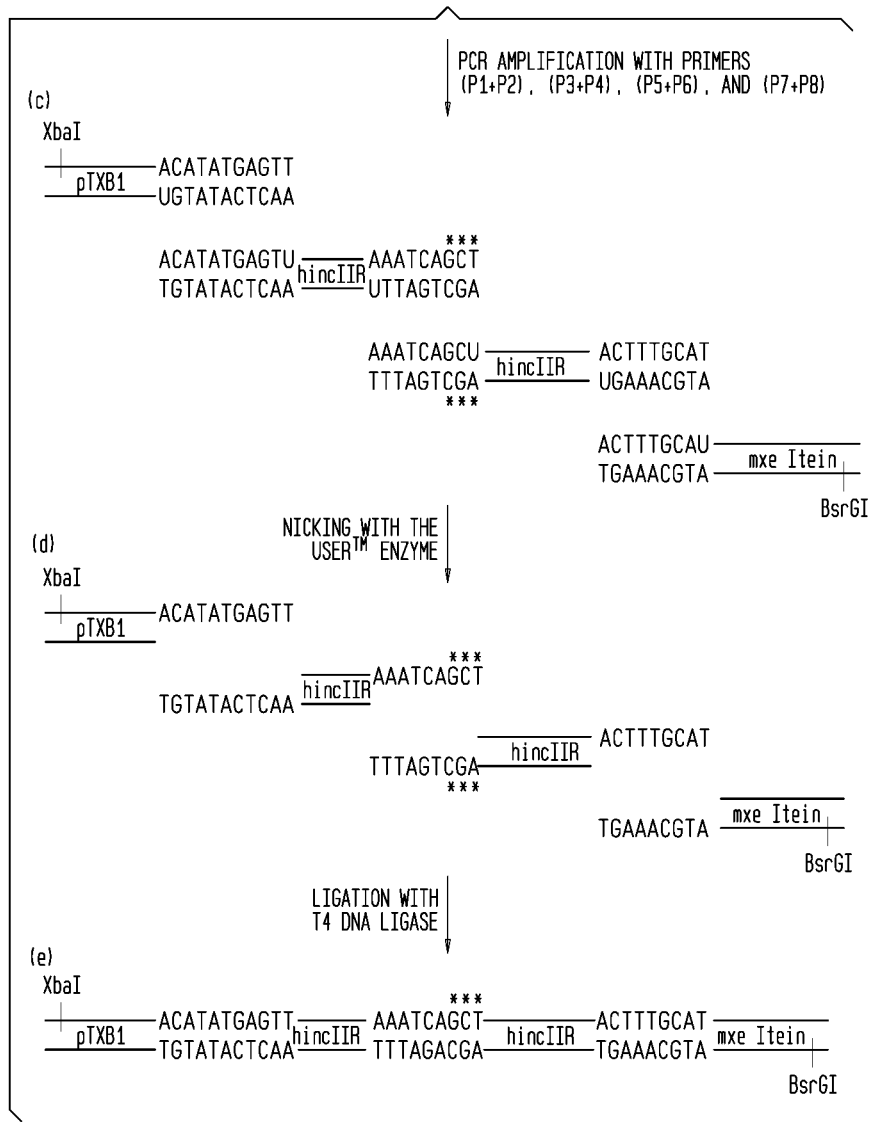
Figure 35:
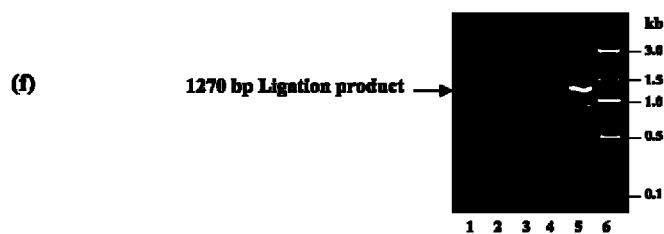

FIG. 35 shows concurrent site-specific mutagenesis and gene fusion:

(a) shows the final product of site-specific mutagenesis and gene fusion. A hincIIR gene sequence is altered to generate hincIIQ138A variant, and inserted between the promoter region of pTXB1 (SEQ ID NO:21) (New England Biolabs, Inc., Beverly, Mass.) vector and the 5' end of the Mxe Intein gene. The start positions of hincIIR and Mxe Intein genes are indicated by arrows. Asterisks indicate the position of nucleotides altered in the primer sequences to introduce a codon CAA to GCT substitution. The nucleotide sequences of the overlap regions used to design overlapping primer pairs P2/P3, P4/P5 and P6/P7, are shown within the boxed area.

(b) primer pairs P1/P2, P3/P4, P5/P6 and P7/P8 were designed for DNA amplification according to FIG. 13. The overlapping primer pairs P2/P3 (SEQ ID NO:22), P4/P5 and P6/P7 have at their 5' ends the overlapping sequences shown within the respective boxed area in (a) and contain a deoxyuridine (U) at the 3'-terminal position of the overlap sequence. Primer P1 primes across the XbaI site in the promoter region of pTXB1 vector and Primer P8 primes across the BsrGI site in the Mxe Intein gene;

(c) four PCR amplification fragments each having a common overlap region with the next in line fragment. The fragment coding for pTXB1 promoter region overlaps by 11-bp sequence with the 5' terminal part of the hincIIR gene; the 5' terminal part of hincIIR gene overlaps by 9-bp sequence with the 3'-terminal part of the hincIIR gene; and the 3'-terminal part of the hincIIR gene overlaps by 9-bp sequence with the 5'-terminal part of the Mxe Intein gene. The hincIIR fragments at the junction have a desired nucleotide changes (indicated by asterisks). The outside amplification products contain a single uracil residue positioned on the opposite strands, while two middle fragments that contain two uracils per fragment positioned on the opposite strands;

(d) the fragments flanked by single-stranded extensions that are complementary to each other after nicking at uracils with the USER™ enzyme;

(e) the product of annealing and ligation of fragments with T4 DNA Ligase through complementary single-stranded extensions. The product is a precise fusion of four fragments, which is identical to (a);

(f) agarose gel electrophoresis showing the results of the pilot ligation. Lane 1 shows 1 µl of PCR sample containing a 140-bp fragment of the promoter region of pTXB1 vector. Lane 2 shows 1 µl of PCR sample containing a 420-bp fragment of the hincII gene. Lane 3 shows 1 µl of PCR sample containing a 380-bp fragment of the hincII gene. Lane 4 shows 1 µl of PCR sample containing a 360-bp fragment of the 5' terminal Mxe Intein gene. Lane 5 shows 10 µl of the pilot ligation reaction with the 1270-bp ligation product, which represents the linearly assembled final construct. Lane 6 shows 2-Log DNA Ladder.

Figure 36:
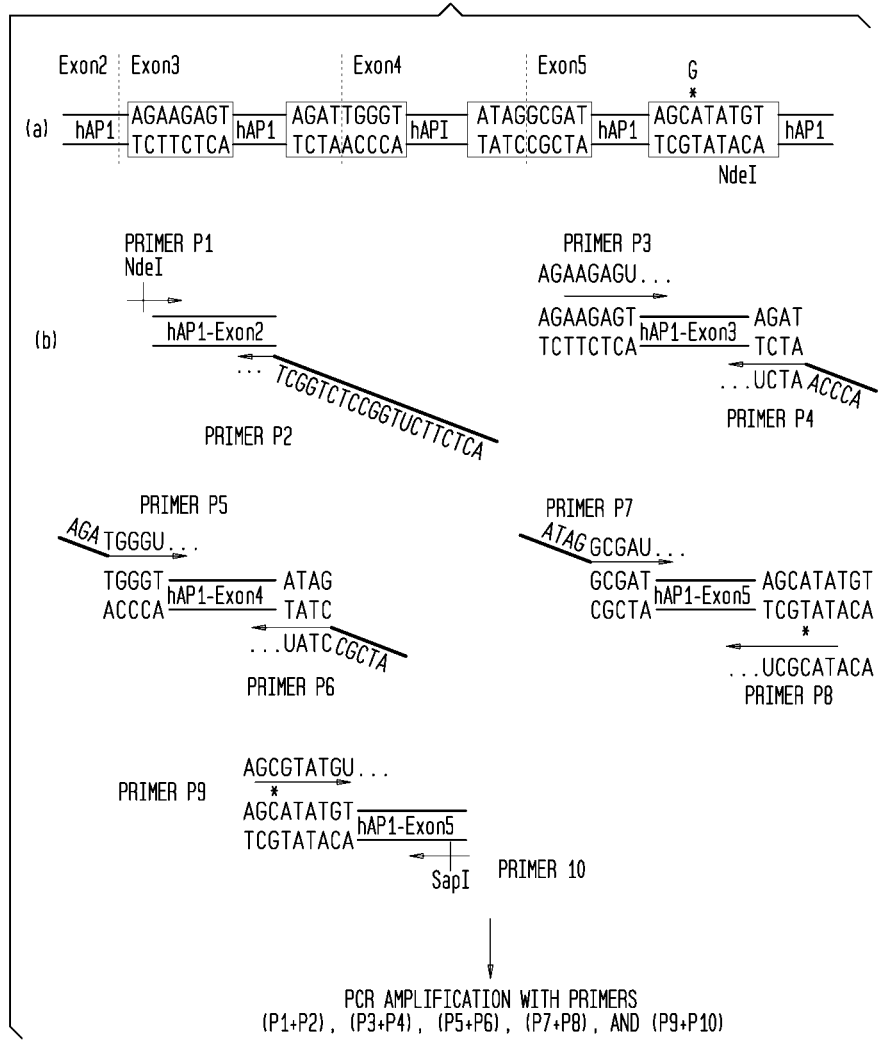
Figure 36:

FIG. 36 shows the assembly of human AP1 (hAP1) endonuclease gene from total human genomic DNA concurrent with site-specific mutagenesis:

(a) cDNA of the hAP1 endonuclease gene with Exons 2-5. The junctions of the individual exons are shown by vertical dotted lines. Exon 5 contains the NdeI site which is targeted for silent mutation of A to G (indicated by asterisk). The nucleotide sequences of the overlap regions, which were used to design overlapping primer pairs P2/P3, P4/P5, P6/P7 and P8/P9, are shown within the boxed area.

(b) primer pairs P1/P2, P3/P4, P5/P6, P7/P8 and P9/P10 for amplification of individual exons of hAP1 gene from total genomic DNA were designed as follows. Overlapping primers P2/P3, P4/P5, P6/P7 and P8/P9 have overlapping sequences at their 5' ends shown within the boxed area in (a), and further containing a deoxyuridine (U) at the 3'-terminal position of the overlap sequence. An NdeI site is engineered at 5' end of Primer P1 and SapI site is engineered at 5' end of Primer P10;

(c) five PCR amplification fragments each having the common overlap region with the adjacent fragment. The 3' end of Exon 2 overlaps with the 5' end of Exon 3 (SEQ ID NO:23); the 3' end of Exon 3 overlaps with the 5' end of Exon 4; the 3' end Exon 4 overlaps with the 5' end of the first part of Exon 5 which on its 3' end overlaps with the 5' end of the second part of Exon 5. The overlapping fragments of Exon 5 at the junction have a desired nucleotide change (indicated by asterisk). The outside amplification products contain a single uracil residue positioned on opposite strands, while the three middle fragments contain two uracils per fragment on opposite strands.

(d) the fragments flanked by single-stranded extensions that are complementary to each other in the specified order after nicking at uracils with the USER™ Enzyme;

(e) the product of annealing and ligation of fragments with T4 DNA Ligase through complementary single-stranded extensions. The product is a precise and ordered fusion of five fragments constituting the hAP1 gene with the mutated Exon 5 sequence;

(f) agarose gel electrophoresis showing the results of the pilot ligation. Lanes 1 and 8 show 2-Log DNA Ladder. Lane 2 shows 1 µl of PCR sample containing an 80-bp fragment of the Exon 2. Lane 3 shows 1 µl of PCR sample containing a 180-bp fragment of the Exon 3. Lane 4 shows 1 µl of PCR sample containing a 200-bp fragment of the Exon 4. Lane 5 shows 1 µl of PCR sample containing an 80-bp fragment of the 5' terminal portion of the Exon 5. Lane 6 shows 1 µl of PCR sample containing a 460-bp fragment of the 3' terminal portion of the Exon 5. Lane 7 shows 10 µl of the pilot ligation reaction with the 1000-bp ligation product, which represents the hAP1 gene.

Figure 37:
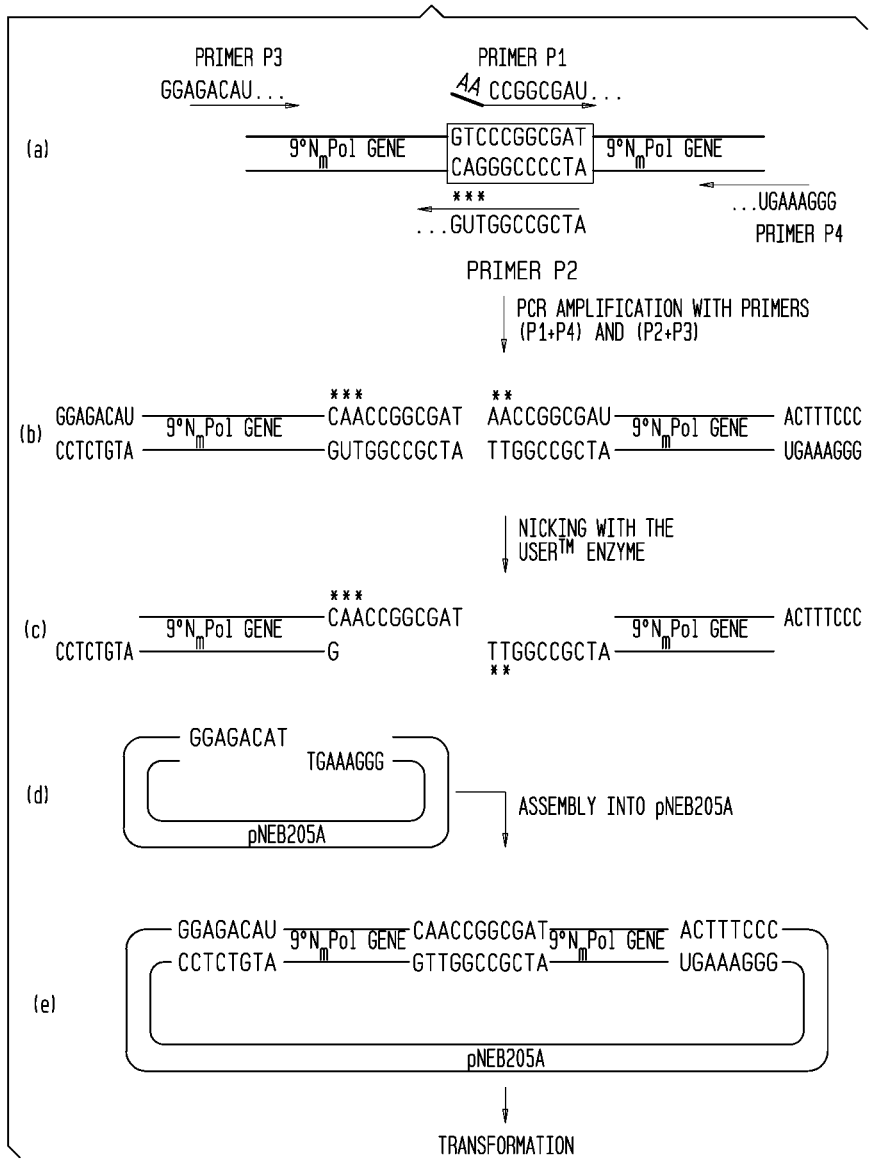

FIG. 37 shows directional assembly of mutagenized fragments of 9° $N_m$ DNA Polymerase gene (SEQ ID NO:25) into the linearized pNEB205A vector:

(a) primer pairs P1/P4 and P2/P3 were designed according to FIG. 16 as follows. The nucleotide sequence of the overlap region, which was used to design the overlapping Primers P1 and P2, is shown within the boxed area. "*" indicates the positions of nucleotides that were changed in the Primer P1 (SEQ ID NO:24) and P2 sequences to introduce codon GTC to CAA substitution in the 9° $N_m$ DNA Polymerase gene. Primers P3 and P4 on their 5' ends were supplemented with the additional sequences that were compatible with the 3' single-stranded extensions on the pNEB205A vector;

(b) two PCR amplification fragments (SEQ ID NO:26 and SEQ ID NO:24) having a common overlap region of ten nucleotides. Within the overlap region, the fragments have desired nucleotide changes (indicated by asterisks). Each fragment at the outside end is extended by eight nucleotides complementary to the corresponding extensions on pNEB205A shown in step (d). Both amplification products contain two uracil residues positioned on each end of fragment and on the opposite strands with respect to each other;

(c) fragments flanked by single-stranded extensions after nicking at uracils with the USER™ enzyme;

(d) linear pNEB205A vector flanked by 3' single-stranded extensions which are complementary to the outside extensions of fragments in step (c);

(e) recombinant molecule generated by annealed the fragments into pNEB205A vector through their complementary extensions.

Figure 38:
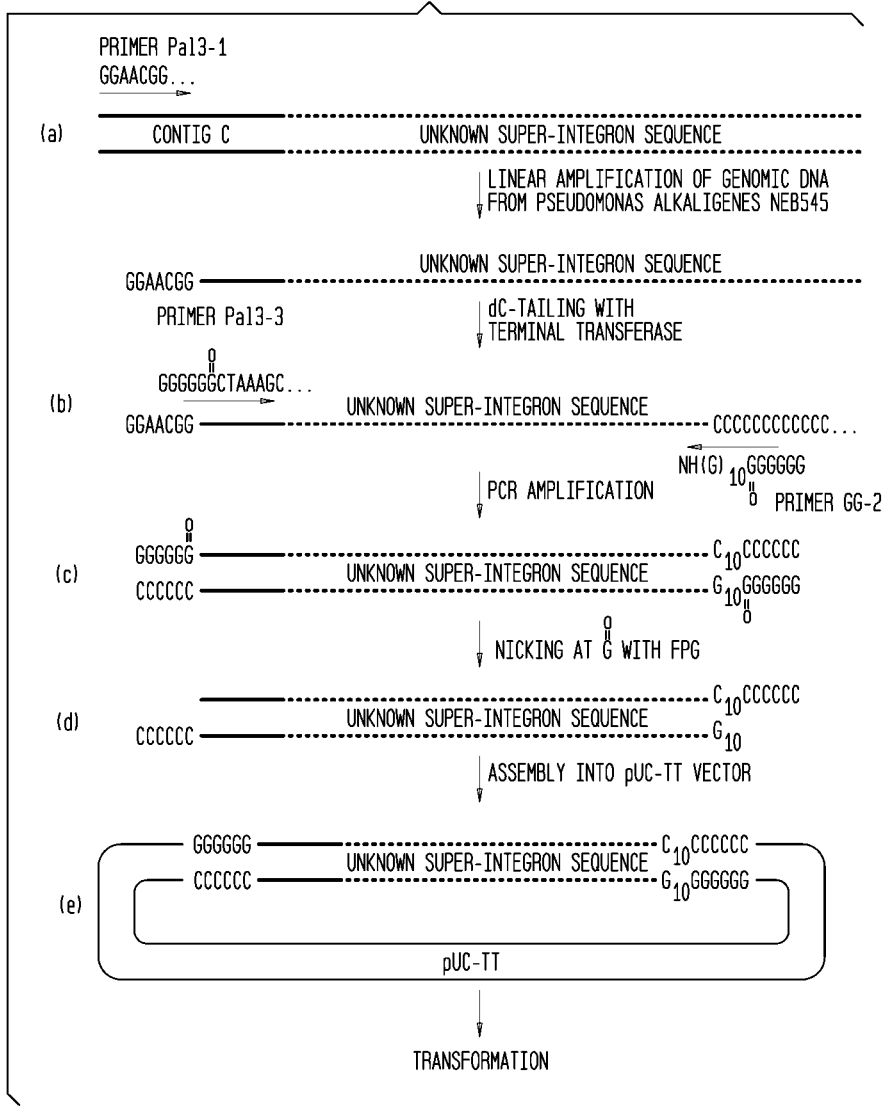

FIG. 38 shows the cloning of unknown 3' segment of the super-integron from *Pseudomonas alcaligenes* NEB#545 (New England Biolabs, Inc., Beverly, Mass.) into pUC-TT vector:

(a) Primer Pal3-1 primes the super-integron sequence in contig C for producing single-stranded polynucleotide molecules of different lengths containing the unknown sequence of super-integron;

(b) polyC tails were added to the 3' ends of the amplified single-stranded molecules using terminal transferase and dCTP. PolyC tailed single-stranded fragments were then amplified with Primers Pal3-3 (SEQ ID NO:27) and GG-2. Primer Pal3-3 primes specific super-integron sequence approximately 60 nucleotides from the 3' end and contains hexaguanine sequence at 5' end with an 8-oxo-guanine at the $6^{th}$ position. Primer GG-2 is poly-dG, which is complementary to the polyC tail and contains an 8-oxo-guanine at the $6^{th}$ position from 5' end. "N"—A, G, C or T; "H"—indicates A, T or C;

(c) double-stranded amplification products flanked by hexaguanine sequences on both ends and containing two 8-oxo-guanine residues per molecule which are positioned on opposite strands with respect to each other;

(d) amplified products after nicking with FPG glycosylate/ AP lyase at 8-oxo-guanine to generate 3' single-stranded extensions of six cytosines on both ends of the amplified products;

(e) the amplified products representing the unknown sequences of super-integron are inserted into the linear pUC-TT vector having 3' single-stranded extensions of six guanines thus creating recombinant molecules.

DETAILED DESCRIPTION OF THE INVENTION

Definitions

The following terms as used in the Description and in the accompanying claims have been defined below. These definitions should be applied unless the context in which the terms are used requires otherwise.

The term "single-stranded extension" as used herein refers to a single-stranded region extending from a double-stranded region of a polynucleotide molecule.

The term "polynucleotide molecule" refers to single-stranded or double-stranded DNA molecule or RNA molecule or an RNA/DNA hybrid. The polynucleotide molecule may be of any length and includes oligonucleotides, plasmids, chromosomal DNA, double-stranded RNA, mRNA/DNA hybrids, amplified DNA fragments and other naturally occurring or synthetic double-stranded nucleic acids.

The term "primer" refers to an oligonucleotide sequence which forms a substrate for polymerase-dependent amplification of a target molecule where at least part of the oligonucleotide sequence is complementary to a pre-selected sequence on one strand of a double-stranded target polynucleotide molecule. The oligonucleotide sequence may be prepared synthetically using standard techniques.

The term "target molecule" as used herein refers to a portion of a polynucleotide molecule, for example DNA, which is selected for manipulation.

The term "recipient molecule" as used herein includes a double-stranded polynucleotide molecule capable of being replicated in a host cell.

The term "linearized vector" as used herein refers to a recipient molecule that is converted into linear form or to any other non-circular DNA.

The term "recombinant molecule" as used herein refers to a polynucleotide molecule that is composed of at least two target molecules. The term also includes a circular polynucleotide molecule that is composed of a recipient molecule and at least one target molecule so that the replication of the inserted target molecule(s) in the recipient molecule may occur in a host cell.

The term "host cell" refers to any eukaryotic or prokaryotic cell, including cells from mammals, insects, yeast, bacteria or other organisms without limit.

The term "specific nicking" refers to hydrolysis of a phosphodiester bond within a polynucleotide molecule at the selected location. After specific nicking, the polynucleotide molecule is no longer continuously covalently linked at the selected location.

The term "selected location" refers to a specific sequence in a polynucleotide molecule or primer that contains at least one nucleotide, which may be a modified nucleotide.

The term "cassette" refers to a double-stranded nucleic acid. The cassette contains a pre-selected combination of at least one sequence-specific nicking site recognized by a sequence-specific nicking endonuclease and at least one sequence-specific restriction site recognized by a sequence-specific restriction endonuclease. The nicking and restriction sites in the cassette are separated from each other by a defined sequence and are ordered and oriented with respect to each other. The boundaries of the cassette in its minimum configuration are determined by the position of the nicking site and a restriction site or by the position of two nicking sites as shown in FIGS. 19-22. However, the boundaries of the cassette can be extended to incorporate non-essential nucleotide sequences outside the minimum configuration.

The term "modified nucleotide" refers to a nucleotide that is chemically distinguishable from unmodified nucleotides that occur in nature namely dA, dT, dG and dC. The modified nucleotides are further characterized by their ability to be incorporated in polynucleotide molecules in the place of unmodified nucleotide.

The term "nicking agent" refers to a reagent which is capable of both recognizing a sequence-specific target, and nicking the target at a phosphodiester bond within or in a defined relationship to such sequence-specific target. The target comprises at least one nucleotide, where the nucleotide is a modified nucleotide.

The term "artificial" refers to reagents or molecules that have been combined in vitro to achieve a particular purpose.

The use of the term "include" is intended to be non-limiting.

The term "DNA glycosylase" refers to any enzyme with glycosylase activity which causes excision of a modified nitrogenous heterocyclic component of a nucleotide from a polynucleotide molecule.

The term "single-strand cleavage enzyme" refers to (i) an AP endonuclease, lyase or other enzyme which cleaves a phosphodiester bond after an AP site is formed, or (ii) an enzyme that cleave directly at a modified nucleotide or a single-stranded region in a polynucleotide molecule.

Described below are methods and compositions relating to generation of single-stranded extensions of defined length and composition in polynucleotide molecules. Any molecular biology technique for which a specific reference has not been provided herein may be achieved following the protocols provided in Sambrook, In Molecular Cloning. Laboratory Manual 2001 (Cold Spring Harbor Laboratory Press, Cold Spring Harbor, N.Y.).

Single-stranded extensions created on polynucleotide molecules according to present embodiments of the present invention are characterized by their precise design with respect to their length and nucleotide sequence. The single-stranded extension on a polynucleotide molecule can be of any desired length with no particular limitation on the maximum length that can be produced according to embodiments of the methods described here. However, in practice, the length of the single-stranded extension is selected according to its ability to self-dissociate from a complementary strand. Consequently, the preferred length of a single-stranded extension is no greater than about 20 nucleotides, and preferably less than about 14 nucleotides. For the uses described herein, the length of the single-stranded extension should be at least about 5 nucleotides.

Creating Single-Stranded Extensions Using Cassettes

A process of generating a single-stranded extension in a polynucleotide molecule involves first inserting a cassette into a polynucleotide molecule. The cassette can be inserted into any polynucleotide molecules using, for example, restriction endonuclease cloning method or PCR amplification.

Cleavage of a polynucleotide molecule containing the cassette with the selected combination of nicking endonuclease(s) and restriction endonuclease(s) produces at least one single-stranded extension of desired length and composition. The one or more nicking endonucleases specifically nick the cassette on one nucleic acid strand only. The one or more restriction endonucleases cleave the cassette on both nucleic acid strands. Within the cassette, the location and orientation of the one or more nicking site with respect to the one or more restriction sites determines the orientation and the length of the single-stranded extensions. The length may be changed at will by incorporating a selected number of nucleotides in between the nicking site and the restriction site.

The nucleotide composition of the single-stranded extensions partially depends on the nucleotide sequence of the nicking and restriction sites present in the cassette. A significant contribution to the composition of the single-stranded extension comes from the variable nucleotide sequence incorporated in between each nicking site and restriction site. In practice, the practitioner chooses the most convenient nicking and restriction sites from those sites known in the art for incorporation into the cassette and customizes the length and composition of the nucleotide sequences in between the sites to obtain single-stranded extensions with the desired nucleotide composition.

The cassette can be designed so that a single-stranded extension may be generated on one or both ends of a cleaved polynucleotide molecule and on either the 3' or 5' terminus of the duplex. This can be achieved by selective orientation of the nicking sites with respect to the restriction site in the cassette. Since nicking endonucleases cleave only one strand at a double-stranded nicking site, the orientation of the site determines whether the top or the bottom strand is nicked. The terminal sequence flanked by the nick self-dissociates from the complementary strand because the nick is introduced close to the double-strand break caused by restriction endonuclease. After self-dissociation, the polynucleotide molecule is left flanked by either a 5' or 3' single-stranded extension according to which strand is nicked.

The design of cassette for generation of single-stranded extensions on a polynucleotide molecule is flexible. The flexibility arises from the options available for arranging the order, orientation and spacing of the nicking site(s) with respect to adjacent restriction site(s). The preferred length of the cassette is greater than 5 nucleotides. Where a spacer region is present between two restriction sites, there is no upper limit on the length of the cassette. In the presence of one restriction site only, the upper limit on the length of the cassette is determined by the ability of the terminal nicked strand to self-dissociate from the un-nicked strand.

What has been generally described above is here described in more specific detail. Optional configurations of a cassette are exemplified in FIGS. 1-6.

Figure 1:
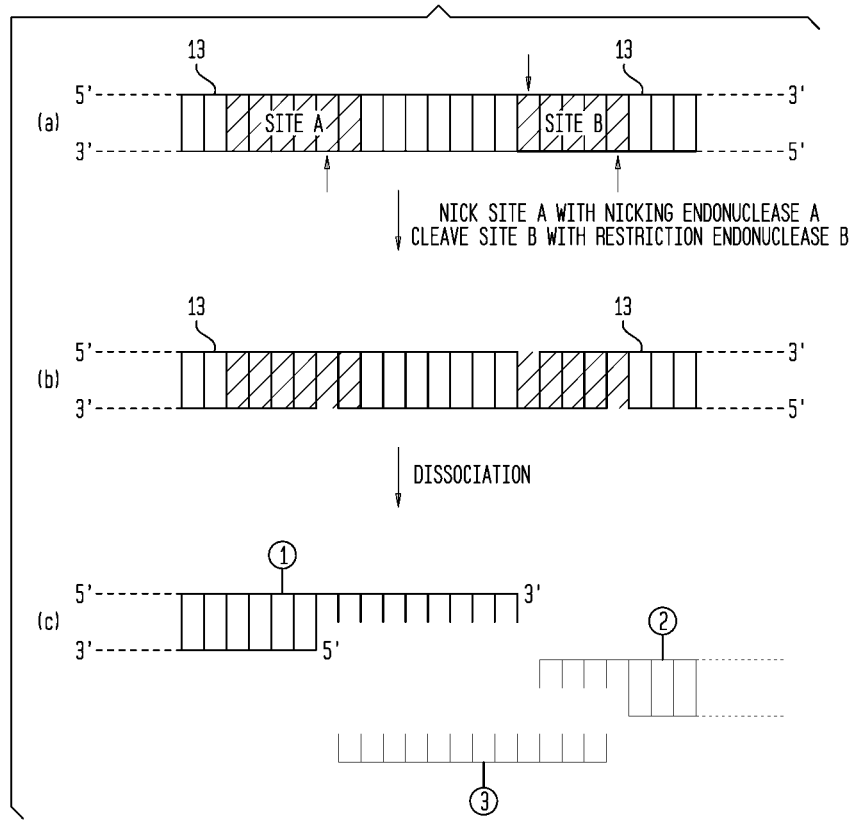
FIG. 1 shows how a 3' single-stranded extension of desired length and composition is generated on the left-side of a cleaved polynucleotide molecule.

FIGS. 1, 2 and 5 show how the cassettes may be designed to produce 3' or 5' single-stranded extension on a selected end of a polynucleotide molecule. FIG. 1 depicts a cassette where the nicking site is upstream of the restriction site and in an orientation that allows nicking of the bottom strand. Double-digestion of a polynucleotide molecule containing the cassette with restriction and nicking endonucleases generates a 3' single-stranded extension on the left-side fragment of polynucleotide molecule. Alternatively, a 3' single-stranded extension on the right-side fragment of polynucleotide molecule can be generated, when the nicking site is placed downstream of the restriction site and is inverted to provide top-strand nicking (FIG. 2). Similarly, a 5' single-stranded extension can be generated on the right or left fragment (FIG. 5).

FIGS. 3, 4 and 6 show how cassettes can be designed to generate single-stranded extensions of desired length and composition on both ends of a polynucleotide molecule. Accordingly, the cassette includes two inversely-oriented nicking sites located on either side of a single restriction site (FIG. 3) or on either side of two restriction sites where these sites may be the same (FIG. 4) or different (FIG. 6) to yield two single-stranded extensions. The cassettes depicted in FIGS. 3 and 4 show two nicking sites of the same nicking endonuclease: Site A and inverted Site A both are recognized by nicking endonuclease A and opposite strands are nicked because of the inverted orientation of the sites. It is also possible to use of two non-identical nicking sites recognized and nicked by two distinct nicking endonucleases. Similarly, the cassettes in FIGS. 4 and 6 may include two non-identical restriction sites assuming that the recognition sequences provide the desired nucleotide composition for generation of single-stranded extensions. For example, FIGS. 5 and 6 depicts cassettes containing nicking site(s) for a nicking endonuclease C and a restriction site for restriction endonuclease D whereas in FIGS. 1 to 4, sites A and B are shown.

A cassette such as that shown in FIG. 3 may be modified to include an additional spacer sequence (FIG. 6). Cleavage with the restriction endonuclease and nicking endonuclease results in removal of the spacer sequence and generating single-stranded extensions identical to those in FIG. 3. An advantage of introducing a spacer sequence into the cassette is to provide a nucleotide sequence which codes for a selectable marker. The presence of the selectable marker enables differentiation between cleaved and non-cleaved cassettes in a transformed host cell. Examples of selectable markers include toxins, drug-resistant factors, enzymes, antigens, fluorescent and chemiluminescent markers, and siRNA.

Nicking sites include any sequences that are specifically recognized and nicked by nicking endonuclease. The sequence of the nicking site encompasses the sequence at which the endonuclease binds and the sequence at which it cleaves, be it within the recognition site or outside the recognition site. Any nicking endonuclease which nicks within its recognition site or at a distance from their recognition site may be utilized. Examples include nicking endonuclease N.BstNBI which recognizes and nicks GAGTCNNNN↓; N.BbvCIB which recognizes and nicks CC↓TCAGC; N.BbvCIA which recognizes and nicks GC↓TGAGG; N.AlwI which recognizes and nicks GGATCNNNN←; and N.Bpu10I which recognizes and nicks GC←TNAGG (U.S. Pat. No. 6,395,523 and EPO Grant No. 1 176 204). Included here is the use of any nicking endonuclease derived from modification of a Type II restriction endonuclease, for example, by methods discussed in International Application No. PCT/US02/26273 and U.S. application Ser. No. 09/738,444.

Restriction sites include any sequences that are specifically recognized by restriction endonucleases. The restriction site encompasses the sequence at which the endonuclease binds and the sequence at which it cleaves be it within the recognition site or outside the recognition site. Examples of restriction endonucleases include any of the restriction endonucleases listed in REBASE® (www.NEB.com).

The polynucleotide molecules for which single-stranded extensions of desired length and composition may be created include recipient molecules which further include circular vectors and linear molecules such as genomic DNA or fragments of DNA. Using a single-stranded extension on a polynucleotide molecule which is complementary to a single-stranded extension on another polynucleotide molecule, two or more polynucleotide molecules may be joined to form a single molecule. For example, a target DNA molecule may be inserted into a recipient molecule using complementary single-stranded extensions.

Single-stranded extensions on the recipient molecule may be created by first inserting a cassette into the recipient molecule. The cassette is subsequently cleaved with an appropriate combination of restriction endonuclease(s) and nicking endonuclease(s) to generate a linearized recipient molecule having single-stranded extensions of desired length and composition on both ends.

Recipient molecules with 3' or 5' single-stranded extensions permit insertion of polynucleotide molecules (target molecules) which have complementary single-stranded extensions to form recombinant molecules. The recombinant molecules can be replicated in a transformed host cell.

The generation of linearized recipient molecules with 3' single-stranded extensions of desired length and composition is simple to perform and has advantages which include: (a) single-stranded extensions may be of any desired length, i.e. longer than those produced by cleavage with restriction endonuclease; (b) single-stranded extensions can be designed to be non-self-complementary, that is they are not complementary to each other, so that recipient molecule termini do not re-anneal to form transformable circular DNA; and (c) each single-stranded extension may be designed to carry a unique nucleotide sequence, thereby permitting control of the orientation of the inserted target molecule. Examples of recipient molecules containing cassettes designed to create different 3' single-stranded extensions are provided in Example I and FIGS. 19-22 and FIG. 27 and include plasmid vectors pNEB200A, pNEB205A, pNEB210A and pUC-TT (New England Biolabs, Inc., Beverly, Mass.).

In particular, the cassette in vector pNEB205A (FIG. 19) carries two N.BbvCIB nicking sites, which are separated by a single XbaI restriction site. The N.BbvCIB and XbaI sites are arranged in such a way that digestion of the recipient molecule with the above specified enzymes provides a linearized vector flanked by 8-nucleotide long single-stranded extensions, GGGAAAGT-3' and GGAGACAT-3', on the ends. The cassette in vector pNEB200A (FIG. 20) carries two N.BstNBI nicking sites, which are separated by two XbaI restriction sites. The N.BstNBI and XbaI sites are arranged in such a way that digestion of the recipient molecule with the above specified enzymes provides a linearized vector flanked by 8-nucleotide long single-stranded extensions, ACGAGACT-3' and ACCAGACT-3', on the ends. The cassette in vector pNEB210A (FIG. 21) carries two N.BbvCIB nicking sites, which are separated by XbaI and BamHI restriction sites. The N.BbvCIB, XbaI and BamHI sites are arranged in such a way that digestion of the recipient molecule with the above specified enzymes provides a linearized vector flanked by 6-nucleotide long single-stranded extension of GGGGGG-3' on one end and 8-nucleotide long single-stranded extension of GGAGACAT-3' on the other end. The cassette in vector pUC-TT (FIG. 22) carries two N.BbvCIB nicking sites, which are separated by two BamHI restriction sites. The N.BbvCIB and BamHI sites are arranged in such a way that digestion of the recipient molecule with the above specified enzymes provides a linearized vector flanked by 3' single-stranded extensions of 6-guanines on both ends.

Although specific examples of cassettes are provided above for generating single-stranded extensions, a variety of restriction sites and/or nicking sites can be used to generate the same single-stranded extensions. For example, restriction sites for either BspHI (T↓CATGA) or BspEI (T↓CCGGA) or BclI (T↓GATCA) or BsrGI (T↓GTACA) may substitute for the XbaI site to create the identical single-stranded extension shown in FIG. 20. Nicking sites for N.AlwI or N.BbvCIA may be used in place of either N.BstNBI or N.BbvCIB sites for alternative sites. The choice of restriction and nicking sites is limited only by considerations of the intended use of the resultant single-stranded extensions.

Generation of Single-Stranded Extensions Using a Nicking Agent

An alternate method of generating 3' single-stranded extensions from that described above involves primer dependent amplification of target molecules where the primers contain a modified nucleotide at a specific site. The amplification product is treated with a nicking agent that nicks specifically at the modified nucleotide. Dissociation of the nicked single-stranded terminal region from complementary strand generates a single-stranded extension. Examples of primer-dependent amplification include: Polymerase Chain Reaction (PCR), Strand Displacement Amplification (SDA), Transcription-Mediated Amplification (TMA) and Ligase Chain Reaction (LCR).

The use of modified nucleotides incorporated into amplification fragments provide the following advantages: (a) the length of the specific nick site may be as short as one nucleotide; (b) the modified nucleotide may be incorporated at the pre-selected location in target molecule and represents a unique target for nicking; and (c) any individual modified nucleotide out of a number of different types of modified nucleotides can be incorporated into each of several locations in the same or several different target molecules thus creating a plurality of unique specific nicking sites.

Examples of modified nucleotides for incorporation into target molecules include deoxyuridine (U), 8-oxo-guanine (8oxoG), 5,6-dihydrothymine, thymine glycol, uracil glycol, 5-hydroxymethylcytosine, 5-hydroxymethyluracil, 7-methyladenine, 7-methylguanine, hypoxanthine, xanthine and others. Incorporation of modified nucleotides at the selected locations of target molecule may be achieved by means well known to those skilled in the art that include either chemical or enzymatic synthesis of polynucleotide molecule (Piccirilli et al. *Nature* 343:33-37 (1990); Purmal et al. *Nucl. Acid. Res.* 22:72-78 (1994); Horlacher et al. *Proc. Natl. Acad. Sci. USA* 92:6329-6333 (1995); Kamiya et al. *Nucl. Acid. Res.* 23:2893-2899 (1995); Lutz et al. *Nucl. Acid. Res.* 24:1308-1313 (1996); Zhang et al. *Nucl. Acid. Res.* 25:3969-3973 (1997); Hill et al. *Nucl. Acid. Res.* 26:1144-1149 (1998); Liu, et al., *Nucl. Acid. Res.* 26:1707-1712 (1998); Berdal et al. *EMBO J.* 17:363-367 (1998); Purmal et al. *J. Biol. Chem.* 273:10026-10035 (1998); Lutz et al. *Nucl. Acid. Res.* 27:2792-2798 (1999); Duarte et al. *Nucl. Acid. Res.* 27:496-502 (1999); Pourquier et al. *J. Biol. Chem.* 274:8516-8523 (1999); Kamiya, et al., *Nucl. Acid. Res.* 28:1640-1646 (2000); Duarte et al. *Nucl. Acid. Res.* 28:1555-1563 (2000)).

In one embodiment, a single-stranded oligonucleotide containing at least one modified nucleotide may be synthesized in vitro by means that include chemical synthesis. Chemically synthesized oligonucleotide molecules may be used as primers for amplification of a sequence in a target molecule. In one aspect of the embodiment, a modified nucleotide may be incorporated into a primer sequence close to its 5' end, for example the modified nucleotide may be incorporated at a distance of 2 to 20 nucleotides from the 5' end. The 5' end of primer sequence upstream of the modified nucleotide may not necessarily anneal to the sequence of the target molecule; instead it may contain a custom designed sequence which is complementary to the 5' region of another polynucleotide molecule. In these circumstances, the primer sequence downstream of the modified nucleotide is complementary to a selected region of the target molecule allowing the enzymatic extension, copying the target molecule onto the 3' end of primer sequence. Other considerations of primer design, for example such as the length of priming sequence and the melting temperature, are well known to the art (Sambrook, J. in: Molecular Cloning. Laboratory Manual, pp. 8.13-8.16 (2001) Cold Spring Harbor laboratory Press. Cold Spring Harbor, N.Y.).

Primer sequences containing at least one modified nucleotide become incorporated into a double-stranded target molecule otherwise lacking such modified nucleotides by multiple rounds of enzymatic DNA copying, for example, by primer extension, by Polymerase Chain Reaction (PCR) dependent DNA amplification or by other primer dependent amplification means such as Strand Displacement Amplification (SDA). Methods and conditions for either primer extension or amplification are widely known in the art (see for example U.S. Pat. Nos. 4,683,195; 4,683,202; 5,333,675; Sambrook, J. in: Molecular Cloning. Laboratory Manual, pp. 8.4-8.29 (2001) Cold Spring Harbor laboratory Press. Cold Spring Harbor, N.Y.). Preferably, the DNA polymerase utilized in the DNA copying reaction is one that incorporates the correct nucleotide opposite the modified nucleotide in at least 50% of product molecules. Since primer sequences, but not the target molecule, define the 5' ends of the amplified molecule, the target molecule after amplification may be extended by an additional sequence at least on one end, and may carry a modified nucleotide at the junction between target sequence and the additional sequence.

The amplified target molecule can be specifically nicked at the location(s) of the modified nucleotide(s) using a modified nucleotide-specific nicking agent. Where the modified nucleotide is incorporated close to the 5' end of the target molecule, the 5' terminal single-stranded region flanked by the nick may dissociate from the complementary strand, leaving behind a double-stranded target molecule flanked with at least one 3' single-stranded extension.

Specific nicking of the target molecule at the location(s) of the modified nucleotide(s) may be achieved by selectively cleaving one or more of the phosphodiester bonds next to the incorporated modified nucleotide(s) using physical, chemical or enzymatic means or combinations of the such cleavage means.

Nature has produced a wide variety of enzymes which cumulatively respond to multiple insults on a polynucleotide molecule. Some of these insults result in modified nucleotides, and various enzymes are responsible for their repair. For example, DNA N-glycosylases excise the modified nitrogenous heterocyclic component of the nucleotide, while AP endonucleases cleave phosphodiester bonds next to the abasic (AP) sites and DNA glycosylases/AP lyases achieve both of these functions. In certain embodiments of the invention, enzymes that are capable of excising modified heterocyclic bases of modified nucleotides with specificity have been selected in various unnatural combinations to form nicking agents for use in generating single-stranded extensions on amplified DNA fragments.

Examples of repair enzymes include:

(A) DNA N-glycosylases include the following enzymes and their homologues in higher eukaryotes including human homologues: Uracil DNA glycosylase (UDG) and 3-methyladenine DNA glycosylase II (AlkA) (Nakabeppu et al. *J. Biol. Chem.* 259:13723-13729 (1984); Varshney et al. *J. Biol. Chem.* 263:7776-7784 (1988); Varshney et al. *Biochemistry* 30:4055-4061 (1991)). Additional DNA N-glycosylases include TagI glycosylase and MUG glycosylase (Sakumi, et al. *J. Biol. Chem.* 261:15761-15766 (1986); Barret, et al. *Cell* 92:117-129 (1998)).

(B) AP endonucleases include Endonuclease IV of *E. coli* and its homologues in higher eukaryotes including human homologue hAP1 (Ljungquist *J. Biol. Chem.* 252:2808-2814 (1977); Levin et al. *J. Biol. Chem.* 263:8066-8071 (1988); Saporito et al. *J. Bacteriol.* 170:5141-5145 (1988); Robson, et al., *Nucl. Acid. Res.* 19:5519-5523 (1991); Demple et al. *Proc. Natl. Acad. Sci. USA* 88:11450-11454 (1991); Barzilay et al. *Nucl. Acid. Res.* 23:1544-1550 (1995)).

*E. coli* Endonuclease V and homologues cleave DNA at a second phosphodiester bond 3' to the lesion, where the lesion may be selected from any of: deoxyinosine, deoxyuridine (U), AP sites, base mismatches as well as loops, hairpins, Flap and Pseudo-Y DNA structures (Yao, et al., *J. Biol. Chem.* 272:30774-30779 (1997); He et al. *Mutation Research* 459: 109-114 (2000)).

(C) DNA glycosylases/AP lyases excise selected modified nucleotides and include the following enzymes and their homologues in higher eukaryotes including human homologues:

(i) enzymes which are capable of specifically recognizing and excising oxidized pyrimidines include *E. coli* Endonuclease VIII (EndoVIII), *E. coli* Endonuclease III (NTH) and its homologues in *S. cerevisiae* (NTG1 and NTG2) and human (hNTH1) (Mazumder et al. *Biochemistry* 30:1119-1126 (1991); Jiang et al. *J. Biol. Chem,* 272:32230-32239 (1997); Harrison et al *Nucl. Acid. Res.* 26:932-941 (1998); Senturker et al. *Nucl. Acid. Res.* 26:5270-5276 (1998));

(ii) enzymes which are capable of specifically recognizing and excising oxidized purines include *E. coli* FAPY-DNA glycosylase (FPG) and its human homologues hOGG1 and hOGG2 (Boiteux EMBO J. 6:3177-3183 (1987); Boiteux et al. *J. Biol. Chem.* 265:3916-3922 (1990); Tchou, et al., *J. Biol. Chem.* 270:11671-11677 (1995); Radicella et al. *Proc. Natl. Acad. Sci. USA* 94:8010-8015 (1997); Vidal et al. *Nucl. Acid. Res.* 29:1285-1292 (2001)); and (iii) enzymes which are specific for UV-induced cyclobutane pyrimidine dimers include T4 endo V (Gordon, et al., *J. Biol. Chem.* 255:12047-12050 (1980); Seawell et al. *J. Virol.* 35:790-796 (1980)).

Certain other embodiments of the invention take advantage of the specific functionalities of repair enzymes by creating mixtures of components that include at least one enzyme that has the desired effect of recognizing a particular modified nucleotide and excising the modified base (specificity component) and at least one enzyme that selectively cleaves phosphodiester bond(s) adjacent to the abasic nucleotide (nicking component). The specificity of the mixtures in achieving the function of specific phosphodiester bond(s) nicking at the specifically modified nucleotides is distinct from the functional specificity of individual components where the specificity component is not able to achieve the function of the nicking component and vice versa. In general, the activity of the specificity component with respect to the nicking component in the nicking agent should be at least 2:1.

Examples of enzymes which have the specificity function, but lack the AP-site nicking function include DNA N-glycosylases. Examples of enzymes which have the nicking function but lack the specificity function include the AP endonucleases. An artificial nicking agent may be created by combining a DNA N-glycosylase and an AP endonuclease, for example by combining UDG glycosylase with EndoIV endonuclease or AlkA glycosylase with EndoIV endonuclease to achieve single-stranded cleavage at a modified nucleotide.

The choice of which components should be combined in the nicking agent to achieve single-stranded cleavage at a modified nucleotide depends on (a) the type of modified nucleotide to be excised (because this determines the selection of the specificity component) and (b) the type of strand terminus desired at the nick location after the excision of modified nucleotide which affects the choice of nicking component.

For example, an artificial nicking agent comprised of AlkA glycosylase and EndoIV endonuclease has a specificity for deoxyinosine and has nicking activity which results in a 5' terminal deoxyribose phosphate (broken sugar) and a 3' hydroxyl group at the nick location.

For nicking at a deoxyuridine (U) and generating a 5' broken sugar and a 3' hydroxyl group at the nick location, an artificial nicking agent that contains UDG glycosylase as a specificity component and EndoIV endonuclease as a nicking component may be created.

Under certain circumstances, it may be desirable to generate a 5' phosphate at the nick location in place of the 5' broken sugar described above. Accordingly, a nicking agent may be formulated with the above described specificity component but with a nicking component that leaves 5' phosphate at the nick location. Examples of nicking components with this nicking activity include the lyase activity of DNA glycosylases/APyases, such as EndoVIII DNA glycosylase/AP lyase or FPG DNA glycosylase/AP lyase which generate 5' phosphate and 3' phosphate at the nick location. Consequently, the newly formulated nicking agent for nicking the target molecule at deoxyinosine might consist of a combination of AlkA glycosylase and EndoVIII glycosylase/AP lyase or FPG glycosylase/AP lyase. Alternatively, the newly formulated nicking agent for nicking a target molecule at a deoxyuridine (U) might include a combination of UDG glycosylase and EndoVIII glycosylase/AP lyase or FPG glycosylase/AP lyase.

Under certain circumstances, it may be desirable to create a 5' phosphate and a 3' hydroxyl group at the nick location using the above described specificity component. For example, a combination of UDG glycosylase, EndoIV endonuclease and EndoVIII glycosylase/AP lyase creates an artificial nicking agent that specifically nicks the target molecule at deoxyuridine (U) generating a single nucleotide gap and leaving 5' phosphate and 3' hydroxyl at the nick location.

In certain embodiments of the invention, different types of modified nucleotides may be introduced at a plurality of selected locations in order to nick target molecule(s) sequentially at two or more locations. For example, a deoxyuridine (U), an 8-oxo-guanine, and a deoxyinosine may be introduced into the selected locations of the target molecule(s). A single nicking agent may be formulated that includes more than one specificity component according to the incorporated modified nucleotides. Alternatively separate nicking agents may be formulated and applied to the target molecule(s) sequentially. For example, AlkA and FPG glycosylase/AP lyase which selectively nicks at a deoxyinosine and deoxy 8-oxo-guanine may be combined or used sequentially with a nicking agent that contains UDG and EndoVIII glycosylase/AP lyase that selectively nicks at a deoxyuridine (U).

The present embodiment of the invention is further illustrated by Example II, showing preparation of two new nicking agents referred to as the USER™ Enzyme, which specifically nicks target molecules at deoxyuridine (U), and the USER™ Enzyme 2, which specifically nicks target molecules at both deoxyuridine (U) and 8-oxo-guanine both leaving a 5' phosphate at the nick location.

Applications

A prominent feature of the methods described herein is the universality and flexibility of the approach for allowing the performance of a wide range of DNA manipulations singly or together. The universality and flexibility of these methods distinguishes them from traditional systems, such as restriction endonuclease-dependent cloning or manipulation, which require laborious step-by-step experiments to perform multiple manipulations.

Examples of some uses for the present methods include:

A) Directional cloning of PCR products (exemplified in FIG. 7);

B) Site-specific mutagenesis including nucleotide or nucleotide sequence substitution, insertion, deletion or fusion (exemplified in FIGS. 8-12);

C) Assembly of target molecules from the plurality of intermediate fragments (exemplified in FIGS. 13-15);

D) Directional assembly of multiple target molecules into recipient molecules (exemplified in FIG. 16);

E) Chromosomal/Enviromental DNA cloning outside the boundaries of known sequence (chromosome walking) (exemplified in FIG. 17);

F) Construction of cDNA libraries, which may also include cloning of cDNA beyond the boundaries of known sequences (exemplified in FIG. 18); and G) Concurrent use of the above applications (exemplified in FIGS. 35-37.

A) Directional Cloning of PCR Products

Complementary single-stranded extensions can be generated on a linearized recipient molecule and in a PCR product, where the extensions of each can anneal with the other to produce a recombinant molecule capable of being introduced into competent host cells (FIG. 7).

(1) Generation of single-stranded extensions on recipient molecules includes construction of a recipient molecule carrying a cassette for producing 3' single-stranded extensions of desired length and composition on each ends of the linearized recipient molecule (discussed above).

(2) Generating single-stranded extensions on a PCR fragment includes incorporation of specifically-modified nucleotides at selected positions in the PCR fragment as described above, and nicking the fragment at the modified nucleotide with a specific nicking agent and dissociating the nicked 5' terminal oligonucleotide from the complementary strand to produce a fragment having single-stranded extensions of desired length and composition.

The primers may carry nucleotide sequences at their 5' ends that do not anneal to the desired target. These 5' sequences are chosen to be identical to the single-stranded extensions on the linearized recipient molecule, except for a terminal 3' nucleotide, which in the primer sequences is replaced by a modified nucleotide X (FIG. 7). Downstream of the modified nucleotide, the primer sequences are complementary to a target molecule specific sequence to enable extension by polymerase.

Amplification of target sequence is then performed using a pair of such primers. After amplification, each end of the target molecule has been extended by the additional sequence.

The resulting amplification product is then treated with a nicking agent, which specifically recognizes and nicks DNA at the locations of modified nucleotides. After phosphodiester bond breakage, the 5' terminal single-stranded regions beyond the nicks dissociate from the complementary strand, leaving the target molecule flanked by 3' single-stranded extensions. The 3' single-stranded extensions generated are complementary by design to the single-stranded extensions on the linearized recipient molecule, therefore, when mixed together, the linearized recipient molecule and target molecule assemble into a recombinant molecule (FIG. 7). Since the single-stranded extensions can be designed to be long enough to produce stable recombinant molecules, covalent linking of DNA molecules by ligation is not always necessary. The recombinant molecule can then be introduced into competent host cells by transformation and can be replicated.

FIG. 26 shows how unique 3' single-stranded extensions were created on a target molecule which was then annealed to complementary 3' single-stranded extensions on the linearized vector pNEB205A (see Example IA). This was achieved by using a pair of primers containing a deoxyuridine as a modified nucleotide for amplification of the target DNA and using USER™ Enzyme (see Example II) for nicking at the deoxyuridine (U).

FIG. 26A shows primers having specific 8 nucleotide-long extensions at their 5' ends and which were selected to be identical to single-stranded extensions on the vector pNEB205A (FIG. 19), except for the replacement of a 3' thymine with a deoxyuridine (U). In the presence of natural dNTPs, Taq DNA Polymerase incorporates adenine opposite U resulting in a double-stranded molecule which is extended on both ends by 8 base pairs and which contains primer-derived single U at each junction with the target molecule sequence (FIG. 26B).

In FIG. 26B, after nicking with USER™ Enzyme, the terminal single-stranded hepta-nucleotide dissociates from the target molecule leaving the target molecule flanked by 3' single-stranded extensions of 8-nucleotides in length. The recipient molecule, (pNEB205A) and the USER™ Enzyme-treated target molecule assemble into a recombinant molecule by means of the complementary 3' single-stranded extensions. Because of the length of the extensions, ligation is not required. The construct was used to transform chemically-competent E. coli cells.

The present application is further illustrated by the Example III showing the preparation of a kit for directional cloning of PCR products by uracil excision. The efficiency of the present method is further illustrated by Example IV which shows that on average, $10^5$ desired recombinants can be obtained per 20 ng of linear vector pNEB205A, and 94-95% cloning efficiency may be achieved within a wide range of PCR product concentration (when the host cell competency is $2\times10^7$ c.f.u./μg DNA).

B) Site-Specific Mutagenesis: Nucleotide or Nucleotide Sequence Substitution, Insertion, Deletion or Fusion Complementary single-stranded extensions of desired length and composition can be generated on the ends of at least two polynucleotide molecules. The polynucleotide molecules can then anneal via the single-stranded extensions to form a single target molecule (FIG. 8). This approach forms the basis for a wide variety of DNA manipulations, such as site-specific mutagenesis, deletions, insertions, gene fusions or replacement of any DNA segment virtually at any position of the target molecule, and can also be applied to assembly of target molecules from multiple DNA fragments with any combination of the above carried out concurrently.

In FIG. 8, the polynucleotide molecule is identified as a target molecule which is amplified as two overlapping intermediate fragments in separate amplification reactions that utilize two different sets of amplification primers referred to as primer pair (P1/P4) and primer pair (P2/P3).

The P1 and P2 primers, although used in separate amplification reactions for priming the opposite strands of the target molecule, overlap each other by a short nucleotide sequence such as 2 to 20 nucleotides. In addition, each overlapping primer contains one modified nucleotide which flanks the overlap region on the 3' side. Selection of the priming site of P1 and P2 primers, and thereby the overlap sequence shared by the P1 and P2 primers, will depend on where the desired manipulation of target molecule is to take place. The predetermined sequence changes that achieve the desired manipulation are incorporated into the Primer P1 and P2 sequences.

The outside Primers P3 and P4 may prime target molecules at locations that enable amplification of the entire desired region of target molecule. The features of the outside primers are discussed in more detail later when describing the subcloning of the assembled target molecules into recipient molecules.

Target molecule amplification is then performed using both sets of primers and when completed, both amplified fragments carry an identical copy of the overlap sequence, except that one fragment contains the modified nucleotide on the top strand of the overlap, while the other fragment contains modified nucleotide on the bottom strand of the overlap (FIG. 8 (b)).

Generation of single-stranded extensions on the amplified target fragments may be achieved by nicking at the modified nucleotides using a modified nucleotide-specific nicking agent. The single-stranded extensions generated on the two fragments are complementary to each other, since they are created from the overlap sequence. Thereby, the amplified intermediate fragments may be directionally assembled to yield a full-length target molecule and thereafter may be covalently linked by ligation (FIG. 8 (d)). Ligation prevents the assembled target molecules from dissociating. In general, ligation is necessary only if the target molecule is to be subjected to traditional subcloning methods, such as restriction endonuclease-based cloning methods.

An advantage of this approach is the avoidance of side-products that include the following: (a) because the single-stranded extensions do not contain two-fold axis of symmetry, the amplified fragments cannot assemble/ligate upon themselves; (b) because of the single nucleotide/gap, the short oligonucleotide released after modified nucleotide excision cannot ligate back to the parental strand; and (c) because the primers used to amplify target fragments are not phosphorylated. Ligation in amplified fragments in any other orientation is not possible. Instead, a 5' phosphate is exceptionally generated at the location of excision of the modified nucleotide. Thus providing the only substrate for DNA ligase.

The assembled final product, comprising the full-length target molecule, may then be subcloned into a recipient molecule of choice using, for example, a restriction endonuclease based cloning method known in the art. For this purpose, the outside Primers P3 and P4 may be designed to contain the unique restriction sites. After the assembly of target fragments is accomplished, the full-length product is then subjected to digestion with restriction endonucleases, the sites for which have been incorporated into the Primer P3 and P4 sequences, and thereafter the product is ligated into the recipient molecule which is pre-cleaved with the same or compatible restriction endonucleases. An alternative approach to Primer P3 and P4 design is described below in (d). In this protocol, ligation is not used because the manipulated fragments are assembled directly into the recipient molecule without the need for a restriction endonuclease-dependent cloning step.

The general approach described above has numerous applications some of which are described below.

(a) Site specific mutagenesis, including nucleotide substitution, can be achieved, for example by following the approach illustrated schematically in FIGS. 9A and 9B where the overlapping Primers P1 and P2 have been specifically designed for the purpose of introducing specific nucleotide(s) changes into a target molecule.

The desired nucleotide changes may be introduced into the overlapping Primers P1 and P2 either within the overlap sequence, as shown in FIG. 9A, or downstream from the overlap sequence of either primer, as shown in FIG. 9B. During amplification, these nucleotide changes are readily incorporated into intermediate target fragments. The resulting intermediate fragments are then treated with a nicking agent to remove modified nucleotides and to create complementary single-stranded extensions thereby permitting the subsequent assembly of target fragments. The reconstituted full-length target molecule, however, differs from the parental target molecule, as it carries the newly introduced nucleotide changes. The assembled mutagenized target molecule may then be subcloned following the cloning protocol of choice. A detailed working example of this approach is provided in Examples V and VI and FIG. 32.

The above approach makes it possible to achieve site-specific mutagenesis in virtually any location in the target molecule, since the priming sites may be selected anywhere along the sequence of the target molecule.

(b) Nucleotide sequence insertion can be achieved using the general methods described above. An example of how overlapping Primers P1 and P2 can be designed to achieve nucleotide sequence insertion is illustrated schematically in FIG. 10. Overlapping Primers P1 and P2 may be designed for purposes of inserting a nucleotide sequence of any desired length within the limits of oligonucleotide synthesis used to synthesize a specific primer. The desired nucleotide sequence can be inserted into any desired location in the target molecule.

As shown in FIG. 10, any of the nucleotide insertion sequences not present in the target molecule may be introduced at the 5' ends of the overlapping Primers P1 and P2. The overlap region may be created either from the entire additional sequence as shown in FIG. 10A or from the 5' terminal portion of the additional sequence as shown in FIG. 10B. During amplification, the intermediate target fragments are extended by this additional sequence and are flanked by the identical copy of the overlap sequence. The resulting amplification products are then treated with nicking agent to nick at the modified nucleotides and to create complementary single-stranded extensions thereby permitting the subsequent assembly of intermediate target fragments into a full-length target molecule. The assembled full-length target molecule contains the insertion sequence and can then be cloned by following the cloning protocol of choice. This approach enables any nucleotide sequence segment, such as a unique restriction site(s) or a polylinker sequence to be introduced virtually at any position of the target molecule.

(c) Deletion of nucleotide sequences can be achieved using the general methods described above. An example of how overlapping Primers P1 and P2 can be designed to achieve nucleotide sequence deletion is illustrated schematically in FIG. 11. Overlapping Primers P1 and P2 can be designed for purposes of precisely deleting a particular nucleotide sequence segment from the target molecule.

The overlapping Primers P1 and P2 may prime distant locations on the target molecule precisely adjacent to the targeted deletion region. The 5' ends of the primers must share a common overlapping sequence. To create this overlap, the 5' end of one primer is supplemented by an additional sequence, which is a reverse-complement to the 5' end of the other primer. During amplification, one of the two amplified fragments is extended by this additional sequence. Since the additional sequence is identical to the 5' end of the other amplified fragment, the two distant target fragments now share the common overlap region. The resulting intermediate target fragments are then treated with nicking agent to remove modified nucleotides and to create complementary single-stranded extensions thereby permitting the subsequent assembly of target fragments. The resulting target molecule sequence is deficient in the precisely-deleted nucleotide sequence segment. The assembled mutagenic target molecule may then be subcloned by following the cloning protocol of choice.

The applications in (b) and (c) above are further illustrated by Examples V and VII and FIG. 33 showing the creation of two restriction sites and the deletion of 18-bp segment from the vector pUC19.

(d) Nucleotide sequence fusion can be achieved using the general methods described above. An example of how overlapping Primers P1 and P2 can be designed to achieve nucleotide sequence fusion is illustrated schematically in FIG. 12. Overlapping Primers P1 and P2 may be designed when desired to precisely join two distinct target molecules.

To create the common overlap region between two distinct target molecules, one of the overlapping primers is supplemented by an additional sequence that is reverse-complementary to the 5' sequence of the other overlapping primer. Except for the complementary overlap sequence at the 5' end, the two primers are distinct with 3' regions enabling them to prime the respective targets. Optionally, the amplification reactions may be performed using two different templates (FIG. 12). During amplification, one of the two target molecules is extended at its 5' end by the additional sequence. Since the additional sequence is identical to the 5' end of the other target molecule, the two distinct target molecules now share the common overlap region. The resulting target molecules are then treated with nicking agent to nick at the modified nucleotides and to create complementary single-stranded extensions which can re-associate to permit assembly of the distinct target molecules. Upon ligation, two target molecules are precisely linked through complementary single-stranded extensions. The chimeric full-length product may then be subcloned by following the cloning protocol of choice.

An advantage of this approach is that it provides the opportunity to create a fusion of two target molecules virtually at any desired location without introducing undesired nucleotides into the final construct. This application is further illustrated by the example showing the construction of a gene fusion of *E. coli* Endonuclease VIII and Mxe Intein (see Examples V and VIII and FIG. 34).

C) Assembly of Target Molecule from a Plurality of Intermediate Fragments

FIGS. 13-15 present schematic illustrations of the overlapping Primers P1 and P2 which may be designed when desired to precisely assemble a target molecule from more than two intermediate fragments.

For example, multiple pairs of overlapping primers may be designed where the first pair of primers overlaps across the expected junction of target molecules A and B and the second pair of primers overlaps across the expected junction of target molecules B and C. (FIG. 13). The principles of design for individual pairs of overlapping primers are similar to those outlined above in FIG. 12, where one primer at its 5' end is supplemented by an overlap sequence that is reverse-complement to the 5' end of the other primer. Since each overlap contains a unique sequence, the single-stranded extensions generated on individual PCR fragments may be linked only in one final combination, for example, targets A, B and C will be assembled into a combination ABC only.

An advantage of the embodiments of the invention is that the method provides a means to achieve multiple DNA manipulations in one experimental step. Each set of overlapping primers may carry the pre-selected nucleotide sequence changes necessary to perform such manipulations. This is further illustrated in Example IX showing the construction of the hincIIQ138A mutant gene which was achieved by simultaneous construction of a gene fusion of this gene with the Mxe intein and insertion of the whole into the promoter region of the pTXB1 vector. (see Examples V and IX; FIG. 35).

By designing an additional pair of primers which overlap across the expected junction of the first and the last targets, a circular molecule may be generated. For example, recipient molecules may be created from the multiple intermediate components (FIG. 14).

By designing multiple pairs of overlapping primers where each pair of the overlapping primers overlaps across the expected junction of the neighboring exons, the eukaryotic genes may be assembled directly from the genomic DNA (FIG. 15). This strategy is further illustrated by the Example showing an assembly of hAP1 gene from Human genomic DNA performed concurrently with silent mutagenesis (see Example X; FIG. 36).

D) Directional Assembly of Multiple Target Molecules into Recipient Molecules

FIG. 16 shows a schematic illustration of how directional assembly of multiple target molecules into a recipient molecule can be achieved.

For example, to assemble multiple intermediate fragments, pairs of overlapping primers are designed according to (B) or (C) above. However, the outside primers, instead of coding for restriction sites, may be designed to carry at their 5' ends, nucleotide sequences compatible with a recipient molecule such as that as described in (A) above. This allows for the outside ends of the assembled full-length target molecule to anneal to the single-stranded extensions on the linearized recipient molecule, thereby creating a transformable recombinant molecule in one experimental step.

Advantages of this approach over the restriction endonuclease-based cloning methodologies of the prior art include the following: (a) each single-stranded extension carries unique non-palindromic sequence whereby the amplified target fragments and linearized recipient molecule may be directionally assembled into desired recombinant molecule; (b) the covalent linkage by ligation may not be necessary, as the single-stranded extensions may be made long enough to produce a stable recombinant molecule; (c) the time-consuming procedures of restriction digestion, gel-purification and vector/insert ligation are omitted; and (d) multiple target molecule manipulations and cloning may be performed concurrently in a single experimental format.

The present application is further illustrated by Example XI and FIG. 37 showing the construction of 9° $N_m$ V93Q Polymerase mutant by directional assembly of the mutagenized intermediate fragments of polymerase gene into a linearized pNEB205A vector.

E) Chromosomal/Environmental DNA Cloning Outside the Boundaries of Known Sequence FIG. 17 shows a schematic illustration of a strategy for cloning DNA regions outside the boundaries of known sequences. The method is based on generating single-stranded extensions on the amplified fragments of unknown nucleotide sequence that are complementary to the single-stranded extensions on the recipient molecule. In a first step, a library of single-stranded flanking sequences are generated by linear amplification with one primer in the known region. To introduce a priming site at the unknown end of the amplified single-stranded flanking sequences, a homo-oligomer cytosine tail is then added at 3' termini using dCTP and terminal transferase. In the next step, the tailed single-stranded fragments are amplified using a pair of primers, which carry vector-compatible sequences at their 5' ends. One primer, which anneals to the unknown region of the target molecule, consists of a poly-guanine sequence and carries a modified nucleotide, for example 8-oxo-guanine, at the $6^{th}$ position from the 5' end. The other primer, which anneals to the known region of the target molecule, at 5' end is also supplemented by five guanines and an 8-oxo-guanine at the junction.

The library of the resulting double-stranded fragments are then treated with FPG glycosylase/AP lyase or with the nicking agent referred to as the USER™ Enzyme 2 (see Example II) where the enzyme or agent recognizes and nicks at 8-oxo-guanine leaving each fragment in the library flanked by the identical 3' single-stranded extensions comprised of six cytosines. A recipient molecule carrying single-stranded extensions comprised of six guanine residues is then used to assemble target fragments into recombinant molecules, thus generating a library of recombinant molecules. Construction and preparation of linear recipient molecules are described in Example I and FIG. 22. The library of recombinant molecules is then ready for transformation of competent *E. coli* cells.

The present application is further illustrated by Example XII showing the cloning of an unknown genomic segment to the 3' side of known sequence of the super-integron from *Pseudomonas alcaligenes* NEB#545 (New England Biolabs, Inc., Beverly, Mass.).

F) Construction of cDNA Libraries

FIG. 18 shows a schematic illustration depicting a strategy for construction of cDNA libraries from a total RNA sample. The first-strand synthesis generates a library of single-stranded cDNA products from total RNA using Reverse Transcriptase and oligo-dT primer containing a hexaguanine 5' tail with an 8-oxo-guanine at the 6$^{th}$ position from the 5' end (Primer 1 in FIG. 18). A homo-oligomer cytosine tail is then added at 3' termini of single-stranded cDNA products using dCTP and terminal transferase. Second-strand synthesis is then performed with DNA Polymerase I using a poly-dG primer having the 8-oxo-guanine at the 6$^{th}$ position from the 5' end (Primer 2 in FIG. 18).

In FIG. 18, both primers contain 5' terminal hexaguanine sequences with the 8-oxo-guanine as the modified nucleotide close to the 5' end. However, Primer 1 might consist of entirely poly-thymine sequence and carry deoxyuridine, close to the 5' end.

A library of the resulting double-stranded cDNA fragments can be treated with a suitable nicking agent which nicks at 8-oxo-guanine and optionally at deoxyuridine (U) leaving each fragment in the library flanked by 3' single-stranded extensions. Recipient molecules carrying the compatible single-stranded extensions may then be used to assemble target fragments into recombinant molecules. Examples of recipient molecules are provided in Example IC and Example ID. The library of recombinant cDNA clones can then be transformed into competent host cells.

The present invention is further illustrated by the following Examples. The Examples are provided to aid in the understanding of the invention and are not construed to be a limitation thereof.

The references cited above and below are herein incorporated by reference.

EXAMPLE I

Recipient Molecules with 3' Single-Stranded Extensions of Desired Length and Composition Linearized DNA vectors having unique 3' single-stranded extensions of desired length and composition were produced as shown below for vectors pNEB205A (SEQ ID NO:1), pNEB200A (SEQ ID NO:3), pNEB210A (SEQ ID NO:4) and pUC-TT (SEQ ID NO:6) (FIGS. 19-22) all of which were derived from the pNEB193 vector (New England Biolabs catalog 2002-2003, p. 318) by inserting a cassette into the multiple cloning site (FIG. 27A and FIG. 27B). The single-stranded extensions formed in each linearized vector molecule were designed to be non-complementary with each other to avoid problems arising from vector termini re-annealing to form transformable circular DNA and to provide a means to control the orientation of any target molecule inserted into the vector.

A) Generation of Linearized Vector pNEB205A.

A cassette 5'GCTGAGGGAAAGTCTAGATGTCTCCT-CAGC (SEQ ID NO:1) containing two inversely oriented nicking N.BbvCIB sites (CC↓TCAGC) and one XbaI restriction site (T↓CTAGA) was inserted into the multiple cloning site of pNEB193 plasmid. The new construct was designated as pNEB205A (FIGS. 19 and 27A and B).

pNEB205A plasmid was linearized to produce 8-nucleotide 3' single-stranded extensions (FIGS. 19 and 27C) as follows: 10 µg of pNEB205A plasmid DNA in 200 µl of NEBuffer #4 (20 mM Tris-acetate, pH 7.9, 10 mM magnesium acetate, 50 mM potassium acetate, 1 mM dithiothreitol and 100 µg/ml bovine serum albumin) was digested with 100 units of XbaI for 18 hours at 37° C. 20 units of N.BbvCIB were added to the reaction containing XbaI-cleaved DNA and incubated for an additional 1 hour at 37° C. Vector pNEB205A DNA was purified by phenol-chloroform extraction, followed by alcohol precipitation and was re-suspended in 100 µl of TE buffer (10 mM Tris-HCl, pH 8.0, 0.1 mM EDTA).

B) Generation of Linearized Vector pNEB200A.

Cassette 5'ACGAGACTCTAGAGGATCCGTCTA-GAGTCTGGT (SEQ ID NO:3) containing two XbaI restriction sites (T↓CTAGA) and two inversely oriented nicking N.BstNBI sites (5'-GAGCTNNNN↓, was inserted into the multiple cloning site of pNEB193 plasmid. The new construct was designated as pNEB200A (FIG. 20).

pNEB200A plasmid was linearized to produce 8-nucleotide 3' single-stranded extensions (FIG. 20) as follows: 8 µg of pNEB200A plasmid DNA in 200 µl of nicking buffer (10 mM Tris-HCl, pH 7.5, 10 mM MgCl$_2$, 150 mM KCl, 1 mM dithiothreitol) was digested with 100 units of N.BstNBI for 1 hour at 55° C. 100 units of XbaI were added to the reaction containing N.BstNBI-nicked DNA and incubated for an additional 1 hour at 37° C. Linearized vector pNEB200A DNA was purified by phenol-chloroform extraction, followed by alcohol precipitation and was re-suspended in 50 µl of TE buffer (10 mM Tris-HCl, pH 8.0, 0.1 mM EDTA).

C) Generation of Linearized Vector pNEB210A.

Cassette 5'GCTGAGGGGGGGATCCTTTTCATTCTA-GATGT CTCCTCAGC (SEQ ID NO:4) containing two inversely oriented nicking N.BbvCIB sites (CC↓TCAGC), one BamHI restriction site (G↓GATCC) and one XbaI restriction site (T↓CTAGA) was inserted into the multiple cloning site of pNEB193 plasmid. The new construct was designated as pNEB210A (FIG. 21).

pNEB210A plasmid was linearized to produce 6-nucleotide 3' single-stranded extension on one end and 8-nucleotide 3' single-stranded extension on other end of the linearized plasmid (FIG. 21) as follows: 10 µg of pNEB210A plasmid DNA in 200 µl of NEBuffer #4 (20 mM Tris-acetate, pH 7.9, 10 mM magnesium acetate, 50 mM potassium acetate, 1 mM dithiothreitol and 100 µg/ml bovine serum albumin) was doubly digested with 100 units of XbaI and 10 units of BamHI for 2 hours at 37° C. 20 units of N.BbvCIB were added to the reaction containing linearized DNA and incubated for an additional 1 hour at 37° C. Vector pNEB210A DNA was purified by phenol-chloroform extraction, followed by alcohol precipitation and was re-suspended in 100 µl of TE buffer (10 mM Tris-HCl, pH 8.0, 0.1 mM EDTA).

D) Generation of Linearized Vector pUC-TT.

Cassette 5' GCTGAGGGGGGGATCCTTTTCATG-GATCCCCC CCTCAGC (SEQ ID NO:6) containing two inversely-oriented nicking N.BbvCIB sites (CC↓TCAGC) and two BamHI sites (G↓GATCC) was inserted into the multiple cloning site of pNEB193 plasmid. The new construct was designated as pUC-TT (FIG. 22).

pUC-TT vector was linearized to produce 6-nucleotide 3' single-stranded extensions (FIG. 22) as follows: 10 µg of pUC-TT plasmid DNA in 200 µl of NEBuffer #4 (20 mM Tris-acetate, pH 7.9, 10 mM magnesium acetate, 50 mM potassium acetate, 1 mM dithiothreitol and 100 µg/ml bovine serum albumin) was digested with 10 units of BamHI for 2 hours at 37° C. 20 units of N.BbvCIB were added to the reaction containing linearized DNA and incubated further for 1 hour at 37° C. Vector pNEB210A DNA was purified by phenol-chloroform extraction, followed by alcohol precipitation and was re-suspended in 100 µl of TE buffer (10 mM Tris-HCl, pH 8.0, 0.1 mM EDTA).

EXAMPLE II

Preparation of Artificial Nicking Agents Specific for Deoxyuridine (U)

This Example describes the preparation of two artificial nicking agents, USER™ Enzyme and USER™ Enzyme 2 each capable of nicking a double-stranded DNA molecule at a deoxyuridine, generating a nucleotide gap and leaving 5' phosphate and 3' phosphate at the nick location. Each artificial nicking agent consists of two components. The USER™ enzyme contains UDG DNA glycosylase and EndoVIII DNA glycosylase/lyase while the USER™ Enzyme 2 contains UDG DNA glycosylase and FPG DNA glycosylase/lyase. One activity unit of the artificial nicking agent was defined as having in the mixture, sufficient amounts of the individual components required to cleave to completion, 10 pmol of a 34-mer oligonucleotide duplex containing a single deoxyuridine paired with a deoxyadenine in 10 µl of reaction buffer for 15 minutes at 37° C. Consequently, the optimal ratio of components in the mixture for producing an artificial nicking agent was determined according to the unit definition.

Based on the activity unit definition of UDG glycosylase (one unit of UDG glycosylase activity was defined as the amount of enzyme that catalyses the release of 60 pmol of uracil per minute from double-stranded, deoxyuracil containing DNA (New England Biolabs Catalog 2002-2003, p. 112)), the amount of UDG required to prepare 1 unit of artificial nicking agent was theoretically calculated to be 0.011 unit. However, the amount of this component in the artificial nicking agent can vary, depending on the desirability of increasing the rate of release of uracil bases relative to the rate of nicking at abasic sites. Accordingly, the amount of UDG component in one activity unit of nicking agent can be increased at least 2-fold to 100-fold higher than the theoretically requisite amounts, to a concentration of, for example 0.022 to 1.0 unit of UDG.

The optimal amount of a second component, either EndoVIII or FPG, required to prepare 1 unit of the respective artificial nicking agent, USER™ Enzyme and USER™ Enzyme 2, was determined as follows:

Preparation of substrate: the double-stranded oligonucleotide substrate containing a single deoxyuridine (FIG. 23 (SEQ ID NO:8)) was prepared as follows: 5 µM of the 3' and 5' flourescein-labeled 34-mer oligonucleotide containing a single deoxyuridine (U) at the 16$^{th}$ position was mixed with 5 µM of unlabeled complementary oligonucleotide containing deoxyadenine at the position opposite the deoxyuridine (U) in a 1 ml of total volume and incubated for 10 minutes at 100° C. The mixture was gradually cooled down to room temperature to yield the double-stranded oligonucleotide.

USER™ Enzyme: Various amounts of EndoVIII protein (from 3.9 to 250 ng) were pre-mixed with 0.2 units of UDG and the resulting mixtures were assayed for complete nicking of 10 pmol substrate in 15 min at 37° C. in 10 µl reaction buffer (50 mM Tris-HCl pH 7.5, 10 mM MgCl$_2$, 10 mM DTT, 1 mM ATP, 20 µg/ml BSA). The reactions were quenched by the addition of equal volume of 95% formamide, 0.1% xylene cyanol, 0.1% bromphenol blue, 10 mM EDTA, pH 11 and the products were analyzed on a 15% TBE-Urea denaturing gel (Invitrogen, Carlsbad, Calif.). In FIG. 24, the results of the activity assay showed that complete digestion of substrate occurred with at least 31.25 ng of EndoVIII in the presence of 0.2 units of UDG. Accordingly to the results of this example, 1 unit of USER™ Enzyme, can be prepared by mixing at least 31.25 ng of EndoVIII protein with 0.2 unit of UDG.

USER™ Enzyme 2: Various amounts of FPG protein (from 18.13 to 4300 ng) were pre-mixed with 0.1 unit of UDG and the resulting mixtures were assayed for complete nicking of 10 pmol substrate for 15 min at 37° C. in 10 µl reaction buffer (50 mM Tris-HCl pH 7.5, 10 mM MgCl$_2$, 10 mM DTT, 1 mM ATP, 20 µg/ml BSA). The reactions were quenched by the addition of equal volume of 95% formamide, 0.1% xylene cyanol, 0.1% bromphenol blue, 10 mM EDTA, pH 11 and the products were analyzed on a 15% TBE-Urea denaturing gel (Invitrogen, Carlsbad, Calif.). In FIG. 25, the results of an activity assay showed that complete digestion of substrate occurred with at least 145 ng of FPG in the presence of 0.1 unit of UDG. Accordingly to the results of this example, 1 unit of USER™ Enzyme 2, can be prepared by mixing at least 145 ng of FPG and 0.1 unit of UDG.

EXAMPLE III

Protocol and Kit for Cloning Target Molecule into pNEB205A Vector

This Example describes cloning of target molecules after DNA amplification using primers containing deoxyuridine (FIGS. 26A and 26B). The amplified products are treated with the nicking agent, USER™ Enzyme (see Example II), to create unique 3' single-stranded extensions, which can then anneal to the linearized vector pNEB205A carrying complementary 3' single-stranded extensions (see Example I Section A). The method is not dependent on restriction endonuclease cleavage, nor does it require DNA ligase for insertion of target product into vector.

A kit is provided here for use with a target molecule which has been amplified using Taq DNA Polymerase and uracil-containing primers as specified in FIGS. 26A and 26B.

The kit provides a cloning vector pNEB205A that has already been linearized and contains single-stranded extensions as described in Example I, Section A and a nicking agent, USER™ Enzyme, sufficient for 10 PCR cloning reactions. The kit further provides sequencing primers sufficient for 50 sequencing reactions and an instruction manual (New England Biolabs, Inc., Beverly, Mass.).

List of Components in the Kit:
  Linearized Vector pNEB205A, 10 µl (0.1 µg/µl)
  USER™ Enzyme, 10 µl (1 unit/µl),
  Sequencing primers:

```
M13/pUC Sequencing Primer (-47)
(5'-CGCCAGGGTTTTCCCAGTCACGAC-3'    (SEQ ID NO: 31)),
50 µl (3.2 pmol/µl), M13/pUC Reverse Sequencing Primer (-48)
(5'-AGCGGATAACAATTTCACACAGGA-3'    (SEQ ID NO: 32)),
50 µl (3.2 pmol/µl),
Instruction manual (New England Biolabs, Inc.,
Beverly, MA)
```

The instruction manual describes how to clone the target molecule using the reagents provided and others that are specified. For example, the manual may contain the following advice:

(a) Amplification

Amplification of the target molecule may be achieved using Taq DNA Polymerase and a primer pair where each primer has a sequence that is complementary to the target molecule and additionally has a 5' terminal sequence which is compatible with the single-stranded extension on the linearized vector (FIG. 26A). The orientation of the target molecule within the vector can be reversed by exchanging the vector-specific 5' terminal sequences in between the primers.

If the target molecule is a part of a circular plasmid which carries the ampicillin resistance gene, it is advisable to linearize the plasmid to avoid contamination of the PCR product with the transformable form of the original plasmid. Preferably, the plasmid may be digested with a restriction endonuclease that produces blunt-ended termini and/or contains several sites in the plasmid backbone but not within the target molecule to be amplified.

(b) Nicking of the Amplified DNA and Assembly Reaction

The nicking agent (USER™ Enzyme) was found to be active in all PCR buffers tested and in a variety of other commonly used buffers (Table I). The amplification product (PCR fragment) produced as discussed in (a) contains two uracil residues per molecule (FIG. 26B (b)). One activity unit of USER™ Enzyme (see Example II) is capable of nicking 5 pmol of the amplified DNA. If converted to mass concentration, 5 pmol of DNA is equal to 0.33 µg for a DNA 100 bp in length or 3.29 µg for a DNA 1000 bp in length.

It is preferable to insert no less than 0.011 pmol of the USER™ Enzyme-treated PCR fragment into 20 ng (0.011 pmol) of the linearized vector pNEB205A to saturate the vector. A portion of the PCR amplified fragments may not be compatible with the extensions on the vector molecule because Taq DNA Polymerase may add extra bases at the 3' end(s) of the fragments. To account for these maximum non-templated additions, insertion efficiency can be achieved using a PCR fragment concentration of at least 3-fold higher than the vector concentration. For example, ≧0.033 pmol of PCR product may be used for each 0.011 pmol (20 ng) of vector.

Consequently, an assembly mixture may contain 10 µl PCR sample, 1 µl linearized pNEB205A (20 ng) and 1 µl USER™ Enzyme (1 unit), which is incubated for 15 minutes at 37° C. to nick the PCR products at the uracils. Complementary extensions can then be annealed to form recombinant molecules by incubating for 15 minutes at room temperature (FIG. 26B step (e)).

T4 DNA Ligase may be added to the assembly reaction to obtain covalently-linked recombinant molecules. This is desirable if the assembled recombinants are to be used for electroporation or otherwise further manipulated. If required, 1 µl of 10×T4 DNA Ligase buffer and 1 µl of T4 DNA ligase may be added to the assembly reaction after 15 minute incubation at 37° C. and incubated for an additional 15 minutes at room temperature.

(c) Completion of the Cloning Method

The resulting annealed recombinant molecules formed in a 2-12 µl of the assembly reaction from (b) can be used to transform chemically competent E. coli cells. Transformed cells can then be plated on either LB plates containing 100 µg/ml ampicilin or on the LB plates containing 100 µg/ml ampicilin, 0.1 mM IPTG and 0.01 mg/ml X-gal plates for the use of blue-white selection. Using blue-white selection, transformants carrying the recombinant molecules form white colonies, while transformants carrying the unmodified vector form blue colonies.

The sequence of the inserted target molecule can be verified by sequencing using sequencing primers listed in the kit components above.

(d) Subcloning

If desired, the target molecule can be subcloned into another expression vector using a variety of unique restriction sites located within the MCS of pNEB205A (FIGS. 27B and 27C). The MCS carries four unique 8-base restriction sites (for AscI, PacI, PmeI and SbfI) flanking the insertion site.

When a particular restriction site desired is not present in the multiple cloning site of pNEB205A, for example, such site can be readily engineered into the target molecule by designing the PCR primers to contain an insertion corresponding to the restriction site between the deoxyuridine (U) and the priming sequence, as shown below:

```
Left primer: 5'-[GGAGACAU + (restriction site) +
priming sequence]

Right primer: 5'-[GGGAAAGU + (restriction site) +
priming sequence].
```

To subclone the target molecule directly into the ATG codon of another expression vector, an NdeI site can be used which is automatically created within the left primer if the ATG codon is placed downstream of the uracil residue (5'GGAGACAUATG . . . ) (SEQ ID NO:9).

TABLE 1

USER ™ Enzyme activity in various PCR buffers and other commonly used buffers

| Reaction Buffer | Buffer Composition | USER ™ activity (%) |
|---|---|---|
| T4 DNA Ligase (NEB) | 50 mM Tris-HCl pH 7.5, 10 mM MgCl₂, 10 mM DTT, 1 mM ATP, 20 µg/ml BSA | (100) |
| Thermopol Buffer (NEB) | 20 mM Tris-HCl pH 8.8, 10 mM KCl, 10 mM (NH₄)₂SO₄, 0.1% Triton X-100 | 100 |
| Thermopol II (NEB) + 4 mM MgSO₄ | 20 mM Tris-HCl pH 8.8, 10 mM KCl, 10 mM (NH₄)₂SO₄, 0.1% Triton X-100, 4 mM MgSO₄ | 100 |
| GeneAmp Buffer (Applied Biosystems) | 10 mM Tris-HCl pH 8.3, 50 mM KCl, 1.5 mM MgCl₂, 0.001% (w/v) gelatin | 200 |
| GeneAmp Buffer II (Applied Biosystems) + 4 mM MgCl₂ | 10 mM Tris-HCl pH 8.3, 50 mM KCl, 4 mM MgCl₂ | 100 |
| PCR buffer (Roche) | 10 mM Tris-HCl pH 8.3, 50 mM KCl, 1.5 mM MgCl₂ | 100 |
| Taq Pol Buffer (Promega) | 10 mM Tris-HCl pH 9.0, 50 mM KCl, 0.1% Triton-X-100, 2.5 mM MgCl₂, | 75 |
| PCR Buffer (Qiagen) | pH 8.7, 1.5 mM MgCl₂, Additional components unknown | 100 |
| TE Buffer | 10 mM Tris-HCl pH 8.0, 0.1 mM EDTA, | 100 |
| TE Buffer + 2 mM MgSO₄ | 10 mM Tris-HCl pH 8.0, 0.1 mM EDTA, 2 mM MgSO₄ | 100 |
| TE Buffer + 4 mM MgSO₄ | 10 mM Tris-HCl pH 8.0, 0.1 mM EDTA, 4 mM MgSO₄ | 100 |
| TE Buffer + 6 mM MgSO₄ | 10 mM Tris-HCl pH 8.0, 0.1 mM EDTA, 6 mM MgSO₄ | 75 |

(NEB—New England Biolabs, Inc., Beverly, MA)
(Applied Biosystems, Foster City, CA)
(Roche Diagnostics GmbH, Mannheim, Germany)
(Qiagen, Studio City, CA)

EXAMPLE IV

Cloning of the Chloramphenicol Resistance Gene (Cat) into Vector pNEB205

Using the methodology described in Example III, the cat (Cm$^r$) gene was amplified as a 950 bp fragment of the pGPS2.1 plasmid with Taq DNA Polymerase and primers listed below:

```
Left primer:
                                    (SEQ ID NO: 33)
5'-GGAGACAUCGGATCCATACCTGTGACGGAAG Right primer:
                                    (SEQ ID NO: 34)
5'-GGGAAAGUGGATCCAGGCGTTTAAGGGCACC
```

The 50 µl PCR reactions contained 5 µl of 10× GenAmp PCR buffer (Applied Biosystems, Foster City, Calif.), 20 ng of the pGPS2.1 (New England Biolabs, Inc., Beverly, Mass.) DNA, 200 µM dNTPs, 0.2 µM of each primer and 2 units of Taq DNA Polymerase. The cat gene was amplified for 8, 9, 10, 11, 13, 16, 20, 25 and 30 cycles using the cycling protocol below:

| | | |
|---|---|---|
| 94° C. | 5 min | |
| 94° C. | 30 sec | |
| 55° C. | 1 min | one cycle |
| 72° C. | 40 sec | |
| 72° C. | 5 min | |

The amount of PCR product in a 10 µl sample (20% of the total PCR volume) was evaluated by gel electrophoresis (FIG. 28) and was estimated to be 5, 10, 17, 45, 82, 164, 215, 346 or 390 ng, respectively.

10 µl of each PCR sample was mixed with 1 µl (20 ng) of linearized vector pNEB205 and 1 µl (1 unit) of USER™ Enzyme. Reactions were incubated for 15 minutes at 37° C. to cleave at deoxyuracil residues and an additional 15 minutes at room temperature to allow annealing of the complementary extensions.

50 µl of chemically competent *E. coli* ER2267 cells (cell competency $2 \times 10^7$ c.f.u./µg pNEB205A) were transformed with 3 µl of the assembly reaction. Transformants were selected by plating 3×25 µl of the transformation reaction (from 1.5 ml total transformation reaction volume) on LB plates supplemented with Amp+IPTG+X-gal. The white (recombinant) and blue (vector background) colonies were counted after 18 hours at 37° C. Cloning efficiency was determined by calculating the fraction of white colonies compared to the total number of transformants. The cat gene cloning into pNEB205A results are shown in FIG. 29 and FIG. 30.

EXAMPLE V

Protocols and Kit for Target Molecule Manipulation

This Example describes how various DNA manipulations may be performed such as site-specific mutagenesis, generation of target molecule fusions, deletion, insertion or replacement of any DNA segment virtually at any position of the target molecule, assembly of target molecules from multiple DNA fragments and any combination of the above applications simultaneously (FIGS. 8-15) using deoxyuridine as the modified nucleotide (X).

Target molecule(s) are amplified by generating multiple overlapping fragments. To create the overlap region between two neighboring fragments of the target molecule, the amplification primers are designed to have an overlapping sequence at their 5' ends with one deoxyuridine flanking the overlap sequence on the 3' side (FIG. 31).

The primer design shown in FIG. 31 can be further modified to incorporate sequence changes at or near the overlap region to produce the specific desired DNA manipulation (FIGS. 9-15). After amplification, the sequence changes become incorporated into the amplified PCR fragments. The adjoining fragments are flanked by a common overlap region, but one fragment contains a deoxyuridine (U) on the top strand of the overlap region, while the other fragment contains a deoxyuridine (U) on the bottom strand of the overlap region. Single-stranded extensions can then be created at the junction of neighboring fragments by excising deoxyuridine (U) residues with the USER™ Enzyme. The single-stranded extensions, generated from fragments designed to adjoin, are complementary to each other, as they consist of the overlap sequence. The fragments can be directionally assembled to yield a full-length target molecule with sequence changes.

The particulars of this Example are abstract protocols to explain how any DNA can be modified in a predetermined manner (FIGS. 32-37) using a kit containing reagents and the appropriate protocol of the type provided by (a)-(d) below.

(a) Design of Primers

A target molecule can be manipulated by using multiple primer pairs as shown in FIG. 31. Overlapping Primers P1 and P2 may overlap each other by 2-20 nucleotides on their 5' ends while priming opposite DNA strands on the target molecule. The priming site can be selected on the target molecule sequence at or near the point of manipulation. In both of the overlapping primers, the 3'-nucleotide flanking the overlap sequence can be deoxyuridine (U). Preferably, the nucleotide sequence within the overlap does not contain a two-fold axis of symmetry, thus avoiding self-complementarity. Where the sequence of target DNA at the point of manipulation does not display a suitable priming sequence for the overlap, a sequence change can be introduced to provide a necessary A or T, for example, at the degenerate third position of a codon.

The sequences of Primers P3 and P4 may complement sequences on the target molecule containing unique restriction sites, which can then be used for subsequent cloning of the assembled target molecule. Alternatively, a unique restriction site might be introduced into the 5' end of the P3 and P4 primer sequence.

(b) Amplification

A target molecule can be amplified with Taq DNA Polymerase as two overlapping fragments in separate PCR reactions using (P1+P3) and (P2+P4) primer pairs. The result of amplification is two fragments in which one terminus in each occurs at the position of interest (the "split site"). At the split site, each PCR fragment is flanked by an identical copy of the overlap, except that uracils are positioned on opposite DNA strands (FIG. 8). The PCR fragments should preferably be purified and adjusted to a concentration of 0.1-1.0 µM.

Because Taq DNA Polymerase introduces non-template nucleotides at the 3' termini of amplified PCR fragments, end polishing of PCR fragments is suggested for achieving accurate and efficient DNA manipulation. End polishing can be achieved as follows:

For a 50 µl reaction, no more than 10 pmol of PCR Fragment is mixed with 5 µl 10×T4 DNA ligase buffer, 1 µl 10 mM dNTP, 1 µl DNA Polymerase I Large (Klenow) Fragment. $H_2O$ is added to a final volume of 50 µl. The mixture is incubated for 10 minutes at 37° C. to remove non-template 3' nucleotides followed by a further incubation for 20 minutes at 80° C. to inactivate the Klenow Fragment.

(c) Generation of 3' Single-Stranded Extensions Using a Nicking Agent

3' single-stranded extensions can be generated on the polished PCR fragments with the USER™ Enzyme by nicking the PCR fragments on the 3' and 5' sides of the deoxyuridine (U) and dissociation of the short oligonucleotide created by the nick to form fragments flanked by a 5' phosphate on one strand and a 3' single-stranded extension on the other strand. The nicking is achieved by supplementing the 50 µl reaction from (b) with 1 unit (1 µl) of the USER™ Enzyme (see Example II) and incubating for 15 minutes at 37° C.

If the PCR fragment contains two uracils per molecule, one activity unit of the USER™ Enzyme is capable of nicking no more than 5 pmol of PCR product under the reaction conditions defined above.

(d) Assembly Reaction

The preparations of individual PCR fragments containing complementary single-stranded extensions described in (c) can then be combined in equimolar amounts. 1 µl T4 DNA Ligase is added to the mixture of PCR fragments and the mixture is incubated for 30 minutes at room temperature to ligate the PCR fragments. ½₀ volume of the ligation reaction is then retrieved and run on an agarose gel to check for ligation efficiency. If the ligation yield is found to be satisfactory, T4 DNA Ligase is inactivated by heating for 20 minutes at 80° C.

Use of equimolar amount of PCR fragments provides a maximum yield of ligated fragments and is especially important when ligating more than two PCR fragments, otherwise the under-represented fragment will limit the final product formation. However, in some cases, due to the variations in the nucleotide composition and/or length of single-stranded extensions and PCR fragment sizes, the concentration ratio that produces the highest yield of the final ligation product may be optimized in a pilot ligation prior to a large-scale ligation reaction.

(e) Cloning of Ligated Product into the Vector of Choice

The ligated product can be digested with appropriate restriction endonucleases that recognize sequences engineered into the outside Primers P3 and P4 and cloned using traditional protocols which include gel-purification and ligation of the target fragment into the vector of choice that has been pre-cleaved with the same or a compatible restriction endonuclease. Alternatively, the ligated product can be introduced into a vector according to Examples III and IV.

In the present Example, a kit is provided which contains reagents and protocols appropriate for use with the PCR amplified DNA fragments which have been manipulated as specified in FIGS. 8-15. The kit described below contains sufficient reagents for 10 reactions.

List of Components in the Kit:
- 10×T4 DNA Ligase Buffer, 500 µl;
- 10 mM dNTP solution, 100 µl;
- DNA Polymerase I, Large (Klenow) Fragment, 20 µl (5 units/µl);
- USER™ Enzyme, 10 µl (1 unit/µl)
- T4 DNA Ligase, 20 µl (400 units/µl)
- Instruction manual For convenience, all enzymes in the kit have been adjusted to perform in the T4 DNA Ligase buffer to avoid buffer changes during the reaction.

EXAMPLE VI

Site-Specific Mutagenesis of HincII Restriction Endonuclease

The design of two primer pairs P1/P4 and P2/P3 and their use in modifying hincIIR endonuclease gene is shown in FIG. 32. Primer P1 coded for a substitution of codon CAA with the codon TTT. 420 bp and 380 bp fragments of the hincIIR gene were amplified using Taq DNA Polymerase and primer pairs P1/P4 and P2/P3, respectively. The total volume for each PCR reaction was 6 tubes of 100 µl. After amplification, the PCR products of six identical reactions were combined, purified by phenol-chloroform extraction and alcohol precipitation and dissolved in 50 µl of TE buffer. DNA concentration was determined by gel electrophoresis and was estimated to be 0.2 mg/ml for each PCR fragment. Two 50 µl reactions were set up as follows:
- 25 µl (~20 pmoles) of either 380 bp or 420 bp PCR fragment
- 5 µl of 10×T4 DNA Ligase buffer
- 1 µl of 10 mM dNTPs
- 18 µl of Milli-Q™ H₂O
- 1 µl (5 units) of Klenow Fragment The reactions were incubated for 10 minutes at 37° C. to form blunt-ended PCR fragments. Klenow Fragment was inactivated by incubating for 20 minutes at 80° C. 1 µl (1 unit) of USER™ Enzyme was added to each reaction and samples were incubated for 15 minutes at 37° C. After incubation, the reactions were placed on ice.

Pilot ligation: 1 µl of each PCR fragment was combined with 7 µl of 1× T4 DNA Ligase buffer. 1 µl (40 units) of T4 DNA Ligase was added and incubated for 30 minutes at room temperature. The ligation reaction was analyzed by gel electrophoresis in parallel with 1 µl of each USER™-treated fragment to evaluate the ligation efficiency (FIG. 32 (e)).

Large-scale ligation: 20 µl of each PCR fragment were combined, 1 µl (400 units) of T4 DNA Ligase was added and incubated for 30 minutes at room temperature. A 2 µl aliquot was assayed by gel eletrophoresis to evaluate ligation efficiency. T4 DNA Ligase was inactivated by incubating for 20 minutes at 80° C. The ligation mixture was digested with NdeI and SapI restriction endonucleases. A 780 bp NdeI-SapI fragment carrying the complete hincIIR/Q138F gene was purified from the agarose gel and cloned into NdeI-SapI cleaved dephosphorylated pTXB1 vector (New England Biolabs, Inc., Beverly, Mass.).

EXAMPLE VII

Insertion of Unique Restriction Sites and Deletion of 18 bp Segment from pUC19 Vector DNA The design of two primer pairs P1/P4 and P2/P3 and their use in inserting restriction sites and deleting a sequence from pUC19 is illustrated in FIG. 33. The priming sites for the Primers P1 and P2 on pUC19 were separated by the 18 base pair sequence that was to be deleted. To create the 6 bp-long overlap region, Primers P1 and P2 were supplemented by six-nucleotide insertion sequences at their 5' ends, which also created BsrGI and AvrII restriction sites. Two fragments of pUC19 were amplified (one of 610 bp and one of 810 bp) with Taq DNA Polymerase and primer pairs P1/P4 and P2/P3, respectively. Six identical 100 µl PCR reactions were carried out. After amplification, the PCR products combined (each fragment separately), were purified by phenol-chloroform extraction and alcohol precipitation and dissolved in 50 µl of TE buffer. The 610 bp PCR fragment concentration was 0.15 mg/ml (0.38 pmol/µl); the 810 bp fragment concentration was 0.3 mg/ml (0.57 pmol/µl). An end-polishing reaction (100 µl) was set up as follows:
- 62 µl of Milli-Q™ H₂O
- 15 µl (5.7 pmoles) of 610 bp fragment
- 10 µl (5.7 pmoles) of 810 bp fragment
- 10 µl of 10×T4 DNA Ligase buffer
- 2.0 µl of 10 mM dNTPs
- 1.0 µl (5 units) of Klenow Fragment The reaction mixture was incubated for 10 minutes at 37° C. to polish ends of the PCR fragments. Klenow Fragment was then inactivated by incubating for 20 minutes at 80° C. 1 µl of the USER™ Enzyme was then added to the reaction mixture and incubated for 15 minutes at 37° C. 1 µl of T4 DNA Ligase was then added and incubated for 30 minutes at room temperature. T4 DNA Ligase was inactivated by incubating for 20 minutes at 80° C. A 10 µl aliquot from the ligation mixture was digested either with BsrGI or AvrII and assayed by gel electrophoresis to check for the presence of these newly-introduced restriction sites within the 1420 bp ligation product (see FIG. 35B). The 1420 bp ligation product, now carrying unique BsrGI and AvrII sites, was cleaved with BsaI and HindIII; the 1380 bp DNA fragment was purified from the agarose gel and subcloned into BsaI and HindIII-cleaved dephosphorylated pUC19.

EXAMPLE VIII

Construction of *E. coli* Endonuclease VIII

Mxe Intein Gene Fusion

The design of two primer pairs P1/P4 and P2/P3 and their use in constructing an endonuclease gene is shown in FIG. 34. Seven-nucleotide long overlap sequences for P1 and P2 primers consisted of the last two nucleotides of the EndoVIII gene and the first five nucleotides of the Mxe Intein gene. An 800 bp EndoVIII gene was amplified from *E. coli* genomic DNA using Taq DNA Polymerase and primer pair P2/P3. A 265 bp 5' terminal fragment of the Mxe Intein gene was amplified from pTXB1 using Taq DNA Polymerase and primer pair P1/P4. The total amplification reaction volume for each PCR was 6 tubes of 100 µl.

After amplification, the PCR products were purified using QIAquick™ PCR Purification Kit (Qiagen, Studio City, Calif.). PCR fragment concentration was calculated from gel electrophoresis to be 0.1 mg/ml (0.2 pmol/µl) for the 800 bp PCR fragment; and 0.05 mg/ml (0.3 pmol/µl) for the 265 bp PCR fragment. The 40 µl reaction was set up as follows:

4 µl of Milli-Q™ $H_2O$
10 µl (2 pmoles) of 800 bp fragment
20 µl (6 pmoles) of 265 bp fragment
4 µl of 10×T4 DNA Ligase buffer
1.0 µl of 10 mM dNTPs
1 µl (5 units) of Klenow Fragment The PCR fragment concentration ratio 1:3 was chosen to avoid contamination of the 1065 bp ligation product with the initial 800 bp PCR fragment. The reaction mixture was incubated for 10 minutes at 37° C. to polish the ends of PCR fragments. Klenow Fragment was inactivated by incubating for 20 minutes at 80° C. 1 µl of the USER™ Enzyme was added to the reaction mixture and incubated for 15 minutes at 37° C. 1 µl of T4 DNA Ligase was added and ligation proceeded for 30 minutes at room temperature. A 2 µl aliquot of the ligation mixture was assayed by gel electrophoresis (see FIG. 36B). T4 DNA Ligase was inactivated by incubating for 20 minutes at 80° C.

The 1065 bp ligation product comprised of the EndoVIII gene fused to the 5'-terminus of the Mxe Intein gene, was cleaved with NdeI and AatII, gel-purified and subcloned into NdeI- and AatII-cleaved dephosphorylated pTXB1 vector.

EXAMPLE IX

Construction of the HincIIR/Q138A Mutant and its Concurrent Insertion into pTXB1 Vector Between the Promoter Region and Mxe Intein Gene The experimental scheme for construction of a mutant gene and insertion of the mutant gene into a vector is shown in FIG. 35. FIG. 35 (*a*) shows a schematic illustration of the desired product, which was the product of the present Example. Four PCR primer pairs P1/P2, P3/P4, P5/P6 and P7/P8 were designed as depicted in FIG. 35 (*b*) including three sets of the overlapping primers, P2/P3, P4/P5, P6/P7 respectively.

The overlapping Primers P2 and P3 created the fusion between the promoter region of pTXB1 vector and the 5' terminus of the hincIIR gene. An 11-nucleotide long overlap sequence included four nucleotides of pTXB1 sequence and the first seven 5' terminal nucleotides of the hincIIR gene.

The overlapping Primers P4 and P5 introduced the codon substitution at the position 138 of the hincIIR gene. In Primer P5, wild type codon CAA (coding for a glutamine) was replaced by a mutagenic codon GCT, which coded for an alanine. In Primer P4, correspondingly, the sequence TTG was replaced by the sequence AGC.

The last set of the overlapping primers, P6 and P7, created a fusion between the 3' terminus of the hincIIR gene and a 5' terminus of the Mxe Intein gene. A 9-nucleotide long overlap sequence included the last four 3' terminal nucleotides of the hincIIR gene and first five nucleotides of the Mxe Intein gene. Primers P1 and P8 both primed pTXB1 vector sequence across the unique XbaI and BsrGI sites.

Four separate PCR reactions were performed using Taq DNA Polymerase and the respective primer pair. A 140 bp promoter region of pTXB1 vector was amplified using primer pair P1/P2 (PCR1) and pTXB1 plasmid as a template. The 420 bp and 380 bp fragments of the hincIIR gene were amplified using a full-length hincIIR gene as a template and either the primer pair P3/P4 (PCR2) or primer pair P5/P6 (PCR3), respectively. A 360 bp 5'-terminal fragment of Mxe Intein gene was amplified from pTXB1 vector using primer pair P7/P8 (PCR4). After amplification, each PCR fragment was purified by phenol-chloroform extraction and alcohol precipitation and dissolved in 50 µl of Milli-Q™ $H_2O$. The PCR fragment concentration was calculated from the $OD_{260}$ measurements: PCR1: 0.23 mg/ml (2.9 pmol/µl); PCR2: 0.35 mg/ml (1.3 pmol/µl); PCR3: 0.30 mg/ml (1.2 pmol/µl) and PCR4: 0.30 mg/ml (1.3 pmol/µl).

Four 50 µl reactions were set up as follows:
5 µl of 10×T4 DNA Ligase buffer
1.0 µl of 10 mM dNTPs
1 µl (5 units) of Klenow Fragment
28 µl of Milli-Q™ $H_2O$
15 µl (44 pmoles) of PCR1
(or 15 µl (20 pmoles) of PCR2)
(or 15 µl (18 pmoles) of PCR3)
(or 15 µl (20 pmoles) of PCR4)

Each reaction mixture was incubated for 10 minutes at 37° C. to polish the ends of PCR fragments. Klenow Fragment was inactivated by incubating for 20 minutes at 80° C. Since 420 bp and 380 bp hincIIR fragments contain two uracils per molecule, 2 units of USER™ Enzyme are necessary to completely nick 20 pmol of each fragment. Therefore, 2 µl of the USER™ Enzyme was added to each reaction mixture and incubated for 15 minutes at 37° C. After incubation, the reactions were placed on ice.

Pilot ligation (FIG. 35 step (f)): 1 µl of each PCR fragment was combined in 5 µl of 1×T4 DNA Ligase buffer. 1 µl of T4 DNA Ligase was then added and PCR fragments were ligated for 30 minutes at room temperature. The ligation reaction was analyzed by gel-electrophoresis in parallel with 1 µl of each USER™-treated fragment to evaluate ligation efficiency.

Large-scale ligation: 20 µl of PCR1, PCR2 and PCR3 fragment and 40 µl of PCR4 fragment were combined together, 1 µl of T4 DNA Ligase was added and ligation proceeded for 30 minutes at room temperature. In the large-scale ligation, the concentration of PCR4 fragment was doubled as the pilot ligation showed the significant accumulation of the 900-bp partial ligation product. A 5 µl aliquot from the ligation mixture was assayed by gel electrophoresis. T4 DNA Ligase was inactivated by incubating for 20 minutes at 80° C. The 1270 bp ligation product carried the hincIIR/Q138A gene precisely inserted between the promoter region of pTXB1 and the 5' terminus of the Mxe Intein gene. It was then cleaved with XbaI and BsrGI restriction endonucleases, purified from the agarose gel and subcloned into XbaI and BsrGI cleaved, dephosphorylated pTXB1 vector.

EXAMPLE X

Assembly of hAP1 Gene from Human Genomic DNA in Combination with Silent Mutagenesis The experimental scheme for assembly of the hAP1 gene in combination with silent mutagenesis is shown in FIG. 36. FIG. 36 (a) shows a schematic illustration of the cDNA of the human AP1 endonuclease gene. Five PCR primer pairs P1/P2, P3/P4, P5/P6 P7/P8 and P9/P10 were designed as depicted in FIG. 36 (b) including four sets of the overlapping primers, P2/P3, P4/P5, P6/P7, P8/P9, respectively.

The overlapping Primers P2 and P3 created the junction between the Exon 2 and Exon 3 of hAP1 gene. An 8-nucleotide long overlap region was selected within the 5' terminal sequence of Exon 3. Primer P2 annealed to the 3' terminal region of Exon 2, but at the 5' end it was supplemented with a 20 nucleotide-long sequence that was the reverse complement of the 5' terminal sequence of Exon 3.

The overlapping Primers P4 and P5 created the junction between Exon 3 and Exon 4 of hAP1 gene. A 9-nucleotide overlap region was formed from the last four nucleotides of Exon 3 and five first nucleotides of Exon 5.

The overlapping Primers P6 and P7 created the junction between Exon 4 and Exon 5 of hAP1 gene. A 9-nucleotide overlap region was formed from the last four nucleotides of Exon 4 and the five first nucleotides of Exon 5.

The overlapping Primers P8 and P9 introduced a silent substitution within the Exon 5 sequence in order to eliminate the naturally occurring NdeI restriction site. Within the 9 nucleotide overlap region Primer P8 carried a T to C substitution and Primer P9 carried an A to G substitution such that the NdeI site CATATG was converted into CGTATC.

The NdeI restriction site was then engineered into the 5' sequence of the Primer P1 to create a restriction endonuclease site for subcloning of the assembled hAP1 gene. For the same purpose, a SapI site was engineered into the 5' sequence of the Primer 10.

Five separate PCR reactions were performed using Taq DNA Polymerase and total human genomic DNA as a template. An 80 bp Exon 2 was amplified using primer pair P1/P2 to yield a product referred to as PCR1. A 180 bp Exon 3 was amplified using primer pair P3/P4 yielding product referred to as PCR2. A 200 bp Exon 4 was amplified using primer pair P5/P6 yielding product referred to as PCR3. An 80 bp 5' terminal portion of Exon 5 was amplified using primer pair P7/P8 yielding product referred to as PCR4 and a 460 bp 3' terminal portion of Exon 5 was amplified using primer pair P9/P10 yielding product referred to as PCR5. After amplification, each PCR fragment was purified by phenol-chloroform extraction and alcohol precipitation and dissolved in 50 µl of Milli-Q™ H$_2$O. PCR fragment concentration was measured to be: PCR1: 0.005 mg/ml (0.10 pmol/µl); PCR2: 0.03 mg/ml (0.26 pmol/µl); PCR3: 0.10 mg/ml (0.77 pmol/µl); PCR4: 0.01 mg/ml (0.20 pmol/µl); PCR5: 0.05 mg/ml (0.17 pmol/µl).

Five 50 µl reactions were set up as follows:
5 µl 10×T4 DNA Ligase buffer
1.0 µl 10 mM dNTPs
1 µl Klenow Fragment
40 µl (4 pmol) of PCR1 or PCR2 or PCR3 or PCR4 or PCR5
Milli-Q™ H$_2$O up to 50 µl.

Each reaction mixture was incubated for 10 minutes at 37° C. to form blunt ended PCR fragments. Klenow Fragment was inactivated by incubating for 20 minutes at 80° C. 2 µl (2 units) of USER™ Enzyme was added to each reaction mixture and incubated for 15 minutes at 37° C. After incubation, the reactions were placed on ice.

Pilot ligation (FIG. 36 stein (f)): PCR fragments were combined in the following ratio (µl):
PCR1:PCR2:PCR3:PCR4:PCR5=4:1:1:1:3

1 µl of T4 DNA Ligase was added and ligation proceeded for 30 minutes at room temperature. The ligation reaction was analyzed by gel electrophoresis in parallel with 1 µl of each PCR fragment to evaluate ligation efficiency.

Large-scale ligation: 10-fold higher amounts of PCR fragments were combined together in the same ratio as shown in the pilot ligation, 1 µl of T4 DNA Ligase was added and ligation proceeded for 30 minutes at room temperature. 5 µl aliquot from the ligation mixture was assayed by gel electrophoresis. T4 DNA Ligase was inactivated by incubating for 20 minutes at 80° C.

The 1000 bp ligation product carried the assembled hAP1 gene with the inactivated NdeI restriction site at position 490 nt. The ligated fragment was then cleaved with NdeI and SapI, purified from the agarose gel and subcloned into NdeI and SapI cleaved dephosphorylated pTXB1 vector.

EXAMPLE XI

Site-Specific Mutagenesis of 9° N$_m$ Polymerase by Directional Assembly of the Mutagenized PCR Fragments into Linearized pNEB205A Vector A summary of the experimental approach used here to achieve site-specific mutagenesis is shown in FIG. 37. Two PCR primer pairs were designed as depicted in FIG. 37. Overlapping Primers P1 and P2 coded for the codon 93 change from GTC (coding for Val93) to CAA (coding for Gln93). Primer P1 carried two nucleotide changes: TC substitution with the AA. Primer 2 carried three nucleotide changes: GAC substitution with the TUG. Primers P3 and P4 at their 5' ends were supplemented with an additional 8-nucleotides that were compatible with the single-stranded extensions on linearized pNEB205A vector (see Example II). 2041 bp and 287 bp fragments of the 9° N$_m$ Polymerase gene were amplified using Taq DNA Polymerase and primer pairs P1/P4 and P2/P3, respectively. The total reaction volume for each PCR was 100 µl. The assembly reaction was set-up as follows:

1 µl (0.1 pmol) of 287 bp PCR fragment
10 µl (0.1 pmol) of 2041 bp PCR fragment
1 µl pNEB205A linear vector (20 ng)
1 µl USER™ Enzyme (1 unit)

The reaction was incubated for 15 minutes at 37° C., and then for 15 minutes at room temperature. 50 µl of E. coli ER2267 competent cells were transformed with 5 µl of the above reaction. 100 µl of the transformation reaction (out of total 1 ml volume) was plated on LB plates containing 100 µg/ml ampicilin.

More than 2×10$^3$ transformants were recovered after 18 hours incubation at 37° C. Out of these, plasmid DNA was purified from 6 individual transformants and assayed for the presence of insert by cleavage with restriction endonuclease BbvCI. All of them carried the 2.3 kb insert, indicating that full-length 9° N$_m$ Polymerase gene was cloned. Five of six plasmids were sequenced across the mutagenized region and found that all of them carry desired codon substitution: GTC to CAA.

EXAMPLE XII

Cloning of the 3' Genomic Region of the Super-Integron from *Pseudomonas alcaligenes* NEB#545

An outline of the strategy used to clone the unknown 3' region of the super integron from *Pseudomonas alcaligenes* NEB#545 (New England Biolabs, Inc., Beverly, Mass.) downstream of the 3' end of the contig C (Vaisvila et al. *Mol. Microbiol.* 42:587-601 (2001)) is shown in FIG. 38.

Three PCR primers were designed. Primer Pal3-1 (GGAACGGCAATTGGCCTTGCCGTGTA (SEQ ID NO:28) was used for linear amplification of the 3' genomic DNA segments.

Primer Pal3-3 (GGGGGXCTAAAGCCTGCCCCT-TAACCAAAC GTTA (SEQ ID NO:29), where X is 8-oxo-Guanine) and Primer GG-2 (GGGGGXGGGGGGGGGGGGHN (SEQ ID NO:30), where H is either A, T, or C; N is either A, T, C, or G; and X is 8-oxo-Guanine) were used for nested PCR amplification.

A library of single-stranded fragments downstream of the known 3' end of the contig C was generated from the total genomic DNA by linear amplification using the protocol below. 100 ng of *Pseudomonas alcaligenes* genomic DNA in a 100 µl of ThermoPol reaction buffer containing 10 pmol Pal3-1 primer, 200 µM dNTP and 2.5 units of Taq DNA Polymerase was linearly amplified for 25 cycles using the cycling protocol below:

| 94° C. | 4 min  |           |
|--------|--------|-----------|
| 94° C. | 30 sec |           |
| 57° C. | 1 min  | one cycle |
| 72° C. | 1 min  |           |

After amplification, the resulting amplification products were purified on Microcon-PCR Filter Unit (Millipore Corporation, Bedford, Mass.).

For the cytosine tailing reaction, 10 µl of the purified amplification products were incubated with 20 units of Terminal Transferase for 15 minutes at 37° C. in a NEBuffer 4 reaction buffer containing 0.25 mM $CoCl_2$ and 2 mM dCTP. Terminal Transferase was then inactivated by incubating at 75° C. for 10 minutes.

To create a library of the double-stranded products, 2 µl of the tailed amplification products were further amplified for 25 cycles with Pal3-3 and GG-2 primers in a 100 µl of ThermoPol reaction buffer containing 10 pmol of each primer, 200 µM dNTP and 2.5 units of Taq DNA Polymerase using the cycling protocol below:

| 94° C. | 4 min  |           |
|--------|--------|-----------|
| 94° C. | 30 sec |           |
| 57° C. | 1 min  | one cycle |
| 72° C. | 1 min  |           |
| 72° C. | 5 min  |           |

To introduce the amplified library of PCR products into pUC-TT, a 9 µl of PCR sample were combined with 1 µl of the linearized pUC-TT vector and 1 µl (8 units) of the FPG glycosylase and incubated for 15 minutes at 37° C. to cleave at 8-oxo-guanine residues. The reaction was incubated for additional 15 minutes at room temperature to allow annealing of the complementary extensions.

Chemically-competent *E. coli* ER1992 cells were transformed with 10 µl of the assembly reaction. Recombinants were selected by plating the transformation reaction (LB+Amp) plates. More than $4 \times 10^3$ transformants were recovered after 18 hours incubation at 37° C. 27 out of total 32 individual transformants that were screened by colony PCR carried the insert varying from 0.3 kb to 1.3 kb in length. Plasmid DNA from five individual transformants that carried the longest inserts (from 0.9 kb to 1.3 kb) was purified and sequenced across the insert region. All of them carried the same genomic DNA segment that is localized on the 3' side from the known region of the *Pseudomonas alcaligenes* NEB#545 super-integron.

What is claimed is:

1. A method of generating a single-strand region on a polynucleotide molecule comprising:
   (a) providing in a reaction mixture, a polynucleotide molecule having a single modified nucleotide on one strand of a duplex at a specific location; and
   (b) enzymatically cleaving the polynucleotide molecule at the modified nucleotide, by adding two or more enzymes to a reaction mixture wherein at least one of the enzymes is a DNA glycosylase and at least one of the enzymes is a cleaving enzyme; and wherein the DNA glycosylase and the cleaving enzyme having an activity ratio of at least 2:1 in the reaction mixture, the activity ratio being the ratio of a first rate of forming an abasic site by excision of the modified nucleotide from the polynucleotide by DNA glycosylase to a second rate of cleaving at the abasic site in the polynucleotide by the cleaving enzyme, the first and second rates determined for a single predetermined molar amount of the modified nucleotide in the polynucleotide.

2. A method according to claim 1, wherein the polynucleotide molecule is a product of a primer pair-dependent DNA amplification of a target molecule.

3. A method according to claim 2, wherein introducing the modified nucleotide into the polynucleotide further comprises introducing the modified nucleotide into one or both primers in the primer pair.

4. A method according to claim 1, wherein the reaction mixture further comprises a second polynucleotide having a modified nucleotide and wherein the single strand region is a single-stranded extension of less than 10 nucleotides such that the single stranded extension on the first polynucleotide is complementary to a second single-stranded extension on the second polynucleotide molecule.

5. A method for joining a plurality of linear polynucleotide molecules to form a single molecule, comprising:
    (a) forming a single-stranded extension on one or both ends of each of the plurality of polynucleotide molecules using the method of claim 1, such that at least one single-stranded extension on one polynucleotide molecule is complementary to a single-stranded extension on another polynucleotide molecule; and
    (b) allowing the plurality of polynucleotide molecules to associate to form the single molecule.

6. A method for inserting a target molecule into a recipient molecule, comprising:
    (a) forming a first and a second single-stranded extension having less than 10 nucleotides on a first and a second end of a recipient molecule using the method of claim 1, wherein the first and second single-stranded extension may be the same or different from each other;
    (b) forming single-stranded extensions on the ends of a target molecule using the method of claim 1, wherein the single-stranded extensions are complementary to the first and the second single-stranded extension on the recipient molecule; and
    (c) allowing the recipient molecule and the target molecule to associate to form a single molecule.

7. A method according to claim 6, wherein the target molecule is a product of joining a plurality of polynucleotide molecules each having a single strand extension generated according to claim 1.

8. A method according to claim 7, wherein the plurality of polynucleotides molecules comprise A domains.

9. A method according to claim 8, wherein the DNA domains are exons.

10. A method according to claim 1, wherein the single strand region is a single strand extension on one end of the polynucleotide.

* * * * *